US010449336B2

(12) United States Patent
Foy et al.

(10) Patent No.: US 10,449,336 B2
(45) Date of Patent: Oct. 22, 2019

(54) TEMPORARY OCCLUSIONS BALLOON DEVICES AND METHODS FOR PREVENTING BLOOD FLOW THROUGH A VASCULAR PERFORATION

(71) Applicant: The Spectranetics Corporation, Colorado Springs, CO (US)

(72) Inventors: Grant Foy, Colorado Springs, CO (US); Jay Harper, Castle Rock, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 220 days.

(21) Appl. No.: 15/474,455

(22) Filed: Mar. 30, 2017

(65) Prior Publication Data
US 2017/0203082 A1 Jul. 20, 2017

Related U.S. Application Data

(63) Continuation-in-part of application No. 15/071,533, filed on Mar. 16, 2016.
(Continued)

(51) Int. Cl.
*A61B 17/08* (2006.01)
*A61D 1/00* (2006.01)
(Continued)

(52) U.S. Cl.
CPC ..... *A61M 25/1011* (2013.01); *A61B 17/0057* (2013.01); *A61B 17/00491* (2013.01);
(Continued)

(58) Field of Classification Search
CPC ................ A61M 25/10; A61M 25/101; A61M 2025/105; A61M 2025/1059;
(Continued)

(56) References Cited

U.S. PATENT DOCUMENTS

| 3,834,394 A | 9/1974 | Hunter et al. |
| 4,413,989 A | 11/1983 | Schjeldahl et al. |
(Continued)

FOREIGN PATENT DOCUMENTS

| EP | 0760688 B1 | 11/2001 |
| EP | 0981387 B1 | 11/2003 |
(Continued)

OTHER PUBLICATIONS

B. Braun Interventional Systems, One Tyshak Balloon Dilation Catheter Instructions for Use, 2 pages, Publicly Available Before the Earliest Priority Date.
(Continued)

*Primary Examiner* — Melanie R Tyson

(57) ABSTRACT

A device for occluding a perforation in a blood vessel includes an expandable member. The expandable member includes a central expandable balloon disposed between a proximal and a distal balloon, wherein the proximal and distal balloons each contain first and second compositions, respectively. The proximal, central and distal balloons have respective stiffnesses, and the central balloon has a third stiffness that is less than the first and second stiffnesses. Upon expansion, the central balloon causes the proximal balloon and the distal balloon to substantially simultaneously release the first and second compositions, thereby allowing the first composition and the second composition to combine in-situ and form, therein, a biocompatible foam to occlude a perforation within the vasculature.

12 Claims, 27 Drawing Sheets

Related U.S. Application Data

(60) Provisional application No. 62/203,711, filed on Aug. 11, 2015, provisional application No. 62/212,023, filed on Aug. 31, 2015, provisional application No. 62/212,025, filed on Aug. 31, 2015, provisional application No. 62/233,869, filed on Sep. 28, 2015, provisional application No. 62/234,376, filed on Sep. 29, 2015, provisional application No. 62/260,945, filed on Nov. 30, 2015, provisional application No. 62/297,785, filed on Feb. 19, 2016.

(51) Int. Cl.
| | | |
|---|---|---|
| *A61M 25/10* | (2013.01) | |
| *A61B 17/00* | (2006.01) | |
| *A61B 17/12* | (2006.01) | |
| *A61M 25/00* | (2006.01) | |
| *A61B 90/00* | (2016.01) | |

(52) U.S. Cl.
CPC ...... *A61B 17/1214* (2013.01); *A61B 17/1219* (2013.01); *A61B 17/12036* (2013.01); *A61B 17/12186* (2013.01); *A61B 17/12195* (2013.01); *A61M 25/0097* (2013.01); *A61M 25/1002* (2013.01); *A61B 17/1204* (2013.01); *A61B 17/12136* (2013.01); *A61B 2017/005* (2013.01); *A61B 2017/0065* (2013.01); *A61B 2017/00495* (2013.01); *A61B 2017/00623* (2013.01); *A61B 2017/00659* (2013.01); *A61B 2017/00676* (2013.01); *A61B 2017/00884* (2013.01); *A61B 2017/00898* (2013.01); *A61B 2017/00942* (2013.01); *A61B 2017/1205* (2013.01); *A61B 2090/037* (2016.02); *A61M 2025/105* (2013.01); *A61M 2025/1059* (2013.01)

(58) Field of Classification Search
CPC .......... A61B 17/00491; A61B 17/0057; A61B 17/12022; A61B 17/12027; A61B 17/12031; A61B 17/12036; A61B 17/1204; A61B 17/12131; A61B 17/12136; A61B 17/12181; A61B 17/12186; A61B 17/12195; A61B 17/1219; A61B 2017/00495; A61B 2017/00646; A61B 2017/0065; A61B 2017/00659; A61B 2017/00676
See application file for complete search history.

(56) References Cited

U.S. PATENT DOCUMENTS

| | | |
|---|---|---|
| 4,545,390 A | 10/1985 | Leary |
| 4,689,041 A | 8/1987 | Corday et al. |
| 4,836,204 A | 6/1989 | Landymore et al. |
| 5,273,536 A | 12/1993 | Savas |
| 5,304,121 A | 4/1994 | Sahatjian |
| 5,338,298 A | 8/1994 | McIntyre |
| 5,358,487 A | 10/1994 | Miller |
| 5,383,856 A | 1/1995 | Bersin |
| 5,417,689 A | 5/1995 | Fine |
| 5,439,445 A | 8/1995 | Kontos |
| 5,447,497 A | 9/1995 | Sogard et al. |
| 5,470,313 A | 11/1995 | Crocker et al. |
| 5,496,311 A | 3/1996 | Abele et al. |
| 5,540,679 A | 7/1996 | Fram et al. |
| 5,599,306 A | 2/1997 | Klein et al. |
| 5,613,948 A | 3/1997 | Avellanet |
| 5,759,170 A | 6/1998 | Peters |
| 5,765,568 A | 6/1998 | Sweezer et al. |
| 5,766,151 A | 6/1998 | Valley et al. |
| 5,795,331 A | 8/1998 | Cragg et al. |
| 5,797,878 A | 8/1998 | Bleam |
| 5,800,393 A | 9/1998 | Sahota |
| 5,820,595 A | 10/1998 | Parodi |
| 5,823,996 A | 10/1998 | Sparks |
| 5,843,027 A | 12/1998 | Stone et al. |
| 5,843,116 A | 12/1998 | Crocker et al. |
| 5,865,787 A | 2/1999 | Shapland et al. |
| 5,885,244 A | 3/1999 | Leone et al. |
| 5,985,307 A | 11/1999 | Hanson et al. |
| 6,048,333 A | 4/2000 | Lennox et al. |
| 6,071,271 A | 6/2000 | Baker et al. |
| 6,159,197 A | 12/2000 | Heuser |
| 6,176,821 B1 | 1/2001 | Crocker et al. |
| 6,221,043 B1 | 4/2001 | Fischell et al. |
| 6,251,094 B1 | 6/2001 | Bleam |
| 6,258,019 B1 | 7/2001 | Verin et al. |
| 6,293,924 B1 | 9/2001 | Bagaoisan et al. |
| 6,315,757 B1 | 11/2001 | Chee et al. |
| 6,346,092 B1 | 2/2002 | Leschinsky |
| 6,458,069 B1 | 10/2002 | Tam et al. |
| 6,461,327 B1 | 10/2002 | Addis et al. |
| 6,485,500 B1 | 11/2002 | Kokish et al. |
| 6,491,663 B1 | 12/2002 | Lemelson |
| 6,540,721 B1 | 4/2003 | Voyles et al. |
| 6,572,633 B1 | 6/2003 | Löffler et al. |
| 6,579,847 B1 | 6/2003 | Unger |
| 6,613,066 B1 | 9/2003 | Fukaya et al. |
| 6,616,629 B1 | 9/2003 | Verin et al. |
| 6,623,504 B2 | 9/2003 | Vrba et al. |
| 6,626,861 B1 | 9/2003 | Hart et al. |
| 6,629,952 B1 | 10/2003 | Chien et al. |
| 6,645,167 B1 | 11/2003 | Whalen, II et al. |
| 6,652,441 B2 | 11/2003 | Weinberger et al. |
| 6,652,485 B1 | 11/2003 | Gaudoin et al. |
| 6,656,153 B1 | 12/2003 | Sakai et al. |
| 6,663,614 B1 | 12/2003 | Carter |
| 6,679,900 B2 | 1/2004 | Kieturakis et al. |
| 6,682,545 B1 | 1/2004 | Kester |
| 6,699,170 B1 | 3/2004 | Crocker et al. |
| 6,706,010 B1 | 3/2004 | Miki et al. |
| 6,723,070 B1 | 4/2004 | Arai et al. |
| 6,743,208 B1 | 6/2004 | Coyle |
| 6,743,227 B2 | 6/2004 | Seraj et al. |
| 6,875,209 B2 | 4/2005 | Zvuloni et al. |
| 6,902,571 B2 | 6/2005 | Owens et al. |
| 6,936,057 B1 | 8/2005 | Nobles |
| 6,955,658 B2 | 10/2005 | Murray et al. |
| 6,960,186 B1 | 11/2005 | Fukaya et al. |
| 7,137,395 B2 | 11/2006 | Fried et al. |
| 7,169,140 B1 | 1/2007 | Kume |
| 7,232,452 B2 | 6/2007 | Adams et al. |
| 7,247,147 B2 | 7/2007 | Nishide et al. |
| 7,306,575 B2 | 12/2007 | Barbut et al. |
| 7,322,959 B2 | 1/2008 | Warnack et al. |
| 7,402,172 B2 | 7/2008 | Chin et al. |
| 7,491,188 B2 | 2/2009 | Holman et al. |
| 7,645,290 B2 | 1/2010 | Lucas |
| 7,674,240 B2 | 3/2010 | Webler et al. |
| 7,722,568 B2 | 5/2010 | Lenker et al. |
| 7,727,228 B2 | 6/2010 | Abboud et al. |
| 7,862,575 B2 | 1/2011 | Tal |
| 7,862,577 B2 | 1/2011 | Gray et al. |
| 7,909,794 B2 | 3/2011 | Briscoe et al. |
| 7,931,663 B2 | 4/2011 | Farnan et al. |
| 7,942,850 B2 | 5/2011 | Levit et al. |
| 7,967,836 B2 | 6/2011 | Warnack et al. |
| 8,021,386 B2 | 9/2011 | Davidson et al. |
| 8,066,667 B2 | 11/2011 | Hayman et al. |
| 8,172,783 B1 | 5/2012 | Ray |
| 8,177,779 B2 | 5/2012 | Joye et al. |
| 8,182,446 B2 | 5/2012 | Schaeffer et al. |
| 8,221,342 B2 | 7/2012 | Mesallum |
| 8,231,617 B2 | 7/2012 | Satake |
| 8,235,941 B2 | 8/2012 | Hayman et al. |
| 8,292,913 B2 | 10/2012 | Warnack et al. |
| 8,323,307 B2 | 12/2012 | Hardert |
| 8,348,890 B2 | 1/2013 | Gerrans et al. |
| 8,372,034 B2 | 2/2013 | Levit et al. |
| 8,382,787 B2 | 2/2013 | Burton et al. |

(56) References Cited

U.S. PATENT DOCUMENTS

| | | |
|---|---|---|
| 8,414,611 B2 | 4/2013 | Chalekian |
| 8,419,714 B2 | 4/2013 | Webler et al. |
| 8,486,046 B2 | 7/2013 | Hayman et al. |
| 8,518,105 B2 | 8/2013 | Hossainy et al. |
| 8,563,510 B2 | 10/2013 | Hakimimehr et al. |
| 8,574,225 B2 | 11/2013 | Reynolds |
| 8,667,838 B2 | 3/2014 | Hoem et al. |
| 8,708,996 B2 | 4/2014 | Consigny et al. |
| 8,740,961 B2 | 6/2014 | Fulton et al. |
| 8,784,602 B2 | 7/2014 | Schaeffer et al. |
| 8,801,662 B2 | 8/2014 | Doshi et al. |
| 8,852,146 B2 | 10/2014 | Horn et al. |
| 8,864,705 B2 | 10/2014 | Nishigishi |
| 8,936,568 B2 | 1/2015 | Webler et al. |
| 8,974,409 B2 | 3/2015 | Hayman et al. |
| 8,986,339 B2 | 3/2015 | Warnack et al. |
| 9,044,580 B2 | 6/2015 | Freyman et al. |
| 9,173,817 B2 | 11/2015 | Sharma et al. |
| 9,358,042 B2 | 6/2016 | Magee |
| 9,504,807 B2 | 11/2016 | Drasler et al. |
| 9,522,215 B2 | 12/2016 | Rago et al. |
| 9,579,449 B2 | 2/2017 | Sharma et al. |
| 2002/0010411 A1 | 1/2002 | Macoviak et al. |
| 2002/0026210 A1 | 2/2002 | Abdel-Gawwad |
| 2002/0133217 A1 | 9/2002 | Sirhan et al. |
| 2003/0004462 A1 | 1/2003 | Halpin |
| 2003/0050600 A1 | 3/2003 | Ressemann et al. |
| 2003/0050660 A1 | 3/2003 | Hackett |
| 2003/0163154 A1 | 8/2003 | Miyata et al. |
| 2003/0199914 A1 | 10/2003 | Diaz |
| 2003/0220666 A1 | 11/2003 | Mirigian et al. |
| 2004/0006305 A1 | 1/2004 | Hebert et al. |
| 2004/0122362 A1 | 6/2004 | Houser et al. |
| 2004/0249243 A1 | 12/2004 | Kleiner |
| 2004/0267196 A1 | 12/2004 | Miki et al. |
| 2005/0015047 A1 | 1/2005 | Shah |
| 2005/0033263 A1 | 2/2005 | Gottlieb et al. |
| 2005/0075711 A1 | 4/2005 | Neary |
| 2005/0209674 A1 | 9/2005 | Kutscher et al. |
| 2006/0095065 A1 | 5/2006 | Tanimura et al. |
| 2006/0167442 A1 | 7/2006 | Hebert et al. |
| 2006/0173298 A1 | 8/2006 | Tucker |
| 2006/0258981 A1 | 11/2006 | Eidenschink |
| 2007/0203453 A1 | 8/2007 | Kenji Mod et al. |
| 2008/0287907 A1 | 11/2008 | Gregory et al. |
| 2009/0054922 A1 | 2/2009 | Broker |
| 2009/0076447 A1 | 3/2009 | Casas et al. |
| 2009/0105686 A1 | 4/2009 | Snow et al. |
| 2009/0131785 A1 | 5/2009 | Lee et al. |
| 2009/0192452 A1 | 7/2009 | Sasajima et al. |
| 2009/0306700 A1 | 12/2009 | Miyata et al. |
| 2010/0004623 A1 | 1/2010 | Hamilton et al. |
| 2010/0016833 A1 | 1/2010 | Ogle et al. |
| 2010/0185220 A1 | 7/2010 | Naghavi et al. |
| 2010/0324648 A1 | 12/2010 | Scheller et al. |
| 2011/0071498 A1 | 3/2011 | Hakimimehr et al. |
| 2011/0082465 A1 | 4/2011 | Verma |
| 2011/0190727 A1 | 8/2011 | Edmunds et al. |
| 2011/0190867 A1 | 8/2011 | Vonderwalde et al. |
| 2011/0202016 A1 | 8/2011 | Zugates et al. |
| 2012/0040137 A1 | 2/2012 | Palasis et al. |
| 2012/0107439 A1 | 5/2012 | Sharma et al. |
| 2012/0109177 A1 | 5/2012 | Ulmer |
| 2012/0157987 A1 | 6/2012 | Steinke et al. |
| 2012/0265287 A1 | 10/2012 | Sharma et al. |
| 2012/0310210 A1 | 12/2012 | Campbell et al. |
| 2012/0323211 A1* | 12/2012 | Ogle ............... A61K 47/32 604/500 |
| 2013/0073025 A1 | 3/2013 | Kassab |
| 2013/0090679 A1 | 4/2013 | Hoem et al. |
| 2013/0165925 A1 | 6/2013 | Mathur et al. |
| 2013/0172923 A1 | 7/2013 | Webler et al. |
| 2013/0211381 A1 | 8/2013 | Feld |
| 2013/0310687 A1 | 11/2013 | Kenji Takizawa et al. |
| 2013/0317418 A1 | 11/2013 | Freyman et al. |
| 2014/0018732 A1 | 1/2014 | Bagaoisan et al. |
| 2014/0094893 A1 | 4/2014 | Gerber |
| 2014/0100646 A1 | 4/2014 | Hassan et al. |
| 2014/0180248 A1 | 6/2014 | Salik |
| 2014/0228745 A1 | 8/2014 | Sharma et al. |
| 2014/0249475 A1 | 9/2014 | Pacetti |
| 2014/0257181 A1 | 9/2014 | Speck |
| 2014/0257266 A1 | 9/2014 | Kasprzyk et al. |
| 2014/0276135 A1 | 9/2014 | Agah et al. |
| 2014/0277399 A1 | 9/2014 | Pacetti et al. |
| 2014/0316367 A1 | 10/2014 | Zugates et al. |
| 2015/0012031 A1 | 1/2015 | Rago et al. |
| 2015/0032087 A1 | 1/2015 | Shibata et al. |
| 2015/0051634 A1 | 2/2015 | Kravik et al. |
| 2015/0080875 A1 | 3/2015 | Kasprzyk et al. |
| 2015/0112256 A1 | 4/2015 | Byrne et al. |
| 2015/0165171 A1 | 6/2015 | Warnack et al. |
| 2015/0223819 A1 | 8/2015 | Rago et al. |
| 2015/0224235 A1 | 8/2015 | Sharma et al. |
| 2016/0051264 A1 | 2/2016 | Freyman et al. |
| 2016/0082144 A1 | 3/2016 | Freyman et al. |
| 2016/0114125 A1 | 4/2016 | Di Caprio et al. |
| 2016/0278783 A1 | 9/2016 | Magee |
| 2016/0279302 A1 | 9/2016 | Sharma et al. |
| 2017/0042519 A1 | 2/2017 | Sotak et al. |

FOREIGN PATENT DOCUMENTS

| | | |
|---|---|---|
| EP | 0853957 B1 | 6/2004 |
| EP | 1129737 B1 | 7/2005 |
| EP | 1051990 B1 | 10/2008 |
| EP | 2002779 A2 | 3/2009 |
| EP | 1879652 B1 | 6/2012 |
| EP | 1802368 B1 | 7/2013 |
| WO | 1994002195 A1 | 2/1994 |
| WO | 1998050101 A1 | 11/1998 |
| WO | 1999002202 A2 | 1/1999 |
| WO | 2004096339 A1 | 11/2004 |
| WO | 2009154720 A1 | 12/2009 |
| WO | 2010026578 A1 | 3/2010 |
| WO | 2010048729 A1 | 5/2010 |
| WO | 2010078875 A1 | 7/2010 |
| WO | 2012015623 A1 | 2/2012 |
| WO | 2012027138 A1 | 3/2012 |
| WO | 2012078612 A2 | 6/2012 |
| WO | 2014004160 A1 | 1/2014 |
| WO | 2014102611 A2 | 7/2014 |
| WO | 2014152742 A2 | 9/2014 |
| WO | 2014158687 A1 | 10/2014 |
| WO | 2015021375 A1 | 2/2015 |

OTHER PUBLICATIONS

B. Braun Interventional Systems, Z-MED II Balloon Dilation Catheter Instructions for Use, 2 pages, Publicly Available Before the Earliest Priority Date.

Bard Peripheral Vascular, Atlas PTA Dilation Catheter, 4 pages, Publicly Available Before the Earliest Priority Date.

Boston Scientific, Equalizer Occlusion Balloon Catheter Directions for Use, 6 pages, Publicly Available Before the Earliest Priority Date.

Cook Medical, Coda and Coda LP Balloon Catheters Instructions for Use, 36 pages, Publicly Available Before the Earliest Priority Date.

Cordis, Maxi LD Brochure, 2 pages, Publicly Available Before the Earliest Priority Date.

Dispomedica, Occlusion Catheter, 1 page, Publicly Available Before the Earliest Priority Date.

Edwards Lifesciences, Fogarty Occlusion Catheters—Temporary Vessel Occlusion, 2 pages, Publicly Available Before the Earliest Priority Date.

Gore, Q50 PLUS Stent Graft Balloon Catheter, http://www.goremedical.com/q50/, Publicly Available Before the Earliest Priority Date.

International Preliminary Report on Patentablity issued in PCT/US2014/019274, dated Sep. 24, 2015, 10 pages.

(56) References Cited

OTHER PUBLICATIONS

International Search Report and Written Opinion issued for PCT/US2014/019274 dated Jun. 3, 2014, 14 pages.
International Search Report and Written Opinion issued in PCT/US2016/046489, dated Nov. 10, 2016, 12 pages.
ISOMed, Occlusion Catheter Single Lumen, http://www.fbmedical.fr/en/occlusion-catheter, Publicly Available Before the Earliest Priority Date.
LeMaitre Vascular, Distal Perfusion Catheter Instructions for Use, 4 pages, Publicly Available Before the Earliest Priority Date.
LeMaitre Vascular, LeMaitre Aortic Occlusion Catheter Instructions for Use, 4 pages, Publicly Available Before the Earliest Priority Date.
Medtronic, Reliant Stent Graft Balloon Catheter, 2 pages, Publicly Available Before the Earliest Priority Date.
SentreHeart, Product Catalog, 6 pages, Publicly Available Before the Earliest Priority Date.

\* cited by examiner

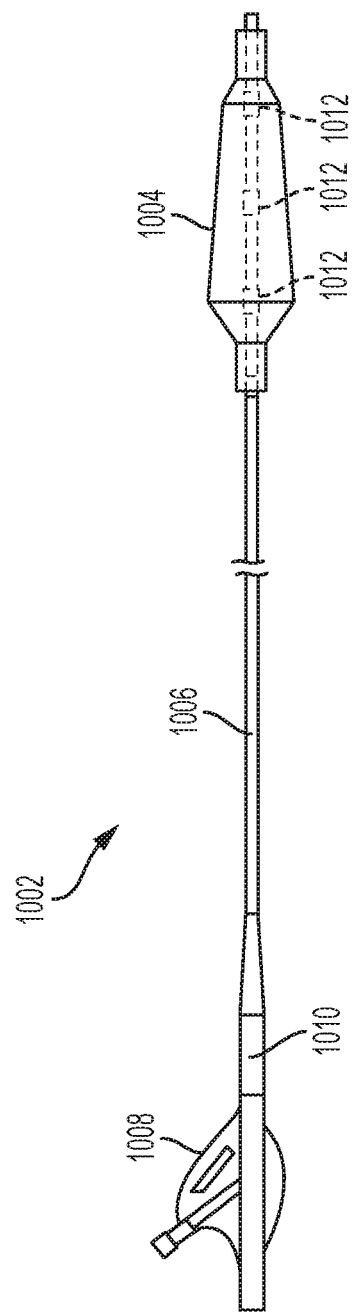

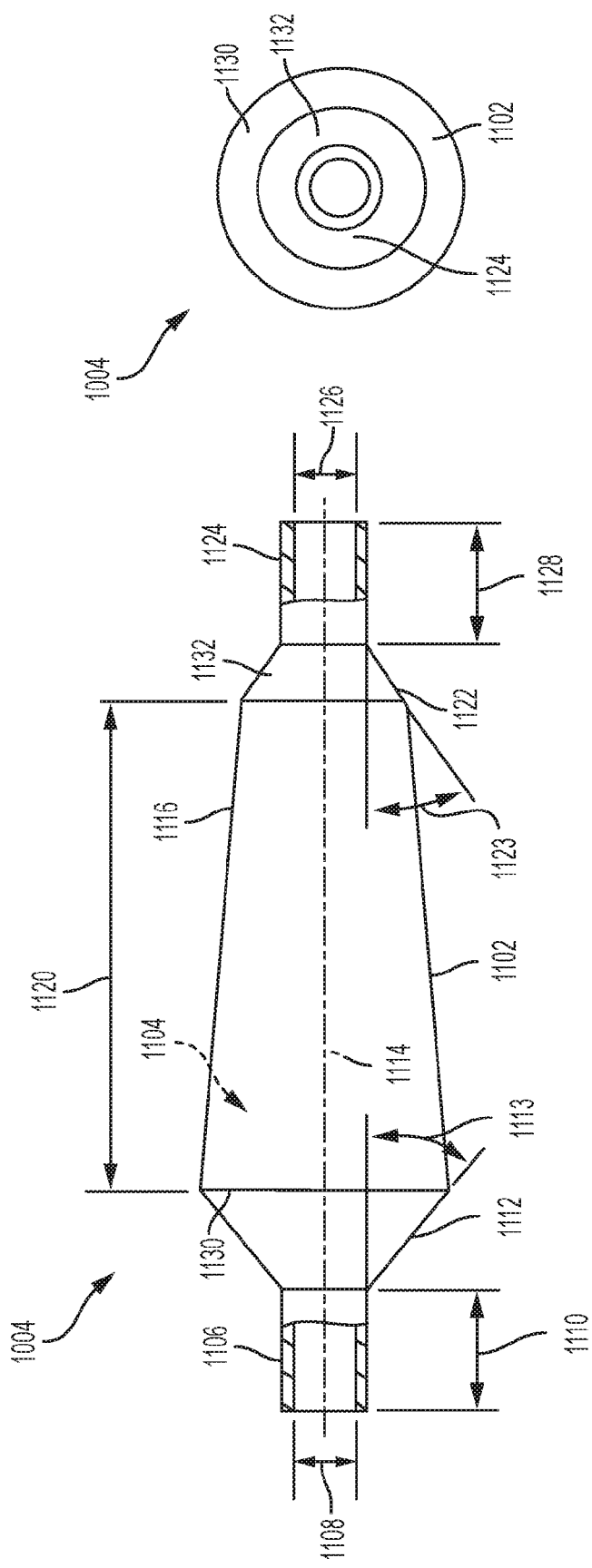

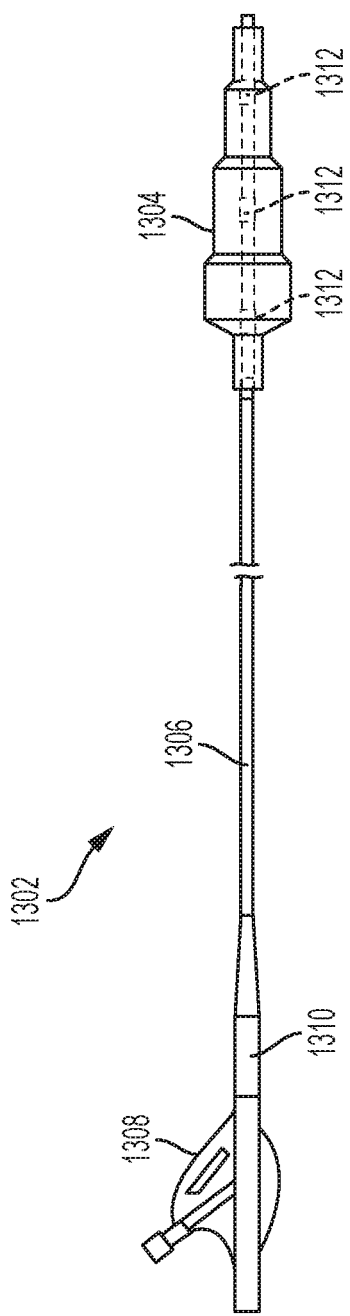

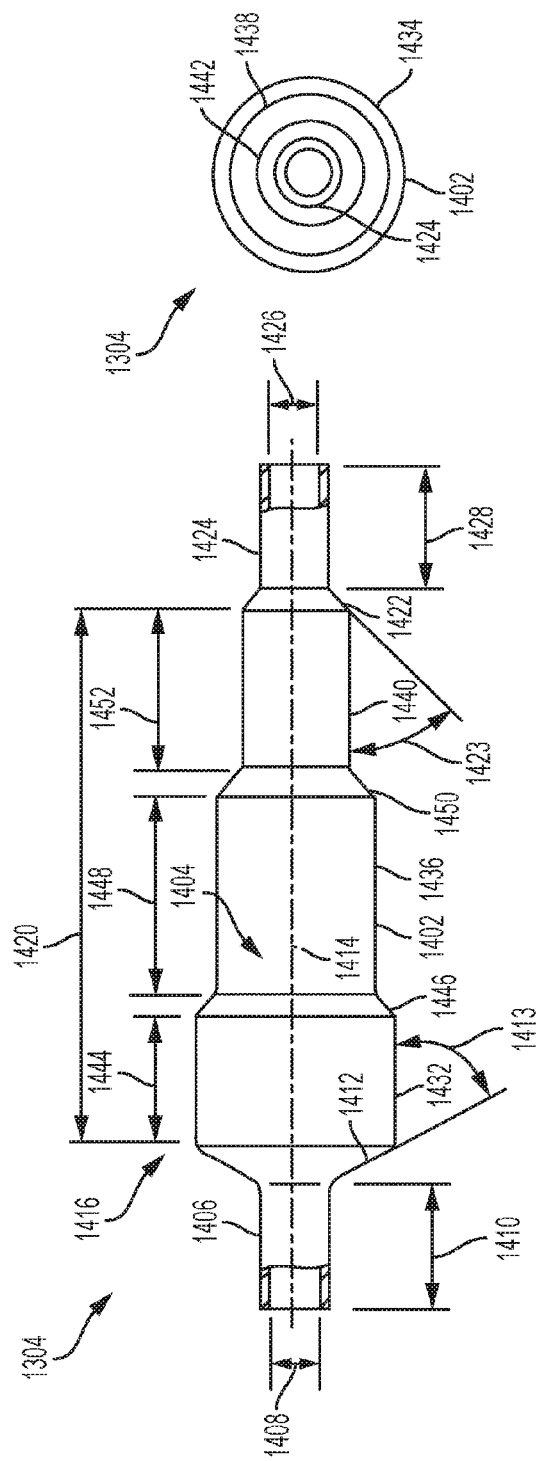

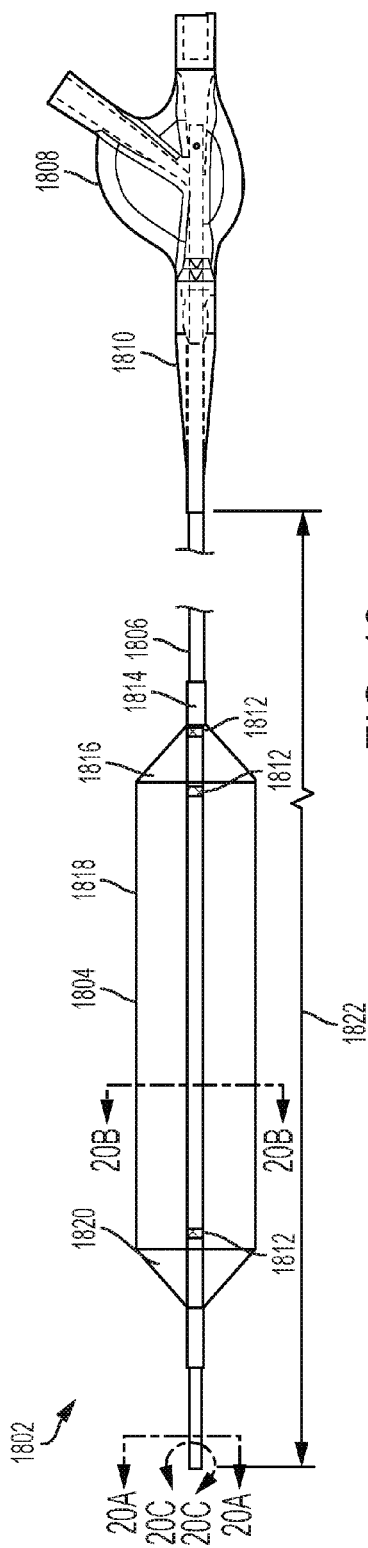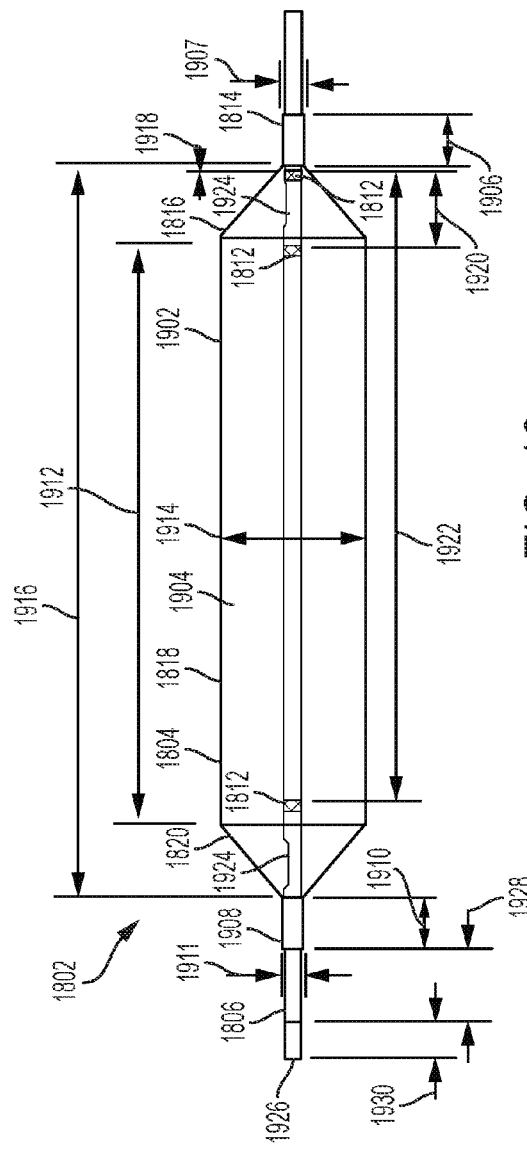
FIG. 18
FIG. 19

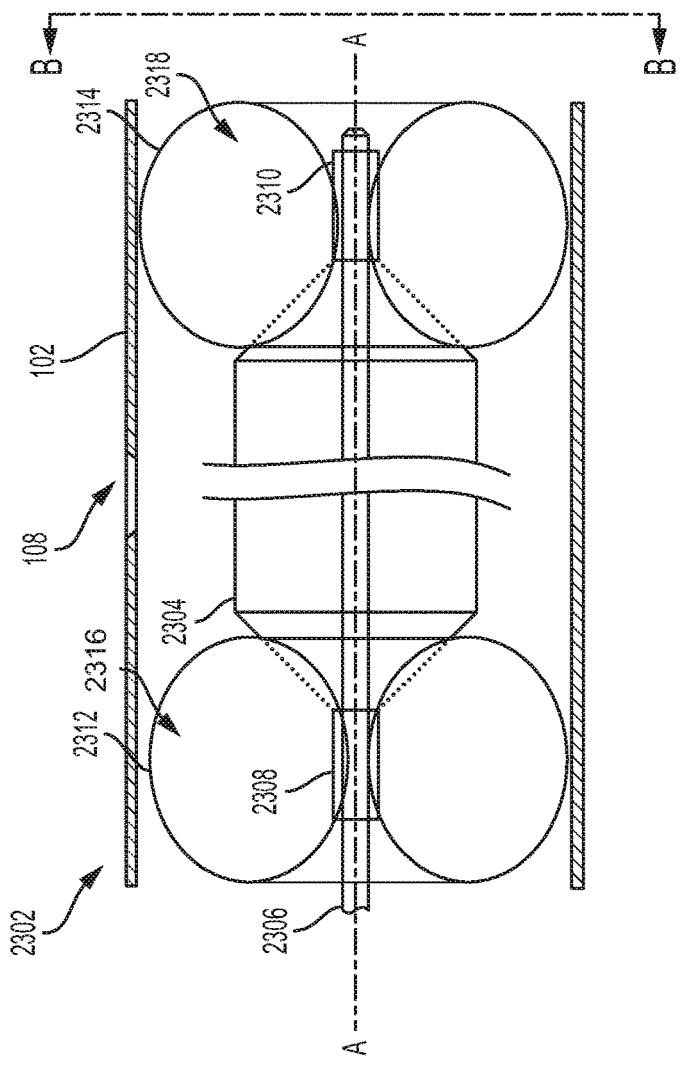
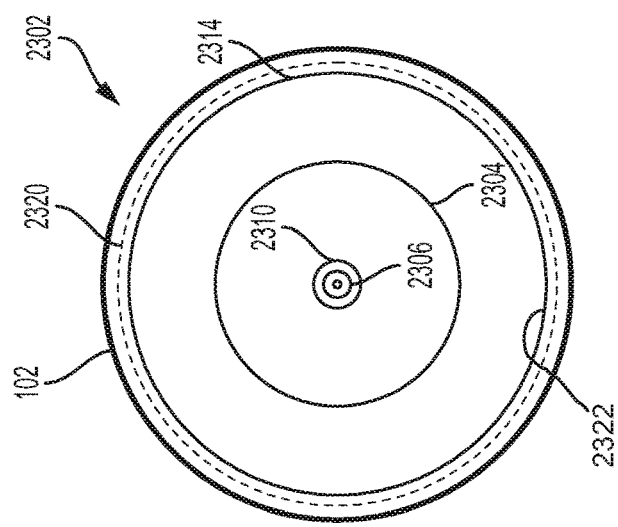
FIG. 23A
FIG. 23B

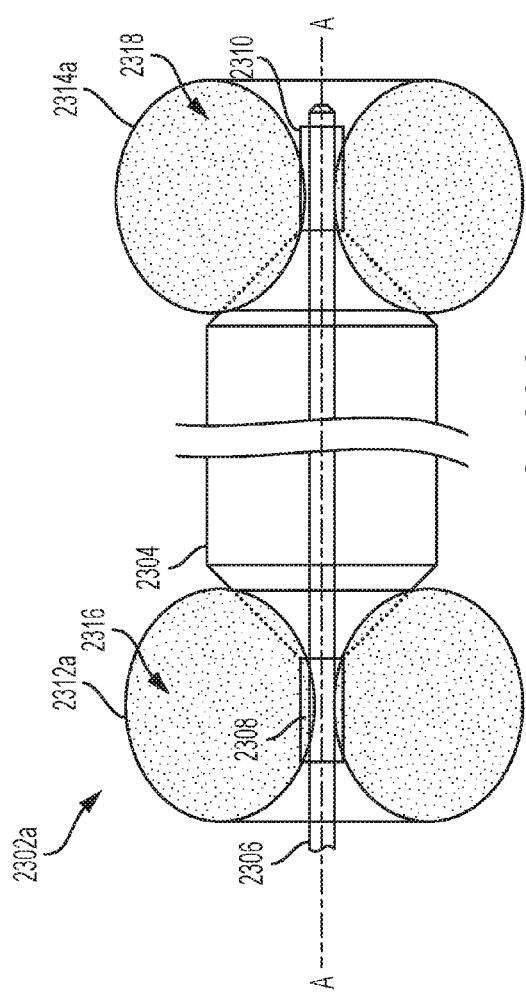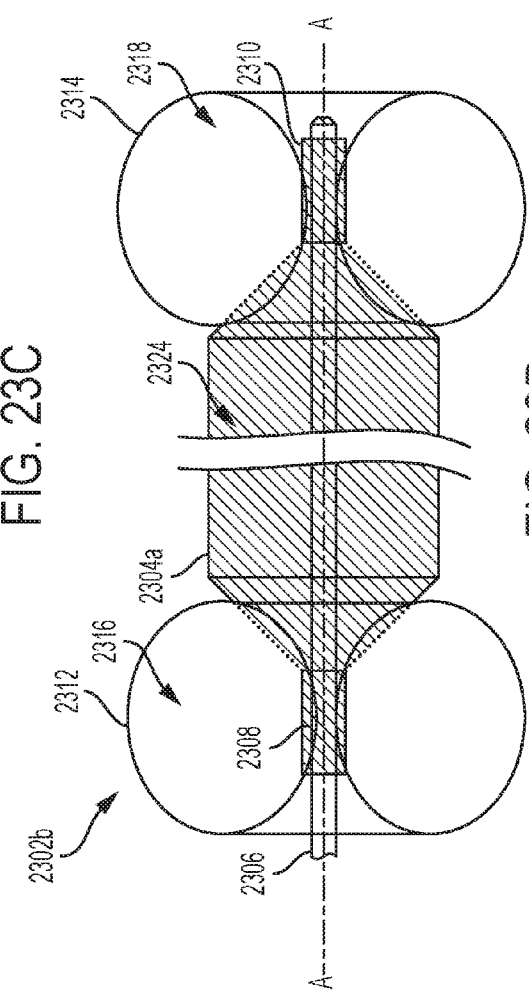

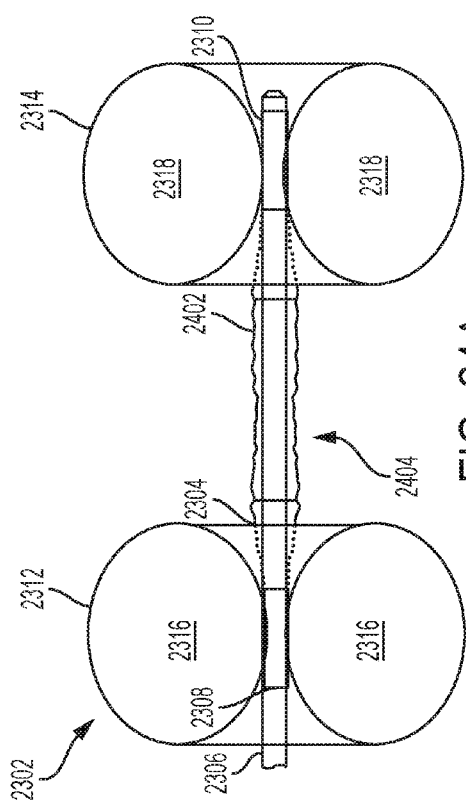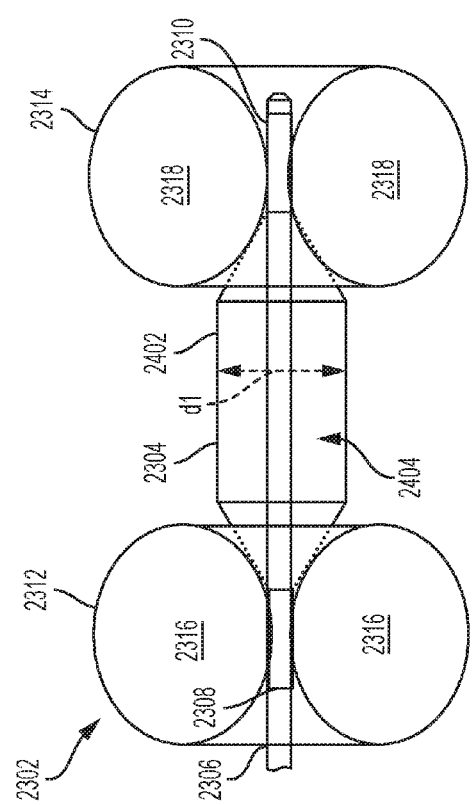

TEMPORARY OCCLUSIONS BALLOON DEVICES AND METHODS FOR PREVENTING BLOOD FLOW THROUGH A VASCULAR PERFORATION

CROSS REFERENCE TO RELATED APPLICATION

The present application is a continuation-in-part of co-pending U.S. Ser. No. 15/071,533, filed Mar. 16, 2016, which is related to commonly owned U.S. Provisional Application Ser. No. 62/203,711, filed Aug. 11, 2015, entitled "TEMPORARY OCCLUSION BALLOON DEVICES AND METHODS FOR PREVENTING BLOOD FLOW THROUGH A VASCULAR PERFORATION," commonly owned U.S. Provisional Application Ser. No. 62/212,023, filed Aug. 31, 2015, entitled "TEMPORARY OCCLUSION BALLOON DEVICES AND METHODS FOR PREVENTING BLOOD FLOW THROUGH A VASCULAR PERFORATION," commonly owned U.S. Provisional Application Ser. No. 62/212,025, filed Aug. 31, 2015, entitled "TEMPORARY OCCLUSION BALLOON DEVICES AND METHODS FOR PREVENTING BLOOD FLOW THROUGH A VASCULAR PERFORATION," commonly owned U.S. Provisional Application Ser. No. 62/233,869, filed Sep. 28, 2015, entitled "TEMPORARY OCCLUSION BALLOON DEVICES AND HEMOSTATIC COMPOSITIONS FOR PREVENTING BLOOD FLOW THROUGH A VASCULAR PERFORATION," commonly owned U.S. Provisional Application Ser. No. 62/234,376, filed Sep. 29, 2015, entitled "TEMPORARY OCCLUSION BALLOON DEVICES AND METHODS FOR PREVENTING BLOOD FLOW THROUGH A VASCULAR PERFORATION," and commonly owned U.S. Provisional Application Ser. No. 62/260,945, filed Nov. 30, 2015, entitled "TEMPORARY OCCLUSION BALLOON DEVICES AND METHODS FOR PREVENTING BLOOD FLOW THROUGH A VASCULAR PERFORATION," and commonly owned U.S. Provisional Application Ser. No. 62/297,785, filed Feb. 19, 2016, entitled "TEMPORARY OCCLUSION BALLOON DEVICES AND METHODS FOR PREVENTING BLOOD FLOW THROUGH A VASCULAR PERFORATION," which are hereby incorporated herein by reference in their entireties for all that they teach and for all purposes.

FIELD OF THE DISCLOSURE

The present disclosure relates generally to medical occlusion balloon devices and methods. In particular, the present disclosure provides temporary occlusion balloon devices and methods for preventing blood flow through vascular perforations formed during cardiac lead removal procedures.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached to the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a lead locking device is described and illustrated in U.S. Pat. No. 6,167,315 to Coe et al., which is incorporated herein by reference in its entirety for all that it teaches and for all purposes.

A mechanical device to extract leads includes a flexible tube called a sheath that passes over the lead and/or the surrounding tissue. The sheath typically may include a cutting blade, such that upon advancement, the cutting blade and sheath cooperate to separate the scar tissue from other scar tissue including the scar tissue surrounding the lead. In some cases, the cutting blade and sheath may also separate the tissue itself from the lead. Once the lead is separated from the surrounding tissue and/or the surrounding tissue is separated from the remaining scar tissue, the lead may be inserted into a hollow lumen of the sheath for removal and/or be removed from the patient's vasculature using some other mechanical devices, such as the mechanical traction device previously described in U.S. Pat. No. 8,961,551 to Taylor, which is hereby incorporated herein by reference in its entirety for all that it teaches and for all purposes. An example of such a device and a method used to extract leads is described and illustrated in U.S. Pat. No. 5,651,781 to Grace, which is incorporated herein by reference in its entirety for all that it teaches and for all purposes.

Examples of a laser catheter assembly or laser sheaths that may be used for removing a surgically implanted lead is a coronary laser atherectomy catheter by the Spectranetics Corporation under the trade names SLSII™ and GlideLight™. At the distal end, such catheters include multiple fiber optic laser emitters that surround a lumen. As the fiber optic laser emitters cut the tissue surrounding the lead, the sheath slides over the lead and surrounding tissue, which enter the lumen.

Lead extraction is generally a very safe procedure. However, as with any invasive procedure, there are potential risks. For example, while using any of the tools discussed above to remove a lead, the tool may accidentally pierce, cut, or perforate the vein or artery through which the tool is traveling, thereby allowing blood to escape the patient's vascular system. The rate at which blood escapes may be high if the accidental opening is created close to the patient's heart. Accordingly, a clinician must address the situation quickly to mitigate the amount of blood that escapes from the patient, thereby minimizing potential long-term harm to the patient.

Systems relating to in-situ forming polymer foams for use in a patient to stabilize wounds, such as in large cavities, are disclosed in U.S. Pat. Nos. 9,044,580, 9,173,817, 9,522,215, and 9,579,449, and in U.S. Publ. Appl. Nos. 2011/0202016, 2012/0040137, 2012/0265287, 2014/0316367, 2015/0223819, 2015/0224235, 2016/0051264, 2016/0082144, and 2016/0279302, which are hereby incorporated herein by reference in their entireties for all that they teach and for all purposes. A need exists for more precise delivery devices and methods for use in a patient's vasculature, for example to occlude a perforation in a blood vessel, in which tight tolerances and delicate tissue surroundings dictate more sophisticated solutions.

SUMMARY

These and other needs are addressed by the various aspects, embodiments, and configurations of the present disclosure. In some embodiments, a device for occluding a perforation in a blood vessel includes a catheter shaft that has a first lumen and a second lumen. The first lumen is adapted to receive at least one of a guidewire and an implanted cardiac lead, and the second lumen is adapted to receive an inflation fluid. The second lumen may include a cross-sectional area at a location along a length of the catheter shaft between 0.65 $mm^2$ and 1.90 $mm^2$. The device further includes an inflatable balloon that is carried by the catheter shaft. The inflatable balloon is adapted to receive the inflation fluid from the second lumen. The inflatable balloon has a working length of about 65 mm to about 80 mm and an inflated diameter of about 20 mm to about 25 mm. The device may also include cross-sectional area within the second lumen that includes a crescent shape, and the cross-sectional area of the second lumen may be about 1 $mm^2$, the radius of the crescent-like cross-sectional shape may have a radius of about between 0.50 mm to 1.50 mm, such as about 1 mm.

In some embodiments, a device for occluding a perforation in a blood vessel includes an inflatable balloon coated with a hemostatic composition to reduce the rate of blood flow loss and allow more time for planning and initiating surgical repair of the perforation. The hemostatic composition can include one or more hemostatic blood clotting agents, as well as one or more adjuvants and/or excipients.

A device according to the previous paragraph, wherein the inflatable balloon includes polyurethane.

A device according to any of the previous two paragraphs, wherein the inflatable balloon includes a proximal tapered portion, a distal tapered portion, and a working portion disposed between the proximal tapered portion and the distal tapered portion, the working portion having the inflated diameter of about 20 mm to about 25 mm.

A device according to any of the previous three paragraphs, wherein the first lumen and the second lumen are non-concentrically disposed within the catheter shaft.

A device according to any of the previous four paragraphs, further including at least one radiopaque marker carried by the catheter shaft.

A device according to any of the previous five paragraphs, wherein at least one radiopaque marker includes a band extending around a circumference of the catheter shaft.

A device according to any of the previous six paragraphs, wherein at least one radiopaque marker includes at least a first radiopaque marker and a second radiopaque marker.

A device according to any of the previous seven paragraphs, wherein at least one radiopaque marker further includes at least a third radiopaque marker.

A device according to any of the previous eight paragraphs, wherein the hemostatic composition includes a fibrin-based clotting agent that promotes blood clotting and wound healing (e.g., fibrin sealant).

A device according to any of the previous nine paragraphs, wherein the hemostatic composition includes one or more clotting agents that promotes blood clotting and wound healing, and a coating agent to prevent premature loss of the hemostatic composition while positioning the balloon adjacent to the perforation.

A device according to any of the previous ten paragraphs, wherein the inflatable balloon includes a proximal portion, a distal portion, and an intermediate portion disposed between the proximal and distal portions, wherein the first, second, and third radiopaque markers are carried within the inflatable balloon, and wherein the first radiopaque marker is axially aligned with the proximal portion, the second radiopaque marker is axially aligned with the intermediate portion, and the third radiopaque marker is axially aligned with the distal portion.

A device according to any of the previous eleven paragraphs, wherein the inflatable balloon includes a proximal neck, a proximal tapered portion, a working portion, a distal tapered portion and a distal neck, wherein the first, second, and third radiopaque markers are carried within the inflatable balloon, and wherein the first radiopaque marker is axially aligned with an intersection of the proximal neck and the proximal tapered portion, wherein the second radiopaque marker is axially aligned with the intersection of the proximal tapered portion and the working portion, and the third radiopaque marker is axially aligned with the intersection of the working portion and the distal tapered portion.

A device according to any of the previous twelve paragraphs, further comprising a third lumen being adapted to facilitate passage of blood from a first end to a second end of the inflatable balloon.

A device according to any of the previous thirteen paragraphs, wherein the catheter shaft includes the third lumen.

A device according to any of the previous fourteen paragraphs, further comprising an occlusion patch detachably carried by the inflatable balloon, the occlusion patch being deployable from the inflatable balloon to occlude the perforation.

A device according to any of the previous fifteen paragraphs, wherein the occlusion patch includes at least one adhesive adapted to maintain a position of the occlusion patch within the blood vessel.

A device according to any of the previous sixteen paragraphs, wherein the at least one adhesive is adapted to be activated by application of at least one of heat, pH, and light.

A device according to any of the previous seventeen paragraphs, wherein the occlusion patch includes a scaffold structure adapted to facilitate tissue growth therein.

A device according to any of the previous eighteen paragraphs, wherein the occlusion patch includes stem cells to facilitate bioabsorption of the occlusion patch.

A device according to any of the previous nineteen paragraphs, wherein the occlusion patch includes at least one hormonal agent adapted to promote wound healing.

In some embodiments, a device for occluding a perforation in a blood vessel includes a catheter shaft that has a first lumen and a second lumen. The first lumen is adapted to receive at least one of a guidewire and an implanted cardiac lead, and the second lumen is adapted to receive an inflation fluid. The device further includes an inflatable balloon carried by the catheter shaft. The inflatable balloon is adapted to receive the inflation fluid from the second lumen. The inflatable balloon includes polyurethane having a Shore A durometer of about 85 A.

A device according to the previous paragraph, wherein the first lumen and the second lumen are non-concentrically disposed within the catheter shaft.

A device according to any of the previous two paragraphs, wherein the first lumen and the second lumen are non-concentrically disposed within the catheter shaft.

A device according to any of the previous three paragraphs, further including at least one radiopaque marker carried by the catheter shaft.

A device according to any of the previous four paragraphs, wherein the at least one radiopaque marker includes a band extending around a circumference of the catheter shaft.

A device according to any of the previous five paragraphs, wherein the at least one radiopaque marker includes at least a first radiopaque marker and a second radiopaque marker.

A device according to any of the previous six paragraphs, wherein the at least one radiopaque marker further includes at least a third radiopaque marker.

A device according to any of the previous seven paragraphs, wherein the inflatable balloon includes a proximal portion, a distal portion, and an intermediate portion disposed between the proximal and distal portions, wherein the first, second, and third radiopaque markers are carried within the inflatable balloon, and wherein the first radiopaque marker is axially aligned with the proximal portion, the second radiopaque marker is axially aligned with the intermediate portion, and the third radiopaque marker is axially aligned with the distal portion.

A device according to any of the previous eight paragraphs, further comprising a third lumen being adapted to facilitate passage of blood from a first end to a second end of the inflatable balloon.

A device according to any of the previous nine paragraphs, wherein the catheter shaft includes the third lumen.

A device according to any of the previous ten paragraphs, wherein the inflatable balloon is coated with a hemostatic composition to reduce the rate of blood flow loss.

A device according to any of the previous eleven paragraphs, wherein the hemostatic composition comprises a fibrin-based clotting agent.

A device according to any of the previous twelve paragraphs, wherein the hemostatic composition comprises a coating agent.

A device according to any of the previous thirteen paragraphs, further comprising an occlusion patch detachably carried by the inflatable balloon, the occlusion patch being deployable from the inflatable balloon to occlude the perforation.

A device according to any of the previous fourteen paragraphs, wherein the occlusion patch includes at least one adhesive adapted to maintain a position of the occlusion patch within the blood vessel.

A device according to any of the previous fifteen paragraphs, wherein the at least one adhesive is adapted to be activated by application of at least one of heat, pH, and light.

A device according to any of the previous sixteen paragraphs, wherein the occlusion patch includes a scaffold structure adapted to facilitate tissue growth therein.

A device according to any of the previous seventeen paragraphs, wherein the occlusion patch includes stem cells to facilitate bioabsorption of the occlusion patch.

A device according to any of the previous eighteen paragraphs, wherein the occlusion patch includes at least one hormonal agent adapted to promote wound healing.

In some embodiments, a method for occluding a perforation in a blood vessel includes: (1) providing an occlusion balloon device including: a catheter shaft having a first lumen and a second lumen; an inflatable balloon carried by the catheter shaft, the inflatable balloon having a working length of about 65 mm to about 80 mm, and the inflatable balloon having an inflated diameter of about 20 mm to about 25 mm; (2) advancing the catheter shaft in the blood vessel until the inflatable balloon is positioned proximate the perforation; and (3) delivering an inflation fluid to the inflatable balloon via the second lumen to inflate the inflation balloon and thereby occlude the perforation.

A method according to the previous paragraph, wherein the inflation fluid includes saline and contrast solution.

A method according to any of the previous two paragraphs, wherein the inflation fluid includes about 80 percent saline and about 20 percent contrast solution.

A method according to any of the previous three paragraphs, wherein delivering the inflation fluid to the inflatable balloon includes delivering the inflation fluid at a pressure in the range of about 2 to about 3 atmospheres.

A method according to any of the previous four paragraphs, further comprising a third lumen being adapted to facilitate passage of blood from a first end to a second end of the inflatable balloon.

A method according to any of the previous five paragraphs, wherein the catheter shaft includes the third lumen.

A method according to any of the previous six paragraphs, wherein the inflatable balloon is coated with a hemostatic composition, and wherein delivering the inflation fluid to the inflatable balloon brings the hemostatic composition in contact with the vascular tissue at the site of the perforation.

A method according to any of the previous seven paragraphs, wherein the inflatable balloon is coated with a hemostatic composition to reduce the rate of blood flow loss.

A method according to any of the previous eight paragraphs, wherein the hemostatic composition comprises a fibrin-based clotting agent.

A method according to any of the previous nine paragraphs, wherein the hemostatic composition comprises a coating agent.

A method according to any of the previous ten paragraphs, wherein the occlusion balloon device comprises an occlusion patch detachably carried by the inflatable balloon, and delivering the inflation fluid to the inflatable balloon to inflate the inflation balloon and thereby occlude the perforation includes deploying the occlusion patch from the inflatable balloon and thereby occluding the perforation.

A method according to any of the previous eleven paragraphs, the occlusion patch includes at least one adhesive, and the method further comprises activating the at least one adhesive to secure the occlusion patch within the blood vessel.

A method according to any of the previous twelve paragraphs, activating the at least one adhesive to secure the occlusion patch within the blood vessel includes applying at least one of heat, pH, and light.

A method according to any of the previous thirteen paragraphs, the occlusion patch includes a scaffold structure adapted to facilitate tissue growth therein.

A method according to any of the previous fourteen paragraphs, the occlusion patch includes stem cells to facilitate bioabsorption of the occlusion patch.

A method according to any of the previous fifteen paragraphs, the occlusion patch includes at least one hormonal agent adapted to promote wound healing.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising a working portion having a length of about 115 mm to about 65 mm, and the working portion tapering inwardly from a first outer diameter to a second outer diameter.

A device according to the previous paragraph, wherein the working portion tapers inwardly from the first outer diameter to the second outer diameter at a constant slope.

A device according to any of the previous two paragraphs, wherein the working portion tapers inwardly from the first outer diameter to the second outer diameter at a constant slope.

A device according to any of the previous three paragraphs, wherein the first outer diameter is disposed at a proximal portion of the inflatable balloon and the second outer diameter is disposed at a distal portion of the inflatable balloon.

A device according to any of the previous four paragraphs, wherein the first outer diameter is in a range of about 35 mm to about 50 mm.

A device according to any of the previous five paragraphs, wherein the second outer diameter is in a range of about 16 mm to about 30 mm.

A device according to any of the previous six paragraphs, further comprising at least one radiopaque marker carried by the catheter shaft.

A device according to any of the previous seven paragraphs, wherein the inflatable balloon comprises polyurethane.

A device according to any of the previous eight paragraphs, wherein the inflatable balloon comprises polyurethane having a Shore A durometer of about 85 A.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising polyurethane having a Shore A durometer of about 85 A, and the inflatable balloon having a working portion that tapers inwardly from a first outer diameter to a second outer diameter.

A device according to the previous paragraph, wherein the working portion tapers inwardly from the first outer diameter to the second outer diameter at a constant slope.

A device according to any of the previous two paragraphs, wherein the first outer diameter is disposed at a proximal portion of the inflatable balloon and the second outer diameter is disposed at a distal portion of the inflatable balloon.

A device according to any of the previous three paragraphs, wherein the first outer diameter is in a range of about 35 mm to about 50 mm.

A device according to any of the previous four paragraphs, wherein the second outer diameter is in a range of about 16 mm to about 30 mm.

A device according to any of the previous five paragraphs, further comprising at least one radiopaque marker carried by the catheter shaft.

A device according to any of the previous six paragraphs, wherein the inflatable balloon comprises polyurethane.

A device according to any of the previous seven paragraphs, wherein the inflatable balloon comprises polyurethane having a Shore A durometer of about 85 A.

In some embodiments, a method for occluding a perforation in a blood vessel, the method comprises: providing an occlusion balloon device that comprises a catheter shaft having a first lumen and a second lumen; an inflatable balloon carried by the catheter shaft, the inflatable balloon comprising a working portion having a length of about 115 mm to about 65 mm, and the working portion tapering inwardly from a first outer diameter to a second outer diameter; advancing the catheter shaft in the blood vessel until the inflatable balloon is positioned proximate the perforation; and delivering an inflation fluid to the inflatable balloon via the second lumen to inflate the inflation balloon and thereby occlude the perforation.

A method according to the previous paragraph, wherein the inflation fluid comprises saline and contrast solution.

A method according to any of the previous two paragraphs, wherein the inflation fluid comprises about 80 percent saline and about 20 percent contrast solution.

A method according to any of the previous three paragraphs, wherein delivering the inflation fluid to the inflatable balloon comprises delivering the inflation fluid at a pressure in the range of about 2 to about 3 atmospheres.

In some embodiments, a device for occluding a perforation in a blood vessel, the device comprising: a catheter shaft having a first lumen and a second lumen, the first lumen being adapted to receive at least one of a guidewire and an implanted cardiac lead, and the second lumen being adapted to receive an inflation fluid, and an inflatable balloon carried by the catheter shaft and adapted to receive the inflation fluid from the second lumen, the inflatable balloon comprising a working portion having a length of about 115 mm to about 65 mm, wherein the working portion tapers inwardly from a first outer diameter to a second outer diameter, wherein the inflatable balloon comprises a first ratio of the length to the first outer diameter of about 1.3:1 to about 3.3:1 and a second ratio of the length to the second outer diameter of about 2.2:1 to about 7.2:1.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising a working portion having a length of about 125 mm to about 85 mm, and the working portion comprising a plurality of sections each having a different outer diameter.

A device according to the previous paragraph, wherein the plurality of sections of the working portion comprises a first section having a first outer diameter; a second section having a second outer diameter; and a third section having a third outer diameter.

A device according to any of the previous two paragraphs, wherein the first outer diameter is greater than the second outer diameter and the second outer diameter is greater than the third outer diameter.

A device according to any of the previous three paragraphs, wherein the first section is proximally disposed relative to the second section and the second section is proximally disposed relative to the third section.

A device according to any of the previous four paragraphs, wherein the first outer diameter is in a range of about 60 mm to about 40 mm.

A device according to any of the previous five paragraphs, wherein the second outer diameter is in a range of about 30 mm to about 10 mm.

A device according to any of the previous six paragraphs, wherein the third outer diameter is in a range of about 26 mm to about 6 mm.

A device according to any of the previous seven paragraphs, wherein the first section has a length in a range of about 18 mm to about 25 mm.

A device according to any of the previous eight paragraphs, wherein the second section has a length in a range of about 52 mm to about 60 mm.

A device according to any of the previous nine paragraphs, wherein the third section has a length in a range of about 20 mm to about 40 mm.

A device according to any of the previous ten paragraphs, further comprising at least one radiopaque marker carried by the catheter shaft.

A device according to any of the previous eleven paragraphs, wherein the inflatable balloon comprises polyurethane.

A device according to any of the previous twelve paragraphs, wherein the inflatable balloon comprises polyurethane having a Shore A durometer of about 85 A.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising polyurethane having a Shore A durometer of about 85 A, and the inflatable balloon having a working portion comprising a plurality of sections each having a different outer diameter.

A device according to the previous paragraph, wherein the plurality of sections of the working portion comprises a first section having a first outer diameter; a second section having a second outer diameter; and a third section having a third outer diameter.

A device according to any of the previous two paragraphs, wherein the first outer diameter is greater than the second outer diameter and the second outer diameter is greater than the third outer diameter.

A device according to any of the previous three paragraphs, wherein the first section is proximally disposed relative to the second section and the second section is proximally disposed relative to the third section.

A device according to any of the previous four paragraphs, wherein the first outer diameter is in a range of about 60 mm to about 40 mm.

A device according to any of the previous five paragraphs, wherein the second outer diameter is in a range of about 30 mm to about 10 mm.

A device according to any of the previous six paragraphs, wherein the third outer diameter is in a range of about 26 mm to about 6 mm.

A device according to any of the previous seven paragraphs, wherein the first section has a length in a range of about 18 mm to about 25 mm.

A device according to any of the previous eight paragraphs, wherein the second section has a length in a range of about 52 mm to about 60 mm.

A device according to any of the previous nine paragraphs, wherein the third section has a length in a range of about 20 mm to about 40 mm.

A device according to any of the previous ten paragraphs, further comprising at least one radiopaque marker carried by the catheter shaft.

A device according to any of the previous eleven paragraphs, wherein the inflatable balloon comprises polyurethane.

A device according to any of the previous twelve paragraphs, wherein the inflatable balloon comprises polyurethane.

A device according to any of the previous thirteen paragraphs, wherein the inflatable balloon comprises polyurethane having a Shore A durometer of about 85 A.

In some embodiments, a method for occluding a perforation in a blood vessel comprises: providing an occlusion balloon device comprising: a catheter shaft having a first lumen and a second lumen; an inflatable balloon carried by the catheter shaft, the inflatable balloon comprising a working portion having a length of about 125 mm to about 85 mm, and the working portion comprising a plurality of sections each having a different outer diameter; advancing the catheter shaft in the blood vessel until the inflatable balloon is positioned proximate the perforation; and delivering an inflation fluid to the inflatable balloon via the second lumen to inflate the inflation balloon and thereby occlude the perforation.

A device according to the previous paragraph, wherein the inflation fluid comprises saline and contrast solution.

A device according to any of the previous two paragraphs, wherein the inflation fluid comprises about 80 percent saline and about 20 percent contrast solution.

A device according to any of the previous three paragraphs, wherein delivering the inflation fluid to the inflatable balloon comprises delivering the inflation fluid at a pressure in the range of about 2 to about 3 atmospheres.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising a working portion having a length of about 125 mm to about 85 mm, wherein the working portion comprises: a first section having a first outer diameter, a first ratio of the length to the first outer diameter being about 1.4:1 to about 3.1:1; a second section having a second outer diameter, a second ratio of the length to the second outer diameter being about 2.8:1 to about 12.5:1; and a third section having a third outer diameter, a third ratio of the length to the third outer diameter being about 3.3:1 to about 20.8:1.

A device according to the previous paragraph, wherein the first section is proximally disposed relative to the second section and the second section is proximally disposed relative to the third section.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon having a working length of about 80 mm, and the inflatable balloon having an inflated diameter of about 20 mm.

A device according to the previous paragraph, wherein the inflatable balloon comprises polyurethane.

A device according to any of the previous two paragraphs, wherein the inflatable balloon comprises a proximal tapered portion, a distal tapered portion, and a working portion disposed between the proximal tapered portion and the distal tapered portion, the working portion having the inflated diameter of about 20 mm.

A device according to any of the previous three paragraphs, wherein the first lumen and the second lumen are non-concentrically disposed within the catheter shaft.

A device according to any of the previous four paragraphs, further comprising at least one radiopaque marker carried by the catheter shaft.

A device according to any of the previous five paragraphs, wherein the at least one radiopaque marker comprises a band extending around a circumference of the catheter shaft.

A device according to any of the previous six paragraphs, wherein the at least one radiopaque marker comprises at least a first radiopaque marker and a second radiopaque marker.

A device according to any of the previous seven paragraphs, wherein the at least one radiopaque marker further comprises at least a third radiopaque marker.

In some embodiments, an expandable member for occluding a perforation in a blood vessel comprises a first balloon having a first stiffness and containing a first composition; a second balloon having a second stiffness and containing a second composition; and, a third balloon having a third stiffness, the third balloon being disposed between the first balloon and the second balloon, wherein the third stiffness is less than the first stiffness and the second stiffness, and whereupon expanding the third balloon causes the first balloon and the second balloon to release substantially simultaneously the first composition and the second composition to allow combining of the first composition and the second composition to form in-situ a biocompatible foam.

An expandable member according to the previous paragraph, the first balloon and the second balloon each having a pressure strength at burst less than that of the third balloon, whereupon expanding the third balloon causes the first balloon and the second balloon to break and release substantially simultaneously the first composition and the second composition.

An expandable member according to any of the previous two paragraphs, the first balloon further comprising a first plurality of micropores and the second balloon further comprising a second plurality of micropores whereupon expanding the third balloon causes the first balloon and the second balloon to expand and release substantially simultaneously the first composition through the first plurality of micropores and the second composition through the second plurality of micropores.

An expandable member according to any of the previous three paragraphs, further comprising a longitudinal axis, wherein the first balloon, the second balloon, and the third balloon are longitudinally offset relative to one another.

An expandable member according to any of the previous four paragraphs, wherein the first composition and the second composition are polymeric.

An expandable member according to any of the previous five paragraphs, wherein the first composition is polymeric and the second composition is aqueous.

An expandable member according to any of the previous six paragraphs, the third balloon further having an outer surface, wherein the outer surface is coated with a third composition, and wherein the third composition is combinable with one of the first composition, the second composition, or both to form in-situ the biocompatible foam.

An expandable member according to any of the previous seven paragraphs, further comprising a catheter shaft wherein the first balloon, the second balloon, and the third balloon are carried by the catheter shaft.

An expandable member according to any of the previous eight paragraphs, further comprising a sheath having an inner lumen, wherein at least one of the first balloon, the second balloon, and the third balloon is moveable longitudinally within the inner lumen.

An expandable member according to any of the previous nine paragraphs, wherein the first balloon comprises a plurality of first sub-balloons containing the first composition and the second balloon comprises a plurality of second sub-balloons containing the second composition.

An expandable member according to any of the previous ten paragraphs, further comprising a fourth balloon enveloping the first balloon, the second balloon, and the third balloon, wherein the fourth balloon is configured to break prior to the first balloon releasing the first composition and the second balloon releasing the second composition.

An expandable member according to any of the previous eleven paragraphs, wherein the biocompatible foam forms an occlusion patch.

In some embodiments, a method for occluding a perforation in a blood vessel comprises providing a catheter shaft, the catheter shaft having a proximal end and a distal end, and at least one lumen configured to receive an inflation medium; extending the catheter shaft into a patient's blood vessel, positioning the distal end of the catheter shaft proximate to a target perforation in a blood vessel; advancing an expandable member distally to at least the distal end of the catheter shaft, the expandable member comprising: a first balloon having a first stiffness and containing a first composition; a second balloon having a second stiffness and containing a second composition; and, a third balloon having a third stiffness, the third balloon being disposed between the first balloon and the second balloon, wherein the third stiffness is less than the first stiffness and the second stiffness; delivering the inflation medium through the at least one lumen to the third balloon via one or more apertures to expand the third balloon; expanding the third balloon to cause the first balloon and the second balloon to release substantially simultaneously the first composition and the second composition; combining the first composition and the second composition to form in-situ a biocompatible foam to form an occlusion patch for restricting the flow of blood.

A method for occluding a perforation in a blood vessel according to the previous paragraph, further comprising deflating the third balloon after the first balloon releases the first composition and the second balloon releases second composition.

A method for occluding a perforation in a blood vessel according to any of the previous two paragraphs, wherein the expandable member is carried by the catheter shaft.

A method for occluding a perforation in a blood vessel according to any of the previous three paragraphs, wherein the expandable member is disposed about an outer surface of the catheter shaft.

A method for occluding a perforation in a blood vessel according to any of the previous four paragraphs, wherein the expandable member is disposed within a sheath.

A method for occluding a perforation in a blood vessel according to any of the previous five paragraphs, wherein the first composition and the second composition are polymeric.

A method for occluding a perforation in a blood vessel according to any of the previous six paragraphs, wherein the first composition is polymeric and the second composition is aqueous.

A method for occluding a perforation in a blood vessel according to any of the previous seven paragraphs, the third balloon further having an outer surface, wherein the outer surface is coated with a third composition, and wherein the third composition is combinable with one of the first composition, the second composition, or both to form in-situ the biocompatible foam.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$—$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible-but possibly still flexible-catheter ("hard" catheter).

A "lead" is a conductive structure, typically an electrically insulated coiled wire. The electrically conductive material can be any conductive material, with metals and intermetallic alloys common. The outer sheath of insulative material is biocompatible and biostable (for example, non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term "occlude" and variations thereof as used herein refer to inhibiting flow through a structure, such as a vascular perforation.

The term "proximate" as used herein shall mean very near and/or adjacent. For example, the occlusion balloon may be very near or adjacent the perforation such that upon inflation, the occlusion balloon occludes blood flowing through the perforation.

It should be understood that every maximum numerical limitation given throughout the present disclosure is deemed to include each and every lower numerical limitation as an alternative, as if such lower numerical limitations were expressly written herein. Every minimum numerical limitation given throughout the present disclosure is deemed to include each and every higher numerical limitation as an alternative, as if such higher numerical limitations were expressly written herein. Every numerical range given throughout the present disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 10 is a side view of another occlusion balloon device according to embodiments of the present disclosure.

FIG. 11A is a partial longitudinal section view of a balloon of the occlusion balloon device of FIG. 10.

FIG. 11B is a front view of the balloon of FIG. 11A.

FIG. 13 is a side view of another occlusion balloon device according to embodiments of the present disclosure.

FIG. 14A is a partial longitudinal section view of a balloon of the occlusion balloon device of FIG. 13.

FIG. 14B is a front view of the balloon of FIG. 14A.

FIG. 18 is a side view of an occlusion balloon device according to embodiments of the present disclosure.

FIG. 19 is a side view of a distal portion of the occlusion balloon device of FIG. 18.

FIG. 23A is a side view of a distal portion of an expandable member in a vessel according to embodiments of the present disclosure.

FIG. 23B is a distal end view along axis A of FIG. 23A.

FIG. 23C is a schematic view of the rigid balloons as in FIG. 23A each including a plurality of micropores according to another embodiment of the present disclosure.

FIG. 23D is a schematic view of the inflatable balloon as in FIG. 23A having an external surface including a coating according to another embodiment of the present disclosure.

FIG. 24A is a side view of a distal portion of the expandable member of FIG. 23A in a deflated state wherein the inflatable balloon is an uninflated or unexpanded state. The deflated state may also be referred to as a resting or delivery state.

FIG. 24B is a side view of a distal portion of the expandable member of FIG. 23A in a first state wherein the inflatable balloon is in a partially inflated or expanded state.

DETAILED DESCRIPTION

Figure 1:
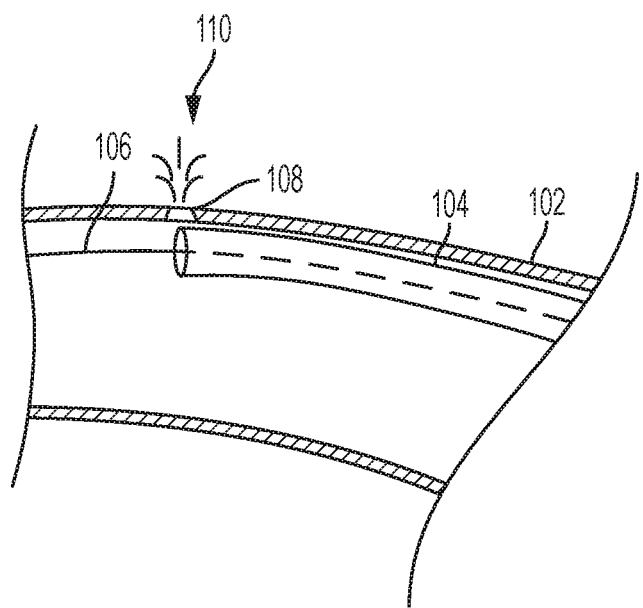
FIG. 1 is a partial cross sectional view of a vein perforated by a lead removal device during a lead removal procedure.

FIG. 1 generally shows a partial cross-sectional view of a blood vessel 102 (such as the superior vena cava, an innominate vein, a jugular vein, or the like) with an advancing lead removal catheter 104, which may include a mechanical device, a laser device or some other device, that accidentally perforates the wall of the blood vessel 102. More specifically, a cardiac lead 106 lies within the blood vessel 102. A distal end of the cardiac lead 106 (not shown) is coupled to a surgically implanted device, such as a pacemaker or defibrillator proximal to the patient's heart. The lead removal catheter 104 travels along the lead 106 from a proximal end (not shown) toward the distal end. The lead 106 may be disposed very close to a wall of the blood vessel 102 at one or more positions, such as in or near the superior vena cava or right atrium. In such a situation, as lead removal catheter 104 is advanced along the lead 106, a tip or cutting instrument of the lead removal catheter 104 (not shown) may accidently create a perforation 108 in the wall of the blood vessel 102, thereby causing bleeding 110.

Factors contributing to the occurrence of the perforation 108 may include the following: the sharpness of the bend in the lead 106; the structural integrity of the wall of the blood vessel 102 at positions in which the lead 106 is very close to the wall of the blood vessel 102; sharp bends in the blood vessel 102; the speed and/or force applied to the lead removal catheter 104 to advance the catheter 104; and/or various combinations of these and other factors known to those skilled in the art. In any case, upon detection of the perforation 108 (for example, via fluoroscopy, blood pressure monitoring, or the like), the lead removal catheter 104 may be immediately removed from the vasculature, and the one or more of the occlusion balloon devices according to embodiments of the present disclosure may be inserted into the vasculature and located adjacent the perforation 108 and employed to occlude the perforation 108. That is, an occlusion balloon device may be inserted into the blood vessel and occlude the perforation 108 while the lead removal catheter 104 remains in the blood vessel 102 or the lead removal catheter 104 may be removed from the blood vessel 102 prior to insertion and deployment of the occlusion balloon device in the blood vessel 102.

Figure 2:
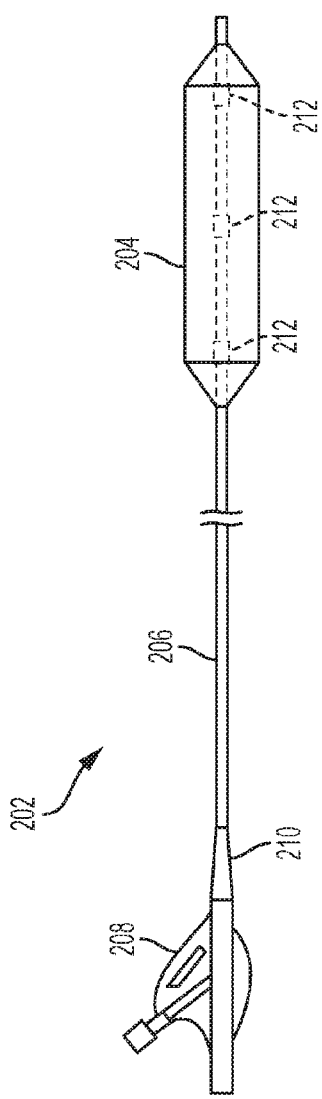
FIG. 2 is a side view of an occlusion balloon device according to embodiments of the present disclosure.

FIG. 2 is a side view of an exemplary occlusion balloon device 202 device according to embodiments of the present disclosure. The occlusion balloon device 202 generally includes an inflatable balloon 204 that is carried at a distal portion of a catheter shaft 206. The occlusion balloon device 202 also includes a connection hub 208 that is carried at a proximal portion of the catheter shaft 206. The connection hub 208 and the catheter shaft 206 may carry a distally-tapering strain relief 210 at an interface therebetween. The catheter shaft 206 may also carry one or more radiopaque markers 212 such that the position of the occlusion balloon device 202 may be determined via medical imaging (for example, via fluoroscopy). The catheter shaft 206 may carry, for example, three radiopaque markers 212 as shown in FIG. 2. A first radiopaque marker 212 may be axially aligned with a proximal portion of the inflatable balloon 204, a second radiopaque marker 212 may be axially aligned with an intermediate portion of the inflatable balloon 204, and a third radiopaque marker 212 may be axially aligned with a distal portion of the inflatable balloon 204.

Figure 3:
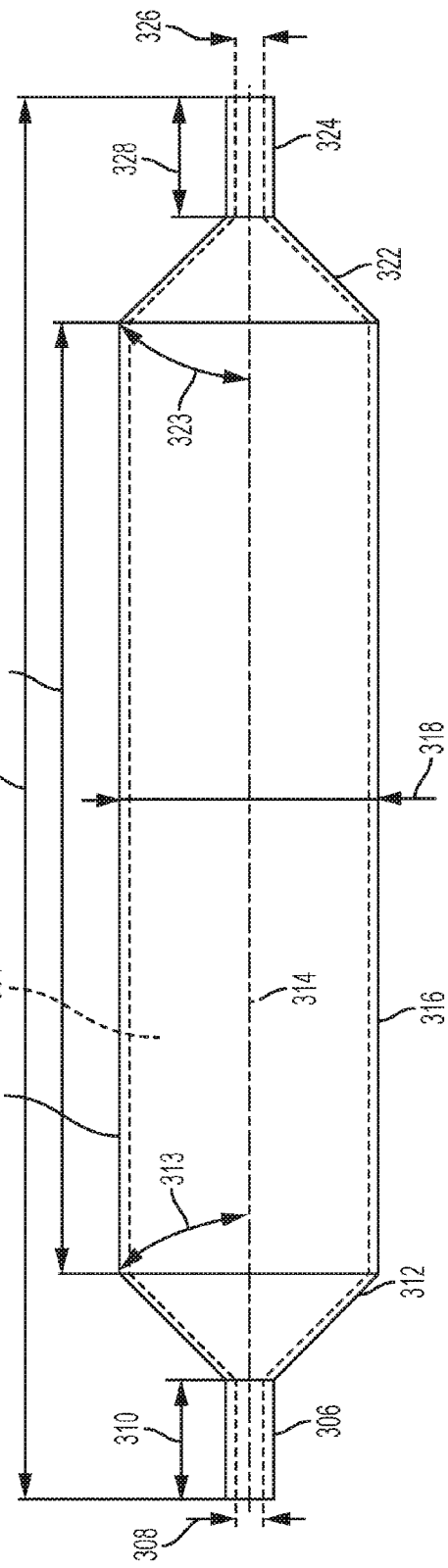
FIG. 3 is a side view of a balloon of the occlusion balloon device of FIG. 2.

FIG. 3 is a side view of the inflatable balloon 204 of the occlusion balloon device 202 of FIG. 2, wherein the inflatable balloon 204 is depicted in an inflated state. The inflatable balloon 204 may include a wall 302, an inflation chamber 304, an overall length 305, a proximal neck 306 having a length 310, a distal neck 324 having a length 328, a working portion 316 having a length 320, a proximal tapered portion 312 disposed between the proximal neck 306 and the working portion 316, and a distal tapered portion 322 disposed between the distal neck 324 and the working portion 316.

The wall 302 of the inflatable balloon 204 defines an inflation chamber 304. The inflation chamber 304 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the lead removal catheter 104 into the vasculature, positioning the inflatable balloon 204 adjacent the perforation 108 and inflating the inflatable balloon, the inflatable balloon 204 facilitates occlusion of the perforation 108.

In some embodiments, the inflatable balloon 204 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 204 may be formed of one or more elastomeric materials, such as polyurethane. For example, the inflatable balloon 204 may be formed of Pellethane®, specifically 80AE Pellethane®, which is available from The Lubrizol Corporation of Wickliffe, Ohio. The inflatable balloon 204 may have a Shore A durometer of about 85 A (that is, 85 A±4 A).

The inflatable balloon 204 may have an overall length 305 of about 98 mm (that is, 98 mm±3 mm) to about 82 mm (that is, 82 mm±3 mm).

The inflatable balloon 204 includes a proximal neck 306 that engages the catheter shaft 206 (via one or more adhesives, a compression fit, or the like). The proximal neck 306 may have an inner diameter 308 of about 2.5 mm (that is, 2.5 mm±0.07 mm). The proximal neck 306 may have a length 310 of about 10 mm (that is, 10 mm±1 mm). The proximal neck 306 may have a wall thickness of about 0.24 mm (that is, 0.24 mm±0.01 mm).

Distal to the proximal neck 306, the proximal neck 306 couples to a proximal tapered portion 312. The proximal tapered portion 312 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 204 is inflated, the proximal tapered portion 312 may be disposed at an angle 313 of about 45 degrees (that is, 45 degrees±0.5') relative to a longitudinal axis 314 of the inflatable balloon 204.

Distal to the proximal tapered portion 312, the proximal tapered portion 312 couples to a working portion 316. The working portion 316, when the inflatable balloon 204 is appropriately positioned and inflated, occludes the perforation 108. The working portion 316 may have an inflated outer diameter 318 of about greater than 20 mm (that is, 20 mm±2 mm), for example between about 20 mm (that is, 20 mm±2 mm) and about 30 mm (that is, 30 mm±2 mm) and possibly further between about 20 mm (that is, 20 mm±2 mm) and about 25 mm (that is, 25 mm±2 mm). The working portion 316 may have a length 320 of about 80 mm (that is, 80 mm±3 mm) to about 65 mm (that is, 65 mm±3 mm). The working portion 316 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The ratio of the length 320 of the working portion 302 to the outer diameter 318 of the inflatable balloon 204 in the inflated state is, therefore, about 2.6:1 to about 4:1. Having this ratio with a relatively constant inflated outer diameter 318 of about 20 mm to about 25 mm for a length 320 of about 80 mm to about 65 mm increases the likelihood that the inflatable balloon 204 will occlude the perforation 108 when placed adjacent the perforation 108 in the patient vasculature and inflated. That is, the length 320 of the working portion 302 of the inflatable balloon 204 is designed to be substantially longer than the perforation 108, thereby potentially increasing the clinician's ability to quickly locate and occlude the perforation.

As mentioned above, the working portion 316 of the inflatable balloon 204 may have an inflated outer diameter 318 of about greater than 20 mm (that is, 20 mm±2 mm), for example between about 20 mm (that is, 20 mm±2 mm) and about 30 mm (that is, 30 mm±2 mm) and possibly further between about 20 mm (that is, 20 mm±2 mm) and about 25 mm (that is, 25 mm±2 mm). Inflating the outer diameter 318 of the working portion 316 of the inflatable balloon 204 to this diameter increases the likelihood that the working portion 316 of the inflatable balloon 204 will be about the same diameter or slightly larger than the diameter of the blood vessel 102 at the perforation 108. Inflating the outer diameter 318 of the working portion 316 of the inflatable balloon 204 to be about the same diameter or slightly larger than the diameter of the blood vessel 102 at the perforation 108 increases the likelihood that the inflatable balloon 204 will block the perforation 108 without increasing its size.

Again, the inflatable balloon 204 may be formed of one or more elastomeric materials, such as polyurethane. To inflate the inflatable balloon 204 to the range of diameters referenced above, it may also be desirable to inflate the inflatable balloon 204 with an inflation fluid to a pressure within the balloon inflation chamber 304 from about 0 psi to about 3 psi. The amount of inflation fluid used to inflate the inflatable balloon 204 to such a pressure and/or at the desired diameter is about 20 ml (cc) to about 60 ml (cc).

Distal to the working portion 316, the working portion 316 couples to a distal tapered portion 322. The distal tapered portion 322 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 204 is inflated, the distal tapered portion 322 may be disposed at an angle 323 of about 45 degrees (that is, 45 degrees±0.5') relative to the longitudinal axis 314.

Distal to the distal tapered portion 322, the distal tapered portion 322 couples to a distal neck 324 that engages the catheter shaft 206 (via one or more adhesives, a compression fit, or the like). The distal neck 324 may have an inner diameter 326 of about 2.5 mm (that is, 2.5 mm±0.07 mm). The distal neck 324 may have a length 328 of about 10 mm (that is, 10 mm±1 mm). The distal neck 324 may have a wall thickness of about 0.24 mm (that is, 0.24 mm±0.01 mm).

Figure 4:
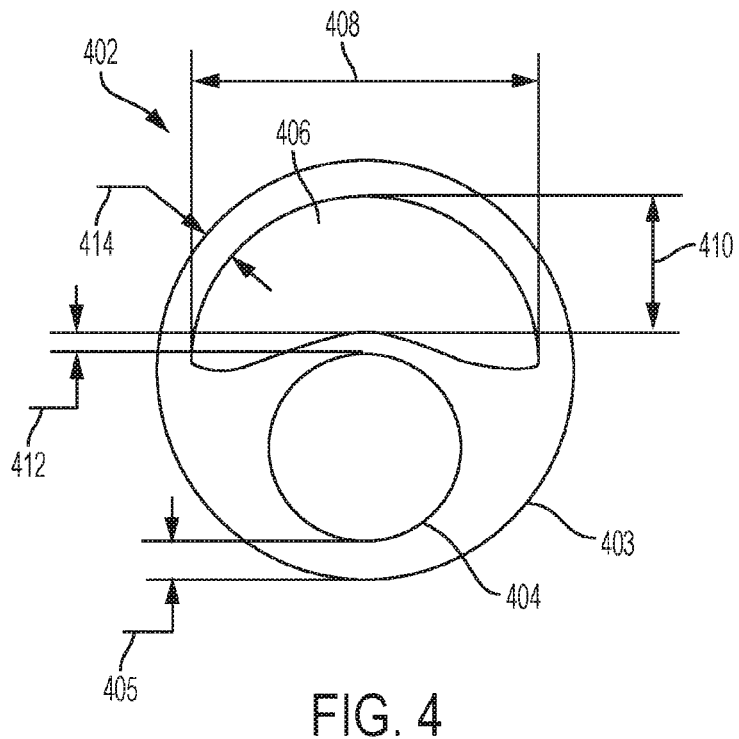
FIG. 4 is a cross-sectional view of an embodiment of a catheter shaft of the occlusion balloon device of FIG. 2.

FIG. 4 is a cross-sectional view of a first exemplary embodiment of a catheter shaft 402 that may be used as the catheter shaft 206 described above. The catheter shaft 402 may be formed of one or more elastomeric materials, such as polyurethane. For example, the catheter shaft 402 may be formed of Pellethane®, specifically 75D Pellethane®, which is available from The Lubrizol Corporation.

The catheter shaft 402 may have an outer diameter 403 of about 2.1 mm (that is, 2.1 mm 0.038 mm). The catheter shaft 402 may have a length of about 110 cm (that is, 110 cm±0.3 cm).

The catheter shaft 402 includes a first lumen 404 that is adapted to receive a guidewire or an implanted cardiac lead to guide the occlusion balloon device 202 to a position proximate the perforation 108. The first lumen 504 may, therefore, also be referred to as a guidewire lumen or an implanted lead lumen. The first lumen 404 is non-centrically disposed relative to the outer diameter 403 of the catheter shaft 402. Assuming that the first lumen 404 is adapted to receive a guidewire, the first lumen 404 may have circular cross section and have a diameter of about 0.94 mm (that is, 0.94 mm±0.025 mm). Again, assuming that the first lumen 404 is adapted to receive a guidewire, a minimum wall thickness 405 between the first lumen 404 and the outer diameter 403 may be about 0.15 mm (that is, 0.15 mm±0.025 mm). If, however, the first lumen 404 is adapted to receive an implanted cardiac lead, the first lumen 404 may have a larger circular cross section because the diameter of a cardiac lead is typically greater than 0.25 mm. Accordingly, the first lumen 404 may have a circular cross section greater than 0.25 mm. Also, although the first lumen 404 is depicted as having a circular cross section, the cross-sectional shape of the first lumen 404 may have a non-circular section, such as an oval.

The catheter shaft 402 also includes a second lumen 406 that is adapted to receive the inflation fluid from the connection hub 208 and deliver the inflation fluid to the balloon inflation chamber 304. The second lumen 506 may, therefore, also be referred to as an inflation lumen. The second lumen 406 is non-centrically disposed relative to the first lumen 404 and the outer diameter 403 of the catheter shaft 402. The second lumen 406 may have a circular cross section or a non-circular cross-sectional shape, such as a crescent-like cross-sectional shape. Assuming that the second lumen 406 has a crescent-like cross-sectional shape, the second lumen 406 may have a width 408 of about 1.8 mm (that is, 1.8 mm±0.025 mm). The second lumen 406 may have a height 410 in a plane that bisects the catheter shaft 402 of about 0.76 mm (that is, 0.76 mm±0.025 mm). It is desirable to introduce as much inflation fluid through the second lumen 406 and into the inflation chamber of the inflatable balloon as quickly as possible, in order to inflate the inflatable balloon as quickly as possible and minimize potential blood loss through the perforation. Accordingly, it is desirable to have as large as possible a cross-sectional area for the second lumen 406 for a given outer diameter 403 of the catheter shaft 402. For example, for an outer diameter 403 of 2.1 mm (that is, 2.1 mm±0.038 mm) to an outer diameter of 2.3 mm (that is, 2.3 mm±0.038 mm), the cross-sectional area for the second lumen 406 may be between 0.65 mm$^2$ and 1.90 mm$^2$ or any increment of 0.01 mm$^2$ therebetween, such as 0.66, 0.67, 0.68, 0.69, 0.70 . . . 1.0 . . . 1.5 . . . 1.9 mm$^2$.

A minimum wall thickness 412 between the second lumen 406 and the first lumen 404 may be about 0.1 mm (that is, 0.1 mm±0.025 mm). A minimum wall thickness 414 between the second lumen 406 and the outer diameter 403 may be about 0.15 mm (that is, 0.15 mm±0.025 mm). Having two or more of the following allows the clinician to quickly inflate the inflation chamber 304 of inflatable balloon 204 with the inflation fluid: a crescent-like cross-sectional shape for the second lumen 406; a wall thickness 405 between the first lumen 404 and the outer diameter 403 about 0.15 mm; a wall thickness 414 between the second lumen 406 and the outer diameter 403 about 0.15 mm; and wall thickness 412 between the second lumen 406 and the first lumen 404 about 0.1 mm.

The catheter shaft 402 also includes one or more apertures (not shown) that couple the second lumen 406 to the exterior of the catheter shaft 402 and the balloon inflation chamber 304. That is, the second lumen 406 delivers the inflation fluid to the inflatable balloon 204 via one or more apertures. The second lumen 406 may be covered at the distal end of the catheter shaft 402 (for example, by a separate cover, the wall of the catheter shaft 402, or the like).

Figure 5:
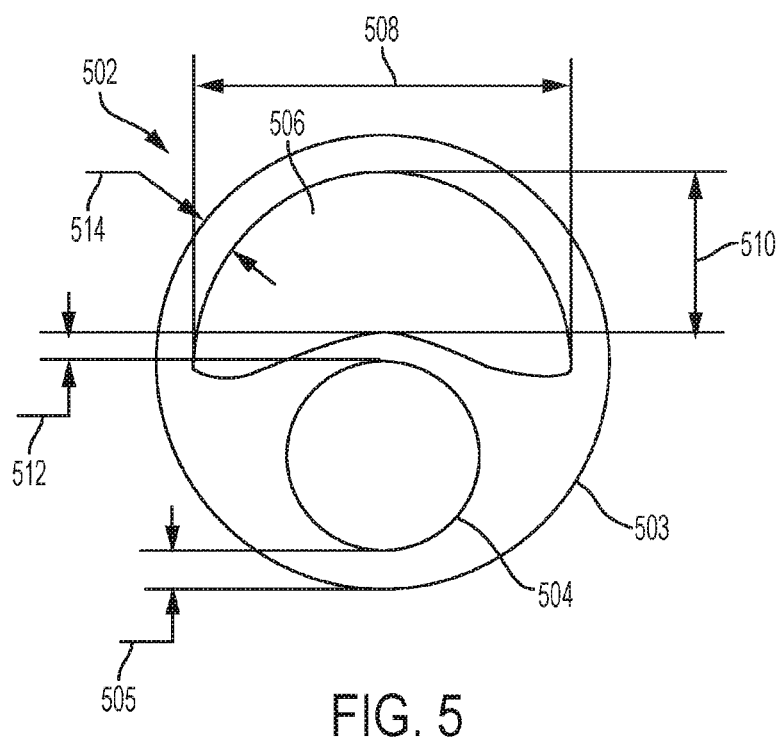
FIG. 5 is a cross-sectional view of another embodiment of a catheter shaft of the occlusion balloon device of FIG. 2.

FIG. 5 is a cross-sectional view of a second exemplary embodiment of a catheter shaft 502 that may be used as the catheter shaft 206 described above. The catheter shaft 502 may be formed of one or more elastomeric materials, such as polyurethane. For example, the catheter shaft 502 may be formed of Pellethane®, specifically 75D Pellethane which is available from The Lubrizol Corporation.

The catheter shaft 502 may have an outer diameter 503 of about 2.3 mm (that is, 2.3 mm±0.038 mm). The catheter shaft 502 may have a length of about 110 cm (that is, 110 cm±0.3 cm).

The catheter shaft 502 includes a first lumen 504 that is adapted to receive a guidewire or an implanted cardiac lead to guide the occlusion balloon device 202 to a position proximate the perforation 108. The first lumen 504 is non-centrically disposed relative to the outer diameter 503 of the catheter shaft 502. The first lumen 504 may have circular cross section and have a diameter of about 0.94 mm (that is, 0.94 mm±0.025 mm). A minimum wall thickness 505 between the first lumen 504 and the outer diameter 503 may be about 0.1 mm (that is, 0.1 mm±0.025 mm).

The catheter shaft 502 also includes a second lumen 506 that is adapted to receive the inflation fluid from the connection hub 208 and deliver the inflation fluid to the balloon inflation chamber 304. The second lumen 506 is non-centrically disposed relative to the first lumen 504 and the outer diameter 503 of the catheter shaft 502. The second lumen 506 may have a non-circular cross-sectional shape, such as a crescent-like cross-sectional shape. The second lumen 506 may have a width 508 of about 2.0 mm (that is, 2.0 mm±0.025 mm). The second lumen 506 may have a height 510 in a plane that bisects the catheter shaft 502 of about 0.94 mm (that is, 0.94 mm±0.025 mm). A minimum wall thickness 512 between the second lumen 506 and the first lumen 504 may be about 0.1 mm (that is, 0.1 mm±0.025 mm). A minimum wall thickness 514 between the second lumen 506 and the outer diameter 503 may be about 0.15 mm (that is, 0.15 mm±0.025 mm). Having a two or more of the following allows the clinician to quickly inflate the inflation chamber 304 of inflatable balloon 204 with the inflation fluid: a crescent-like cross-sectional shape for the second lumen 506; a wall thickness 505 between the first lumen 504 and the outer diameter 503 about 0.15 mm; a wall thickness 514 between the second lumen 506 and the outer diameter 503 about 0.1 mm; and wall thickness 512 between the second lumen 506 and the first lumen 504 about 0.1 mm.

The catheter shaft 502 also includes one or more apertures (not shown) that couple the second lumen 506 to the exterior of the catheter shaft 502 and the balloon inflation chamber 304. That is, the second lumen 506 delivers the inflation fluid to the inflatable balloon 204 via one or more apertures. The second lumen 506 may be covered at the distal end of the catheter shaft 502 (for example, by a separate cover, the wall of the catheter shaft 502, or the like).

In some embodiments, the dimensions and material properties of the inflatable balloon 204, the catheter shaft 402, and the catheter shaft 502 facilitate using the occlusion balloon device 202 with relatively small guidewires and introducer sheaths and relatively quickly delivering the inflation fluid to the inflatable balloon 204 (for example, in 15 seconds or less). Furthermore, the occlusion balloon device 202 has sufficient strength for entering a subject's vasculature and occluding a vascular perforation.

Figure 6B:
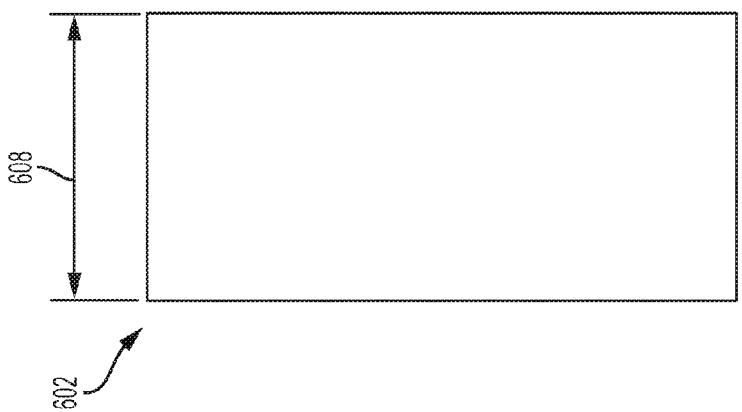
FIG. 6B is a side view of the radiopaque marker band of FIG. 6A.
Figure 6A:
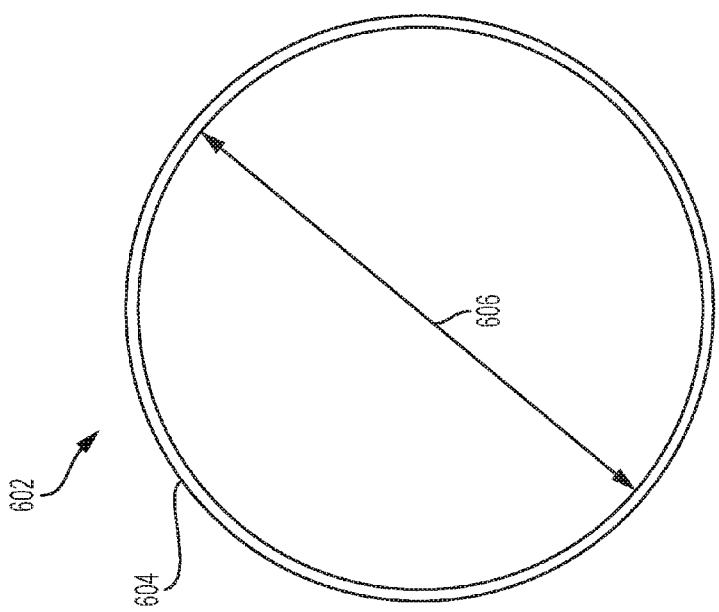
FIG. 6A is a front view of a radiopaque marker band of the occlusion balloon device of FIG. 2.
Figure 7A:
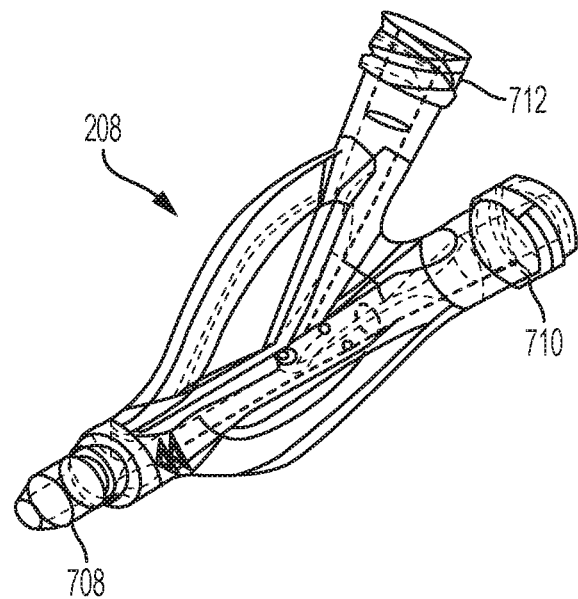
FIG. 7A is a perspective view of a connection hub of the of the occlusion balloon device of FIG. 2.
Figure 7B:
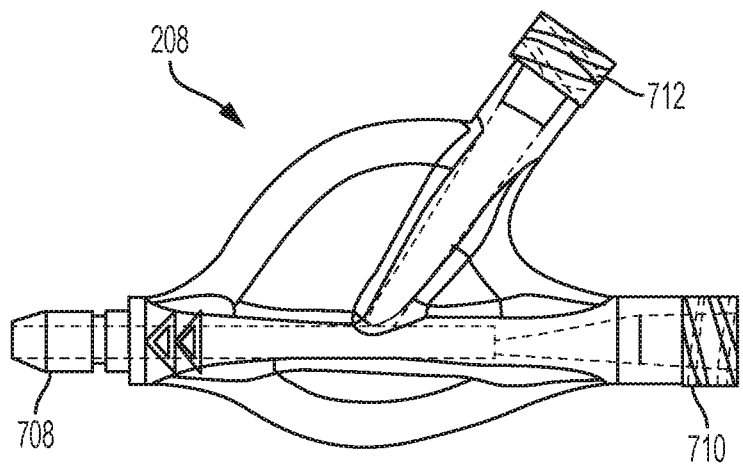
FIG. 7B is a side view of the connection hub of FIG. 7A.
Figure 7C:
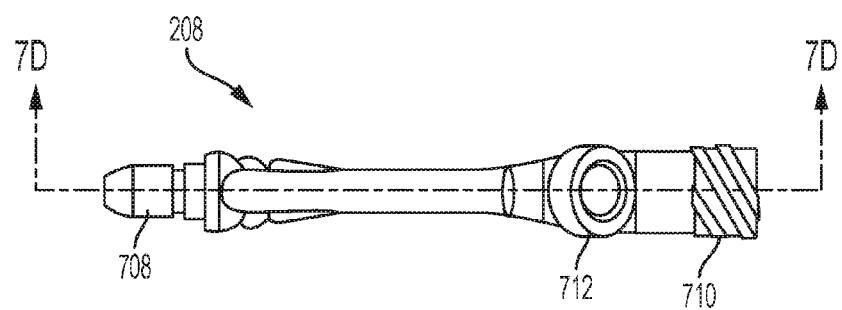
FIG. 7C is a top view of the connection hub of FIG. 7A.
Figure 7D:
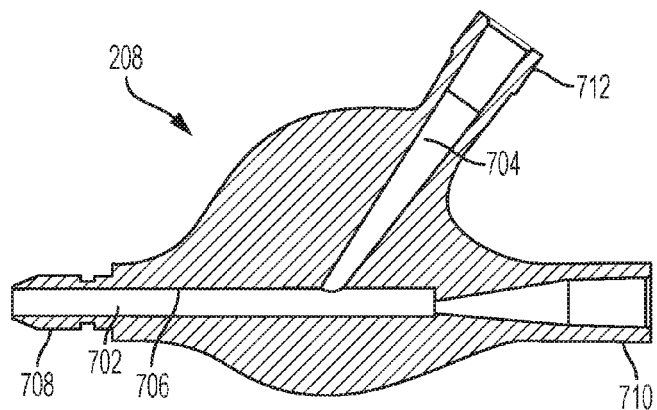
FIG. 7D is a side sectional view of the connection hub along line 7D-7D of FIG. 7C.

FIGS. 6A and 6B are views of a radiopaque marker band 602 that may be used as the radiopaque markers 212 described above. The radiopaque marker band 602 may be formed of one or more radiopaque materials, such a mixture of about 90 percent platinum (that is, 90 percent±1 percent) and 10 percent iridium (that is, 10 percent±1 percent). The radiopaque marker band 602 may have an open-ended cylindrical shape that is adapted to extend around the circumference of the catheter shaft 206. The radiopaque marker band 602 may have an outer diameter 604 in a range of about 2.3 mm (that is, 2.3 mm±0.01 mm) to about 2.5 mm (that is, 2.5 mm±0.01 mm). The radiopaque marker band 602 may have an inner diameter 606 of about 2.2 mm (that is, 2.2 mm±0.01 mm) to about 2.4 mm (that is, 2.4 mm±0.01 mm). The radiopaque marker band 602 may have a length 608 of about 1.2 mm (that is, 1.2 mm±0.05 mm).

FIGS. 7A-7D are views of the connection hub 208. The connection hub 208 may be formed of one or more polymers, such as Polycarbonate, specifically Makrolon®, which is available from Bayer MaterialScience of Darmstadt, Germany. The connection hub 208 includes a bifurcate lumen, which in turn includes a main lumen 702 and a branch lumen 704 (see FIG. 7D). The branch lumen 704 extends from the main lumen 702 at an acute angle. The main lumen 702 may have an inner diameter 706 in a range of about 2.2 mm (that is, 2.2 mm±0.025 mm) to about 2.4 mm (that is, 2.4 mm±0.025 mm). The main lumen 704 couples to a first port 708 on a distal side of the connection hub 208. The first port 708 couples to the catheter shaft 206 and the strain relief 210. The main lumen 704 couples to a second port 710 on a proximal side of the connection hub 208. The second port 710, which may be, for example, ISO 594-complaint Luer connector, is adapted to receive a guidewire and/or couple to an inflation fluid source, such as a syringe. The branch lumen 706 couples to a third port 712 on the proximal side of the connection hub 208. The third port 712, which may be, for example, ISO 594-complaint Luer connector, is adapted to receive a guidewire and/or couple to an inflation fluid source, such as a syringe.

Figure 8A:
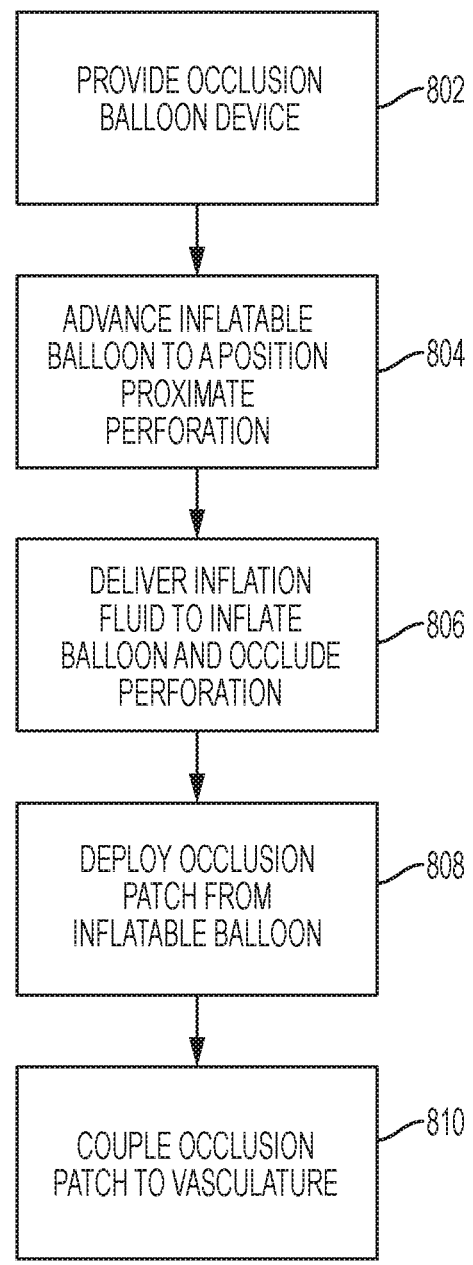
FIG. 8A illustrates an exemplary method for occluding a perforation in a blood vessel according to embodiments of the present disclosure.
Figure 8B:
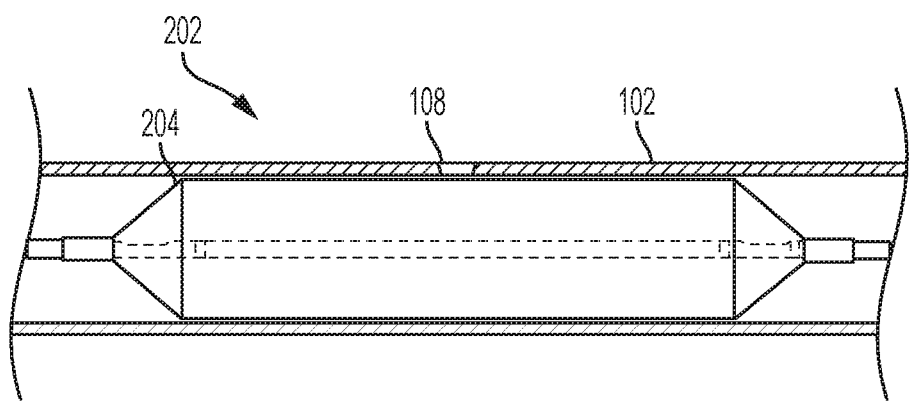
FIG. 8B illustrates an exemplary occlusion balloon occluding a perforation in a blood vessel according to embodiments of the present disclosure.

FIG. 8A illustrates an exemplary method for occluding a perforation in a blood vessel according to embodiments of the present disclosure. The method begins at block 802 by providing an occlusion balloon device, such as the occlusion balloon device 202 of depicted in FIGS. 2-7 described above or any of the occlusion balloon devices, such as the occlusion balloon devices depicted in FIGS. 9-22, described below. For simplicity, this paragraph only refers to the features of the occlusion balloon device 202. At block 804, the catheter shaft 206 and the inflatable balloon 204 are advanced in the blood vessel until the inflatable balloon 204 is positioned proximate a perforation, as depicted in FIG. 8B. Continuing to refer to FIG. 8B, the inflatable balloon 204 is in an inflated state adjacent and, therefore, proximate the perforation 108. Although the inflatable balloon 204 in depicted in FIG. 8B as adjacent and covering the entire perforation 108, the occlusion balloon device 202 could be placed in a position within the blood vessel 102 such that the inflatable balloon 204 covers only a portion of the perforation 108 or the inflatable balloon 204 does not cover any portion of the perforation 108 but is disposed very near the perforation 108 in a location that is upstream of the blood flow within the blood vessel, thereby allowing the inflatable balloon 204 to occlude the blood flow from flowing through the perforation 108.

Referring again to FIG. 8A, in some embodiments, the first lumen 404 of the catheter shaft 206 receives a guidewire or an implanted cardiac lead, and the catheter shaft 206 and the inflatable balloon 204 are advanced along the guidewire or the implanted cardiac lead. In some embodiments, the catheter shaft 206 may be advanced to the perforation via a femoral vein (for example, the right femoral vein) by using a femoral introducer sheath (for example, a 12F femoral introducer sheath). In some embodiments, the catheter shaft 206 may be advanced until the proximal radiopaque marker 212 is located at the junction of the superior vena cava and right atrium. At block 806, an inflation fluid (for example, saline and contrast solution as described above) is delivered to the inflatable balloon 204 via the second lumen 406 of the catheter shaft 206 to inflate the inflation balloon 204 and thereby occlude the perforation. In some embodiments, a 60 ml (cc) syringe delivers the inflation fluid to the inflation balloon 204 until the balloon 204 conforms to the vasculature. In some embodiments, the inflation fluid is delivered to the inflatable balloon 204 at a pressure in the range of about 2 atmospheres (that is, 2 atmospheres±10 percent) to about 3 atmospheres (that is, 3 atmospheres±10 percent). In some embodiments, contrast is injected via a superior venous access site to confirm proper inflation of the balloon 204 and occlusion of the perforation. In some embodiments, stabilization of the patient's hemodynamic and/or vital signs may be used to confirm occlusion of the perforation. In some embodiments and at block 808, the method may optionally include deploying an occlusion patch (for example, the occlusion patch 1708 described below) from the inflatable balloon 204 over the vascular perforation to thereby occlude the perforation. And if the inflatable balloon 204 includes an occlusion patch, inflation of the balloon 204 causes deployment of the occlusion patch. Additionally, in some embodiments and at block 810, the method optionally includes coupling the occlusion patch to the vasculature to maintain the position of the patch within the vasculature. In some embodiments, coupling the occlusion patch to the vasculature includes activating one or more adhesives carried by the patch in any of the manners described below. In some embodiments, when occlusion is no longer needed, the balloon 204 may be deflated by applying suction to the second lumen 406 by using a 60 ml (cc) syringe. In some embodiments, deflation of the balloon 204 may be confirmed by using fluoroscopy.

Figure 9A:
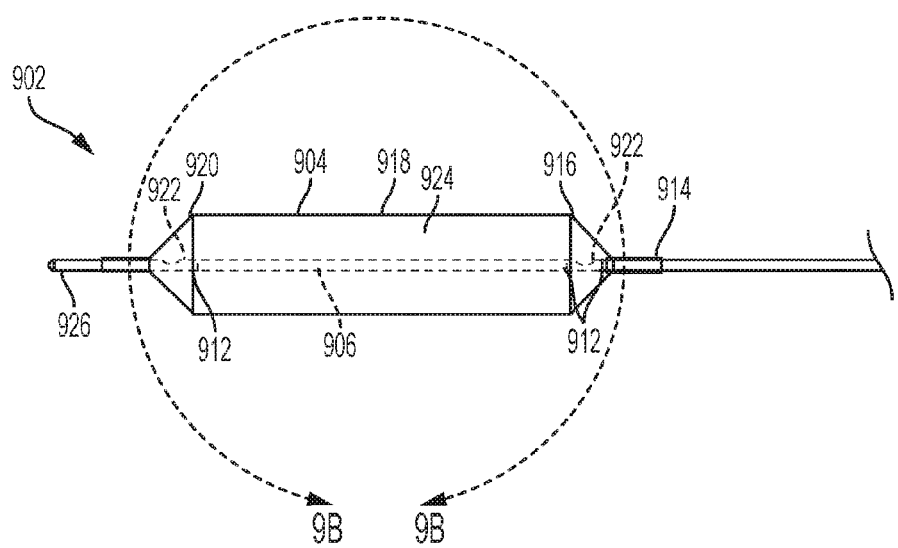
FIG. 9A is a partial side view of an occlusion balloon device according to embodiments of the present disclosure.
Figure 9B:
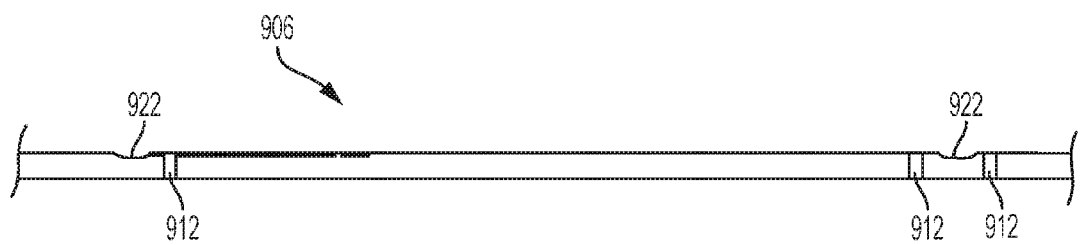
FIG. 9B is a detail view of a catheter shaft of the occlusion balloon device within line 9B-9B of FIG. 9A.

FIGS. 9A and 9B are side views of a distal portion of another exemplary occlusion balloon device 902 device according to embodiments of the present disclosure. The occlusion balloon device 902 generally includes an inflatable balloon 904, which may be similar to the balloons described above. The inflatable balloon 904 is carried at a distal portion of a catheter shaft 906. The occlusion balloon device 902 also includes a connection hub (not shown), which may be similar to the connection hubs described above. The connection hub is carried at a proximal portion of the catheter shaft 906. The connection hub and the catheter shaft 906 may carry a distally-tapering strain relief (not shown), which may be similar to the strain reliefs described above, at an interface therebetween. The catheter shaft 906 may also carry one or more radiopaque markers 912 such that the position of the occlusion balloon device 902 may be determined via medical imaging (for example, via fluoroscopy). The catheter shaft 906 may carry, for example, three radiopaque markers 912 as shown in FIGS. 9A and 9B. A first radiopaque marker 912 may be axially aligned with an intersection of a proximal neck 914 of the balloon 904 and a proximal tapered portion 916 of the balloon 904. A second radiopaque marker 912 may be axially aligned with the intersection of the proximal tapered portion 916 and a working portion 918 of the balloon 904. A third radiopaque marker 912 may be axially aligned with the intersection of the working portion 918 and a distal tapered portion 920 of the balloon 904.

The inflatable balloons of the present disclosure can be treated or coated with a variety of pharmaceutical and biological agents to assist in the treatment of the perforation site. In some embodiments, the inflatable balloons of the present disclosure can be coated with a hemostatic composition to reduce the rate of blood flow loss and allow more time for planning and initiating surgical repair of the perforation site. Generally, the hemostatic composition includes one or more hemostatic blood clotting agents (also referred to as hemostatic agents or clotting agents). Suitable clotting agents are present in effective amounts in the hemostatic composition such that they can stimulate or facilitate hemostasis. Suitable clotting agents include, but are not limited to: thrombin, or any naturally-occurring or synthetic agent that converts fibrinogen to fibrin; calcium, sodium, magnesium or other chemical ions that stimulate hemostasis; protamine sulfate; an epsilon amino caproic acid, fibrinogen, chitin, and the like. Hemostatic agents that can be used as part of the hemostatic compositions of the present disclosure also include, but are not limited to, fibrin-based agents such as fibrin sealant (also referred to as fibrin glue), gelatin matrix thrombin, gelatin sponge, oxidized cellulose, collagen sponge, collagen fleece, recombinant factor VIIa, and the like.

In some embodiments, it is also advantageous to include in the hemostatic compositions one or more agents having cell or tissue adhesion properties, including but not limited to, polyethylene glycol, cyanoacrylate, fibronectin, von Willebrand factor, protein Z and the like. Agents having cell or tissue adhesion properties can further reduce the rate of blood flow loss from a vascular perforation as well as promote healing of the perforation wound site. It may also be advantageous to include in the hemostatic compositions one or more coating agents, including but not limited to, a lipophilic antioxidant, such as nordihydroguaiaretic acid, resveratrol, propyl gallate and the like, with or without the addition of a biocompatible polymer, to stabilize the composition and/or prevent premature loss of the composition as the balloon travels through the vasculature to the perforation site.

Other components of the hemostatic composition can include hormonal agents, such as growth factors to promote wound healing and other therapeutic agents. In some embodiments, the hemostatic composition includes a wound-sealant composition and/or a cross-bridging binding agent of silica nanoparticles having potential reactive surface hydroxyl groups and possibly additional components including, for example, a fluid removal agent, a dehydration agent, an adhesive clumping agent, a swelling agent, a drug delivery vehicle such as a nanoparticle or microparticle, a clot enhancing composition, an activator or accelerator and the like. In other embodiments, the hemostatic composition can include prophylactic antibiotics and bactericidal agents such as penicillins, penicillin combinations, sulfonamides, lincosamides, carbapenems, tetracyclines, aminoglycosides, as well as other suitable antibiotic compositions and combinations thereof. The hemostatic composition of the present disclosure can also contain suitable adjuvants and excipients including preservative agents, wetting agents, emulsifying agents and dispersing agents, additional antibiotics alone or in combination with antifungal agents, for example, parabens, chlorobutanol, phenol, sorbic acid, and the like. It is also possible to include osmoregulation agents such as sugars, sodium chloride and the like. Additionally, agents for delaying absorption, such as aluminum monostearate and gelatin, can also be included in the hemostatic composition. As one of ordinary skill in the art would readily recognize based on the present disclosure, the hemostatic compositions can be formulated to be a powder, spray, aerosol, foam or gel that can be directly applied to the perforation site.

The hemostatic compositions of the present disclosure can be delivered to the tissues of the perforation site in various manners. For example, the hemostatic compositions can be applied to the outside periphery of an inflatable balloon positioned at the distal end of a catheter, such that when the balloon is inflated to occlude the perforation, the hemostatic composition is brought into contact with the tissue of the perforation site. Once delivered to the tissue of the perforation site, the different components of the hemostatic composition can exert their biological effects, such as promoting blood clotting and/or cell and tissue adhesion, in order to reduce the rate of blood flow loss and to promote healing of the perforation site. In some embodiments, the composition can be applied to the folds of inflatable balloon (in its uninflated state) such that the composition is protected from premature loss as the distal end of the catheter is being positioned in the vasculature. Upon deployment of the balloon, the composition is exposed and can be delivered to the tissue of the perforation site.

In other embodiments, devices and mechanisms can be included in the distal end of the catheter, adjacent to the balloon, to facilitate the expulsion of the composition to the tissue of the perforation site. For example, one or more optical fibers can be used to deliver a pulse of light energy to liquid media (e.g., contrast media) contained within an inflatable balloon in order to create a shock wave (e.g., cavitation of the liquid media) that propagates radially and delivers the composition to the tissue of the perforation site. Other means for delivering the hemostatic composition to the tissue of the perforation site can also be used, as would be recognized by one of ordinary skill in the art based on the present disclosure.

The catheter shaft 906 may include first and second lumens (not shown) that are similar to the first and second lumens, respectively, described above. The catheter shaft 906 also includes one or more apertures 922 that couple the second lumen to the exterior of the catheter shaft 906 and the balloon inflation chamber 924. That is, the second lumen delivers the inflation fluid to the inflatable balloon 904 via one or more apertures 922. The catheter shaft 906 may include, for example, two apertures 922 as shown in FIGS. 9A and 9B. A first aperture 922 may be axially aligned with the proximal tapered portion 916 of the balloon 904. A second aperture 922 may be axially aligned with the distal tapered portion 920 of the balloon 904.

A distal end of the catheter shaft 906 carries a distal tip 926 that covers the second lumen of the catheter shaft 906. The distal tip 926 includes an opening (not shown) that is aligned with the first lumen of the catheter shaft 906. Together with the first lumen, the opening is adapted to receive a guidewire or an implanted cardiac lead. The distal tip 926 may be formed of one or more elastomeric materials, such as polyurethane. For example, the distal tip 926 may be formed of Pellethane®, specifically 65D Pellethane®, which is available from The Lubrizol Corporation.

FIG. 10 is a side view of another exemplary occlusion balloon device 1002 device according to embodiments of the present disclosure. The occlusion balloon device 1002 generally includes an inflatable balloon 1004 that is carried at a distal portion of a catheter shaft 1006. The occlusion balloon device 1002 also includes a connection hub 1008 that is carried at a proximal portion of the catheter shaft 1006. The connection hub 1008 and the catheter shaft 1006 may carry a distally-tapering strain relief 1010 at an interface therebetween. The catheter shaft 1006 may also carry one or more radiopaque markers 1012 such that the position of the occlusion balloon device 1002 may be determined via medical imaging (for example, via fluoroscopy). The catheter shaft 1006 may carry, for example, three radiopaque markers 1012 as shown in FIG. 10. A first radiopaque marker 1012 may be axially aligned with a proximal portion of the inflatable balloon 1004, a second radiopaque marker 1012 may be axially aligned with an intermediate portion of the inflatable balloon 1004, and a third radiopaque marker 1012 may be axially aligned with a distal portion of the inflatable balloon 1004.

FIGS. 11A and 11B are a partial longitudinal section view and a front view of the inflatable balloon 1004 of the occlusion balloon device 1002 of FIG. 10, respectively, wherein the inflatable balloon 1004 is depicted in an inflated state. The inflatable balloon 1004 may include a wall 1102, an inflation chamber 1104, a proximal neck 1106 having a length 1110, a distal neck 1124 having a length 1128, a working portion 1116 having a length 1120, a proximal tapered portion 1112 disposed between the proximal neck 1106 and the working portion 1116, and a distal tapered portion 1122 disposed between the distal neck 1124 and the working portion 1116.

The wall 1102 of the inflatable balloon 1004 defines the inflation chamber 1104. The inflation chamber 1104 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the occlusion balloon device 1002 into the vasculature, positioning the inflatable balloon 1004 adjacent the perforation 108 and inflating the inflatable balloon, the inflatable balloon 1004 facilitates occlusion of the perforation 108.

In some embodiments, the inflatable balloon 1004 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 1004 may be formed of one or more elastomeric materials, such as polyurethane. For example, the inflatable balloon 1004 may be formed of Pellethane®, specifically 80AE Pellethane®, which is available from The Lubrizol Corporation. The inflatable balloon 1004 may have a Shore A durometer of about 85 A (that is, 85A±4 A).

The proximal neck 1106 engages the catheter shaft 1006 via one or more adhesives, a compression fit, or the like. The proximal neck 1106 may have an inner diameter 1108 of about 2.5 mm (that is, 2.5 mm±0.07 mm). The proximal neck 1106 may have a length 1110 of about 10 mm (that is, 10 mm±1 mm). The proximal neck 1106 may have a wall thickness of about 0.24 mm (that is, 0.24 mm±0.01 mm).

Distal to the proximal neck 1106, the proximal neck 1106 couples to the proximal tapered portion 1112. The proximal tapered portion 1112 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1004 is inflated, the proximal tapered portion 1112 may be disposed at an angle 1113 of about 35 degrees (that is, 35 degrees±10 degrees) relative to a longitudinal axis 1114 of the inflatable balloon 1004.

Distal to the proximal tapered portion 1112, the proximal tapered portion 1112 couples to the working portion 1116. The working portion 1116, when the inflatable balloon 1004 is appropriately positioned and inflated, occludes the perforation 108. The working portion 1116 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The working portion 1116 may have a length 1120 of about 115 mm (that is, 115 mm±3 mm) to about 65 mm (that is, 65 mm±3 mm).

The working portion 1116 tapers inwardly from a first outer diameter 1130 (at the interface with the proximal tapered portion 1112) to a second outer diameter 1132 (at the interface with the distal tapered portion 1122). When inflated, the first outer diameter 1130 may be greater than about 35 mm (that is, 35 mm±2 mm), for example between about 35 mm (that is, 35 mm±2 mm) and about 50 mm (that is, 50 mm±2 mm) and possibly further between about 35 mm (that is, 35 mm±2 mm) and about 45 mm (that is, 45 mm±2 mm). When inflated, the second outer diameter 1132 may be greater than about 16 mm (that is, 16 mm±2 mm), for example between about 16 mm (that is, 16 mm±2 mm) and about 30 mm (that is, 30 mm±2 mm) and possibly further between about 16 mm (that is, 16 mm±2 mm) and about 25 mm (that is, 25 mm±2 mm).

The ratio of the length 1120 of the working portion 1116 to the first outer diameter 1130 of the inflatable balloon 1004 in when inflated is, therefore, about 1.3:1 to about 3.3:1, and the ratio of the length 1120 of the working portion 1116 to the second outer diameter 1132 of the inflatable balloon 1004 in when inflated is, therefore, about 2.2:1 to about 7.2:1. Having these ratios with a relatively long working length provides a balloon that is particularly suitable for occluding perforations at or between the right innominate vein and the top portion of the right atrial chamber. That is, the distal portion of the working portion 1116 is particularly suitable for occluding perforations in the right innominate vein and the proximal portion of the working portion 1116 is particularly suitable for occluding perforations at the top portion of the atrial chamber. More generally, inflating the working portion 1116 to the diameters described above increases the likelihood that the working portion 1116 will be about the same diameter or slightly larger than the diameter of the blood vessel 102 at the perforation 108. Inflating the working portion 1116 to be about the same diameter or slightly larger than the diameter of the blood vessel 102 at the perforation 108 increases the likelihood that the inflatable balloon 1004 will block the perforation 108 without increasing its size.

In some embodiments and as shown in FIGS. 11A and 11B, the working portion may taper inwardly from the first outer diameter 1130 to the second outer diameter 1132 at a constant slope. Stated another way, the working portion 1116 may have a frusto-conical shape. In some embodiments, the working portion may taper inwardly from the first outer diameter 1130 to the second outer diameter 1132 at a non-constant slope.

Again, the inflatable balloon 1004 may be formed of one or more elastomeric materials, such as polyurethane. To inflate the inflatable balloon 1004 to the range of diameters referenced above, it may also be desirable to inflate the inflatable balloon 1004 with an inflation fluid to a pressure within the balloon inflation chamber 1104 from about 0 psi to about 3 psi. The amount of inflation fluid used to inflate the inflatable balloon 1004 to such a pressure and/or at the desired diameter is about 20 ml (cc) to about 60 ml (cc).

Distal to the working portion 1116, the working portion 1116 couples to the distal tapered portion 1122. The distal tapered portion 1122 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1004 is inflated, the distal tapered portion 1122 may be disposed at an angle 1123 of about 30 degrees (that is, 30 degrees±10 degrees) relative to the longitudinal axis 1114.

The distal neck 1124 engages the catheter shaft 1006 via one or more adhesives, a compression fit, or the like. The distal neck 1124 may have an inner diameter 1126 of about 2.5 mm (that is, 2.5 mm±0.07 mm). The distal neck 1124 may have a length 1128 of about 10 mm (that is, 10 mm±1 mm). The distal neck 1124 may have a wall thickness of about 0.24 mm (that is, 0.24 mm±0.01 mm).

The catheter shaft 1006, connection hub 1008, strain relief 1010, and the radiopaque marker(s) 1012 may be similar to the catheter shafts, connection hubs, strain reliefs, and the radiopaque markers, respectively, described above.

Figure 12A:
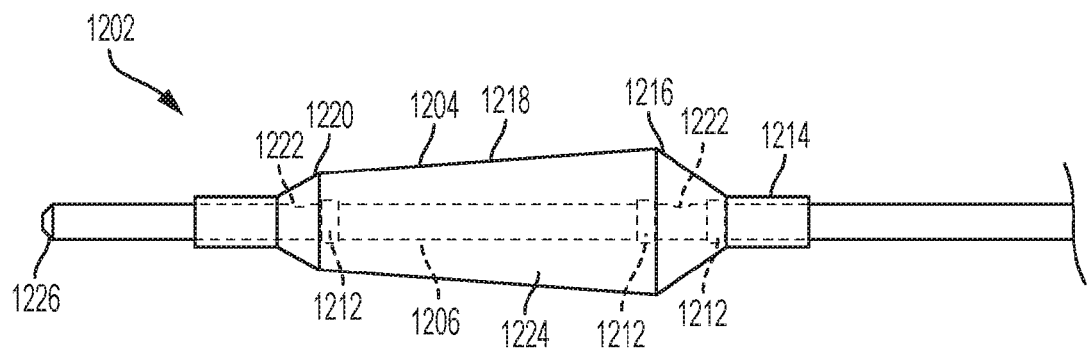
FIG. 12A is a partial side view of an occlusion balloon device according to embodiments of the present disclosure.
Figure 12B:
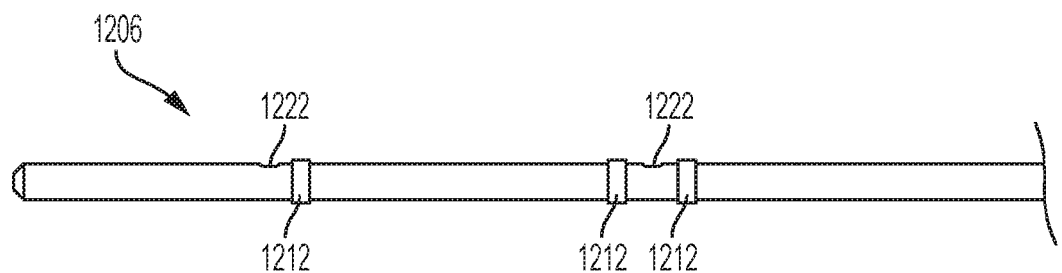
FIG. 12B is a detail view of a catheter shaft of the occlusion balloon device within line 12B-12B of FIG. 12A.

FIGS. 12A and 12B are side views of a distal portion of another exemplary occlusion balloon device 1202 device according to embodiments of the present disclosure. The occlusion balloon device 1202 generally includes an inflatable balloon 1204, which may be similar to the balloon 1004 described above. The inflatable balloon 1204 is carried at a distal portion of a catheter shaft 1206. The occlusion balloon device 1202 also includes a connection hub (not shown), which may be similar to the connection hubs described above. The connection hub is carried at a proximal portion of the catheter shaft 1206. The connection hub and the catheter shaft 1206 may carry a distally-tapering strain relief (not shown), which may be similar to the strain reliefs described above, at an interface therebetween. The catheter shaft 1206 may also carry one or more radiopaque markers 1212 such that the position of the occlusion balloon device 1202 may be determined via medical imaging (for example, via fluoroscopy). The catheter shaft 1206 may carry, for example, three radiopaque markers 1212 as shown in FIGS. 12A and 12B. A first radiopaque marker 1212 may be axially aligned with an intersection of a proximal neck 1214 of the balloon 1204 and a proximal tapered portion 1216 of the balloon 1204. A second radiopaque marker 1212 may be axially aligned with the intersection of the proximal tapered portion 1216 and a working portion 1218 of the balloon 1204. A third radiopaque marker 1212 may be axially aligned with the intersection of the working portion 1218 and a distal tapered portion 1220 of the balloon 1204.

The catheter shaft 1206 may include first and second lumens (not shown) that are similar to the first and second lumens, respectively, described above. The catheter shaft 1206 also includes one or more apertures 1222 that couple the second lumen to the exterior of the catheter shaft 1206 and the balloon inflation chamber 1224. That is, the second lumen delivers the inflation fluid to the inflatable balloon 1204 via one or more apertures 1222. The catheter shaft 1206 may include, for example, two apertures 1222 as shown in FIGS. 12A and 12B. A first aperture 1222 may be axially aligned with the proximal tapered portion 1216 of the balloon 1204. A second aperture 1222 may be axially aligned with the distal tapered portion 1220 of the balloon 1204.

A distal end of the catheter shaft 1206 carries a distal tip 1226 that covers the second lumen of the catheter shaft 1206. The distal tip 1226 includes an opening (not shown) that is aligned with the first lumen of the catheter shaft 1206. Together with the first lumen, the opening is adapted to receive a guidewire or an implanted cardiac lead. The distal tip 1226 may be formed of one or more elastomeric materials, such as polyurethane. For example, the distal tip 1226 may be formed of Pellethane®, specifically 65D Pellethane®, which is available from The Lubrizol Corporation.

A number of variations and modifications to the occlusion balloon devices 1002 and 1202 may be used. For example, if the catheters 1002 or 1202 is to be inserted using a non-femoral vein approach (for example, a jugular vein approach), the working portion may taper inwardly proceeding in a proximal direction.

FIG. 13 is a side view of another exemplary occlusion balloon device 1302 device according to embodiments of the present disclosure. The occlusion balloon device 1302 generally includes an inflatable balloon 1304 that is carried at a distal portion of a catheter shaft 1306. The occlusion balloon device 1302 also includes a connection hub 1308 that is carried at a proximal portion of the catheter shaft 1306. The connection hub 1308 and the catheter shaft 1306 may carry a distally-tapering strain relief 1310 at an interface therebetween. The catheter shaft 1306 may also carry one or more radiopaque markers 1312 such that the position of the occlusion balloon device 1302 may be determined via medical imaging (for example, via fluoroscopy). The catheter shaft 1306 may carry, for example, three radiopaque markers 1312 as shown in FIG. 13. A first radiopaque marker 1312 may be axially aligned with a proximal portion of the inflatable balloon 1304, a second radiopaque marker 1312 may be axially aligned with an intermediate portion of the inflatable balloon 1304, and a third radiopaque marker 1312 may be axially aligned with a distal portion of the inflatable balloon 1304.

FIGS. 14A and 14B are a partial longitudinal section view and a front view of the inflatable balloon 1304 of the occlusion balloon device 1302 of FIG. 13, respectively, wherein the inflatable balloon 1304 is depicted in an inflated state. The inflatable balloon 1304 may include a wall 1402, an inflation chamber 1404, a proximal neck 1406 having a length 1410, a distal neck 1424 having a length 1428, a multiple-diameter working portion 1416 having a length 1420, a proximal tapered portion 1412 disposed between the proximal neck 1406 and the working portion 1416, and a distal tapered portion 1422 disposed between the distal neck 1424 and the working portion 1416.

The wall 1402 of the inflatable balloon 1304 defines the inflation chamber 1404. The inflation chamber 1404 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the occlusion balloon device 1302 into the vasculature, positioning the inflatable balloon 1304 adjacent the perforation 108 and inflating the inflatable balloon, the inflatable balloon 1304 facilitates occlusion of the perforation 108.

In some embodiments, the inflatable balloon 1304 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 1304 may be formed of one or more elastomeric materials, such as polyurethane. For example, the inflatable balloon 1304 may be formed of Pellethane®, specifically 80AE Pellethane®, which is available from The Lubrizol Corporation. The inflatable balloon 1304 may have a Shore A durometer of about 85 A (that is, 85A±4 A).

The proximal neck 1406 engages the catheter shaft 1306 via one or more adhesives, a compression fit, or the like. The proximal neck 1406 may have an inner diameter 1408 of about 2.5 mm (that is, 2.5 mm±0.07 mm). The proximal neck 1406 may have a length 1410 of about 10 mm (that is, 10 mm±1 mm). The proximal neck 1406 may have a wall thickness of about 0.24 mm (that is, 0.24 mm±0.01 mm).

Distal to the proximal neck 1406, the proximal neck 1406 couples to the proximal tapered portion 1412. The proximal tapered portion 1412 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1304 is inflated, the proximal tapered portion 1412 may be disposed at an angle 1413 of about 60 degrees (that is, 60 degrees±10 degrees) relative to a longitudinal axis 1414 of the inflatable balloon 1304.

Distal to the proximal tapered portion 1412, the proximal tapered portion 1412 couples to the multiple-diameter working portion 1416. The working portion 1416, when the inflatable balloon 1304 is appropriately positioned and inflated, occludes the perforation 108. The working portion 1416 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The working portion 1416 may have an overall length 1420 of about 125 mm (that is, 125 mm±3 mm) to about 85 mm (that is, 85 mm±3 mm).

The working portion 1416 includes a plurality of sections that each have a different outer diameter. For example and as shown in the figures, the working portion 1416 may include a proximal or first section 1432 having a first outer diameter 1434, an intermediate or second section 1436 having a second outer diameter 1438, and a distal or third section 1440 having a third outer diameter 1442. The first outer diameter 1434 may be greater than the second outer diameter 1438 and the second outer diameter 1438 may be greater than the third outer diameter 1442.

The first section 1432 may have a length 1444 greater than about 18 mm (that is, 18 mm±2 mm), for example between about 18 mm (that is, 18 mm±2 mm) and about 25 mm (that is, 25 mm±2 mm). When inflated, the first outer diameter 1434 may be between about 60 mm (that is, 60 mm±2 mm) and about 40 mm (that is, 40 mm±2 mm), and possibly about 50 mm (that is, 50 mm±2 mm).

Distal to the first section 1432, a first intermediate tapered portion 1446 couples the first section 1432 to the second section 1436. The first intermediate tapered portion 1446 may be disposed at an angle of about 45 degrees (that is, 45 degrees±10 degrees) relative to the longitudinal axis 1414 of the inflatable balloon 1304.

The second section 1436 may have a length 1448 greater than about 52 mm (that is, 52 mm±2 mm), for example between about 52 mm (that is, 52 mm±2 mm) and about 60 mm (that is, 60 mm±2 mm). When inflated, the second outer diameter 1438 may be between about 30 mm (that is, 30 mm±2 mm) and about 10 mm (that is, 10 mm±2 mm), and possibly about 20 mm (that is, 20 mm±2 mm).

Distal to the second section 1436, a second intermediate tapered portion 1450 couples the second section 1436 to the third section 1440. The second intermediate tapered portion 1450 may be disposed at an angle of about 45 degrees (that is, 45 degrees±10 degrees) relative to the longitudinal axis 1414 of the inflatable balloon 1304.

The third section 1440 may have a length 1452 between about 40 mm (that is, 40 mm±2 mm) and about 20 mm (that is, 20 mm±2 mm), and possibly about 30 mm (that is, 30 mm±2 mm). When inflated, the third outer diameter 1442 may be between about 26 mm (that is, 26 mm±2 mm) and about 6 mm (that is, 6 mm±2 mm), and possibly about 16 mm (that is, 16 mm±2 mm).

The ratio of the overall length 1420 of the working portion 1416 to the first outer diameter 1434 of the inflatable balloon 1304 in when inflated is, therefore, about 1.4:1 to about 3.1:1, ratio of the overall length 1420 of the working portion 1416 to the second outer diameter 1438 of the inflatable balloon 1304 in when inflated is, therefore, about 2.8:1 to about 12.5:1, and the ratio of the length 1420 of the working portion 1416 to the third outer diameter 1442 of the inflatable balloon 1304 in when inflated is, therefore, about 3.3:1 to about 20.8:1. Having these ratios with a relatively long working length provides a balloon that is particularly suitable for occluding perforations at or between the right innominate vein and the top portion of the right atrial chamber. That is, the third section 1440 of the working portion 1416 is particularly suitable for occluding perforations in the right innominate vein, the second section 1436 of the working portion 1416 is particularly suitable for occluding perforations in the superior vena cava, and the first section 1432 of the working portion 1416 is particularly suitable for occluding perforations at the top portion of the atrial chamber. More generally, inflating the working portion 1416 to the diameters described above increases the likelihood that the working portion 1416 will be about the same diameter or slightly larger than the diameter of the blood vessel 102 at the perforation 108. Inflating the working portion 1416 to be about the same diameter or slightly larger than the diameter of the blood vessel 102 at the perforation 108 increases the likelihood that the inflatable balloon 1304 will block the perforation 108 without increasing its size.

In some embodiments, the first section 1432 of the working portion 1416 inhibits blood flowing from the inferior vena cava from exiting through a perforation at the junction of the superior vena cava and the right atrium. That is, the first section 1432 of the working portion 1416 may act as a plug or baffle that redirects flow into the ventricle.

Again, the inflatable balloon 1304 may be formed of one or more elastomeric materials, such as polyurethane. To inflate the inflatable balloon 1304 to the range of diameters referenced above, it may also be desirable to inflate the inflatable balloon 1304 with an inflation fluid to a pressure within the balloon inflation chamber 1404 from about 0 psi to about 3 psi. The amount of inflation fluid used to inflate the inflatable balloon 1304 to such a pressure and/or at the desired diameter is about 20 ml (cc) to about 60 ml (cc).

Distal to the working portion 1416, the working portion 1416 couples to the distal tapered portion 1422. The distal tapered portion 1422 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1304 is inflated, the distal tapered portion 1422 may be disposed at an angle 1423 of about 45 degrees (that is, 45 degrees±10 degrees) relative to the longitudinal axis 1414.

The distal neck 1424 engages the catheter shaft 1306 via one or more adhesives, a compression fit, or the like. The distal neck 1424 may have an inner diameter 1426 of about 2.5 mm (that is, 2.5 mm±0.07 mm). The distal neck 1424 may have a length 1428 of about 10 mm (that is, 10 mm±1 mm). The distal neck 1424 may have a wall thickness of about 0.24 mm (that is, 0.24 mm±0.01 mm).

The catheter shaft 1306, connection hub 1308, strain relief 1310, and the radiopaque marker(s) 1312 may be similar to the catheter shafts, connection hubs, strain reliefs, and the radiopaque markers, respectively, described above.

Figure 15A:
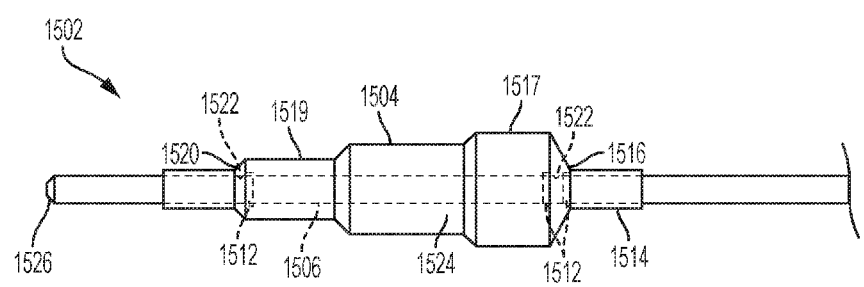
FIG. 15A is a partial side view of an occlusion balloon device according to embodiments of the present disclosure.
Figure 15B:
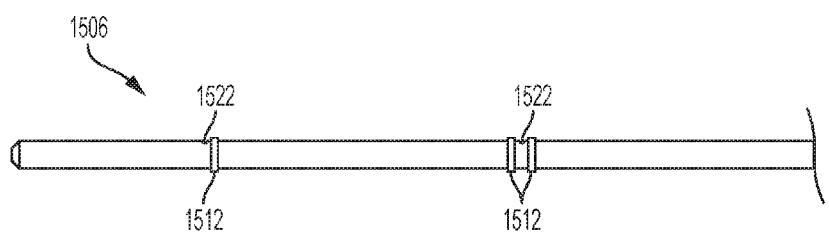
FIG. 15B is a detail view of a catheter shaft of the occlusion balloon device within line 15B-15B of FIG. 15A.

FIGS. 15A and 15B are side views of a distal portion of another exemplary occlusion balloon device 1502 device according to embodiments of the present disclosure. The occlusion balloon device 1502 generally includes an inflatable balloon 1504, which may be similar to the balloon 1304 described above. The inflatable balloon 1504 is carried at a distal portion of a catheter shaft 1506. The occlusion balloon device 1502 also includes a connection hub (not shown), which may be similar to the connection hubs described above. The connection hub is carried at a proximal portion of the catheter shaft 1506. The connection hub and the catheter shaft 1506 may carry a distally-tapering strain relief (not shown), which may be similar to the strain reliefs described above, at an interface therebetween. The catheter shaft 1506 may also carry one or more radiopaque markers 1512 such that the position of the occlusion balloon device 1502 may be determined via medical imaging (for example, via fluoroscopy). The catheter shaft 1506 may carry, for example, three radiopaque markers 1512 as shown in FIGS. 15A and 15B. A first radiopaque marker 1512 may be axially aligned with an intersection of a proximal neck 1514 of the balloon 1504 and a proximal tapered portion 1516 of the balloon 1504. A second radiopaque marker 1512 may be axially aligned with the intersection of the proximal tapered portion 1516 and a proximal section 1517 of a working portion of the balloon 1504. A third radiopaque marker 1512 may be axially aligned with the intersection of a distal section 1519 of the working portion and a distal tapered portion 1520 of the balloon 1504.

The catheter shaft 1506 may include first and second lumens (not shown) that are similar to the first and second lumens, respectively, described above. The catheter shaft 1506 also includes one or more apertures 1522 that couple the second lumen to the exterior of the catheter shaft 1506 and the balloon inflation chamber 1524. That is, the second lumen delivers the inflation fluid to the inflatable balloon 1504 via one or more apertures 1522. The catheter shaft 1506 may include, for example, two apertures 1522 as shown in FIGS. 15A and 15B. A first aperture 1522 may be axially aligned with the proximal tapered portion 1516 of the balloon 1504. A second aperture 1522 may be axially aligned with the distal tapered portion 1520 of the balloon 1504.

A distal end of the catheter shaft 1506 carries a distal tip 1526 that covers the second lumen of the catheter shaft 1506. The distal tip 1526 includes an opening (not shown) that is aligned with the first lumen of the catheter shaft 1506. Together with the first lumen, the opening is adapted to receive a guidewire or an implanted cardiac lead. The distal tip 1526 may be formed of one or more elastomeric materials, such as polyurethane. For example, the distal tip 1526 may be formed of Pellethane®, specifically 65D Pellethane®, which is available from The Lubrizol Corporation.

Figure 16A:
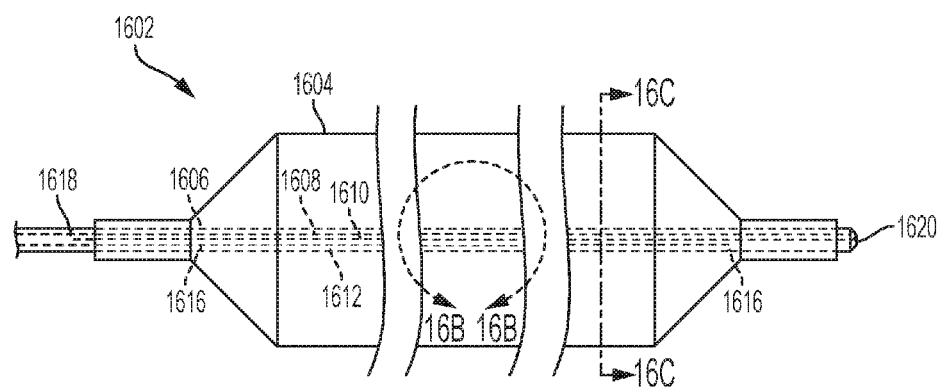
FIG. 16A is a side view of an occlusion balloon device according to embodiments of the present disclosure.
Figure 16B:
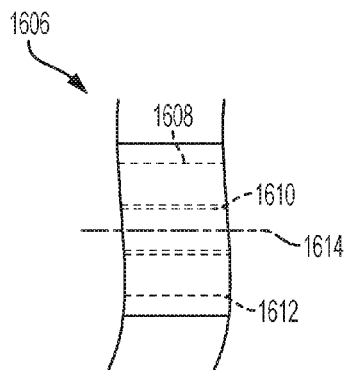
FIG. 16B is a detail view of a catheter shaft of the occlusion balloon device within line 16B-16B of FIG. 16A.
Figure 16C:
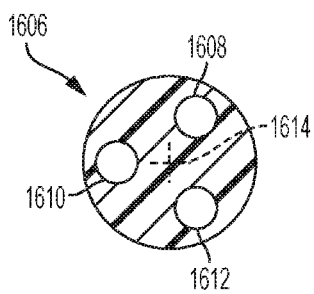
FIG. 16C is a cross-sectional view of the catheter shaft of the occlusion balloon device along line 16C-16C of FIG. 16A.

FIGS. 16A and 16B are views of a distal portion of another exemplary occlusion balloon device 1602 device according to embodiments of the present disclosure. The occlusion balloon device 1602 generally includes an inflatable balloon 1604, which may be similar to any of the balloons described herein. The inflatable balloon 1604 is carried at a distal portion of a catheter shaft 1606. The occlusion balloon device 1602 also includes a connection hub (not shown), which may be similar to the connection hubs described above. The connection hub is carried at a proximal portion of the catheter shaft 1606. The connection hub and the catheter shaft 1606 may carry a distally-tapering strain relief (not shown), which may be similar to the strain reliefs described above, at an interface therebetween.

The catheter shaft 1606 includes a first lumen 1608, a second lumen 1610, and a third lumen 1612. The lumens 1608, 1610, and 1612 may be disposed about the longitudinal axis 1614 of the catheter shaft 1606 at equal angles, although other arrangements are also contemplated. The first lumen 1604 is adapted to receive a guidewire or an implanted cardiac lead to guide the occlusion balloon device 1602 to a position proximate the perforation 108. The second lumen 1610 delivers inflation fluid to the inflatable balloon 1604 via one or more apertures 1616. The catheter shaft 1606 may include, for example, two apertures 1616 as shown in FIG. 16A. The third lumen 1612 acts as a blood perfusion lumen. That is, the third lumen 1612 facilitates passage of blood through the catheter shaft 1606 and from one end of the inflatable balloon 1604 to the other. The third lumen 1612 is coupled to a first aperture 1618 disposed proximally of the balloon device 1602 and a second aperture 1620 disposed distally of the balloon device 1602. The first aperture 1618 may be disposed on the side of the catheter shaft 1606. The second aperture 1620 may be disposed on the distal end of the catheter shaft 1606.

The catheter shaft 1606 may carry one or more radiopaque markers (not shown) in any of the manners described herein.

Figure 17B:
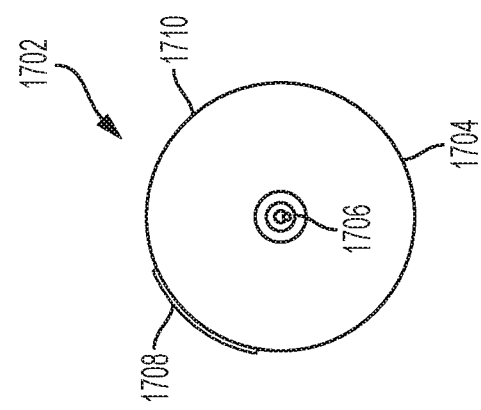
FIG. 17B is a front view of the occlusion balloon device of FIG. 17A.
Figure 17A:
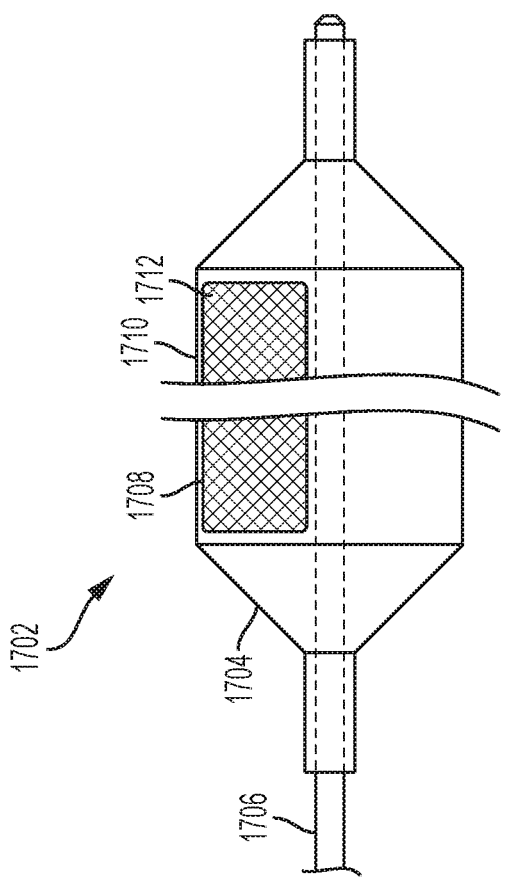
FIG. 17A is a side view of an occlusion balloon device according to embodiments of the present disclosure.

FIGS. 17A and 17B are views of a distal portion of another exemplary occlusion balloon device 1702 device according to embodiments of the present disclosure. The occlusion balloon device 1702 generally includes an inflatable balloon 1704, which may be similar to any of the balloons described herein. The inflatable balloon 1704 is carried at a distal portion of a catheter shaft 1706, which may be similar to any of the catheter shafts described herein. The occlusion balloon device 1702 also includes a connection hub (not shown), which may be similar to the connection hubs described above. The connection hub is carried at a proximal portion of the catheter shaft 1706. The connection hub and the catheter shaft 1706 may carry a distally-tapering strain relief (not shown), which may be similar to the strain reliefs described above, at an interface therebetween.

The occlusion balloon device 1702 also includes an occlusion patch 1708 that is detachably carried on the outer surface of the working portion 1710 of the inflatable balloon 1704. The inflatable balloon 1704 may deploy the occlusion patch 1708 (for example, by inflation of the balloon 1704) to position the patch 1708 over a vascular perforation and thereby occlude the perforation. In some embodiments, the occlusion patch 1708 may include one or more adhesives to maintain the position of the patch 1708 within the vasculature. The adhesive properties of the one or more adhesives may be activated in various manners, such as through the application of one or more of heat, pH, light, and the like. In some embodiments, the adhesives may be activated by the application of ultraviolet light. For example, adhesive compositions of the present disclosure may be activated as described in "A Blood-Resistant Surgical Glue for Minimally Invasive Repair of Vessels and Heart Defects," Lang et al., *Science Translational Medicine*, Vol. 6, Issue 218, Jan. 8, 2014; "A Light-Reflecting Balloon Catheter for Atraumatic Tissue Defect Repair," Roche et al., *Science Translational Medicine*, Vol. 7, Issue 306, Sep. 23, 2015; and WO 2015/175662, which are hereby incorporated herein by reference in their entirety for all that they teach and for all purposes.

In some embodiments, the adhesive may comprise adhesives currently used in clinical settings, including, but not limited to, cyanoacrylates, bovine serum albumin (BSA)-glutaraldehyde, fibrin sealants, gelatin matrix thrombin, gelatin sponge, oxidized cellulose, collagen sponge, collagen fleece, recombinant factor VIIa, and the like. In some embodiments, the adhesive may comprise hydrophobic functional groups, such as hexanoyl (Hx; C6), palmitoyl (Pam; C16), stearoyl (Ste; C18), and oleoyl (Ole; C18 unsaturated) groups, so as to resist being washed out or disengaged from their substrate in predominately aqueous environments (e.g., vascular tissue). Such adhesives include, but are not limited to, 10Ole-disuccinimidyl tartrate, 10Ste-disuccinimidyl, and variations and combinations thereof.

Adhesives may be combined with various other compounds to facilitate their attachment to the occlusion patch 1708. For example, adhesives may be combined with various compounds (e.g., solubilizing agents) that aid in the generation of a solution or mixture comprising the adhesive, which can be used to coat the occlusion patch 1708.

In some embodiments, a biodegradable and biocompatible hydrophobic polymer may be used as the adhesive. For example, the biodegradable and biocompatible hydrophobic polymer may be poly(glycerol sebacate acrylate) (PGSA), or variations and combinations thereof, which can be cross-linked using UV light. Ultraviolet light may be emitted from the distal end of an ultraviolet light-emitting catheter, which may be disposed within or outside of the inflatable balloon 1704, to activate the PGSA attached to the occlusion patch 1708. If the ultraviolet light-emitting catheter is disposed within the balloon 1704, the ultraviolet light-emitting catheter may be disposed (partially or entirely) within the portion of the catheter shaft 1706 that is within the balloon 1704 or the ultraviolet light-emitting catheter may be disposed between the catheter shaft 1706 and the interior side of the balloon 1704. The wall of the inflatable balloon 1704 may be translucent to facilitate transmission of the ultraviolet light from the ultraviolet light-emitting catheter to the occlusion patch 1708.

In some embodiments, the patch 1708 may be constructed of bovine pericardium, porcine small intestine submucosa, polyethylene terephthalate and Poly(glycerol sebacate urethane) (PGSU). Additionally, the patch 1708 may include a scaffold structure 1712 to facilitate tissue growth therein. In some embodiments, the patch 1708 includes stem cells to facilitate bioabsorption of the patch 1708. In some embodiments, the patch 1708 includes one or more hormonal agents, such as growth factors to promote wound healing and other therapeutic agents. In a specific embodiment, a hormonal agent may be delivered via a delivery vehicle, such as a nanoparticle or microparticle.

The occlusion patch 1708 may include any of various dimensions. In some embodiments and as shown in FIG. 17A, the occlusion patch 1708 extends over substantially the entire length of the working portion 1710 of the inflatable balloon 1704. In some embodiments, the occlusion patch 1708 extends over only a portion of the length of the working portion 1710 of the inflatable balloon 1704. In some embodiments and as shown in FIG. 17B, the occlusion patch 1708 extends over only a portion of the circumference of the working portion 1710 of the inflatable balloon 1704. In some embodiments, the occlusion patch 1708 extends over substantially the entire circumference of the working portion 1710 of the inflatable balloon 1704.

Although FIGS. 17A and 17B only illustrate a single occlusion patch 1708, in some embodiments the inflatable balloon 1704 carries a plurality of occlusion patches 1708. The patches 1708 may be offset from each other along the length and/or about the circumference of the working portion 1710 of the inflatable balloon 1704.

A number of variations and modifications to the occlusion balloon devices 1302 and 1502 may be used. For example, if the catheters 1302 or 1502 is to be inserted using a non-femoral vein approach (for example, a jugular vein approach), the working portion may have a distal section with a relatively large diameter and a proximal section with a relatively small diameter. As another example, a perfusion lumen could be formed as part of a balloon device instead of the catheter shaft.

FIG. 18 is a side view of an exemplary occlusion balloon device 1802 device according to embodiments of the present disclosure. The occlusion balloon device 1802 generally includes an inflatable balloon 1804 that is carried at a distal portion of a catheter shaft 1806. The occlusion balloon device 1802 also includes a connection hub 1808 that is carried at a proximal portion of the catheter shaft 1806. The connection hub 1808 and the catheter shaft 1806 may carry a distally-tapering strain relief 1810 at an interface therebetween. The catheter shaft 1806 also carries three radiopaque markers 1812 such that the position of the occlusion balloon device 1802 may be determined via medical imaging (for example, via fluoroscopy). A first radiopaque marker 1812 may be axially near an intersection of a proximal neck 1814 of the balloon 1804 and a proximal tapered portion 1816 of the balloon 1804. A second radiopaque marker 1812 may be axially near an intersection of the proximal tapered portion 1816 and a working portion 1818 of the balloon 1804. A third radiopaque marker 1812 may be axially near an intersection of the working portion 1818 and a distal tapered portion 1820 of the balloon 1804. The device 1802 has an effective length 1822 (that is, a length between the distal end of the strain relief 1810 and the distal end of the shaft 1806) of about 88 cm (that is, 88 cm±1 cm). The device 1802 has a maximum outer diameter, or crossing profile, of about 4 mm (that is, 4 mm±0.1 mm)

FIG. 19 is a side view of a distal portion of the occlusion balloon device 1802 of FIG. 18, wherein the inflatable balloon 1804 is depicted in an inflated state. The inflatable balloon 1804 includes a wall 1902, an inflation chamber 1904, the proximal neck 1814 (which has a length 1906 and an outer diameter 1907), a distal neck 1908 having a length 1910 and an outer diameter 1911, the working portion 1818 (which has a length 1912), the proximal tapered portion 1816 disposed between the proximal neck 1814 and the working portion 1818, and the distal tapered portion 1820 disposed between the distal neck 1908 and the working portion 1818.

The wall 1902 of the inflatable balloon 1804 defines the inflation chamber 1904. The inflation chamber 1904 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the lead removal catheter 104 into the vasculature, positioning the inflatable balloon 1804 adjacent the perforation 108 and inflating the inflatable balloon, the inflatable balloon 1804 facilitates occlusion of the perforation 108.

In some embodiments, the inflatable balloon 1804 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 1804 may be formed of one or more elastomeric materials, such as polyurethane. For example, the inflatable balloon 1804 may be formed of Pellethane®, specifically 80AE Pellethane®, which is available from The Lubrizol Corporation of Wickliffe, Ohio. The inflatable balloon 1804 may have a Shore A durometer of about 85 A (that is, 85 A±4 A).

The inflatable balloon 1804 includes the proximal neck 1814, which engages the catheter shaft 1806 (via one or more adhesives, a compression fit, or the like). The proximal neck 1814 may have an inner diameter of about 2.5 mm (that is, 2.5 mm±0.07 mm). The proximal neck 1814 may have a length 1906 of about 10 mm (that is, 10 mm±2 mm). The proximal neck 1814 may have an outer diameter 1907 of about 3.0 mm (that is, 3.0 mm±0.1 mm). The proximal neck 1814 may have a wall thickness of about 0.24 mm (that is, 0.24 mm±0.01 mm).

Distal to the proximal neck 1814, the proximal neck 1814 couples to the proximal tapered portion 1816. The proximal tapered portion 1816 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1804 is inflated, the proximal tapered portion 1816 may be disposed at an angle of about 45 degrees (that is, 45 degrees±0.5') relative to a longitudinal axis of the inflatable balloon 1804.

Distal to the proximal tapered portion 1816, the proximal tapered portion 1816 couples to the working portion 1818. The working portion 1818, when the inflatable balloon 1804 is appropriately positioned and inflated, occludes the perforation 108. The working portion 1818 may have an inflated outer diameter 1914 of about 20 mm (that is, 20 mm±2 mm). The working portion 1818 may have a length 1912 of about 80 mm (that is, 80 mm±3 mm). The working portion 1818 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The ratio of the length 1912 of the working portion 1818 to the outer diameter 1914 of the inflatable balloon 1804 in the inflated state is, therefore, about 4:1. Having this ratio with a relatively constant inflated outer diameter 1914 of about 20 mm for a length 1912 of about 80 mm increases the likelihood that the inflatable balloon 1804 will occlude the perforation 108 when placed adjacent the perforation 108 in the patient vasculature and inflated. That is, the length 1912 of the working portion 1818 of the inflatable balloon 1804 is designed to be substantially longer than the perforation 108, thereby potentially increasing the clinician's ability to quickly locate and occlude the perforation.

As mentioned above, the working portion 1818 of the inflatable balloon 1804 may have an inflated outer diameter 1914 of about 20 mm (that is, 20 mm±2 mm). Inflating the outer diameter 1914 of the working portion 1818 of the inflatable balloon 1804 to this diameter increases the likelihood that the working portion 1818 of the inflatable balloon 1804 will be about the same diameter or slightly larger than the diameter of the blood vessel 102 at the perforation 108. Inflating the outer diameter 1914 of the working portion 1818 of the inflatable balloon 1804 to be about the same diameter or slightly larger than the diameter of the blood vessel 102 at the perforation 108 increases the likelihood that the inflatable balloon 1804 will block the perforation 108 without increasing its size.

Again, the inflatable balloon 1804 may be formed of one or more elastomeric materials, such as polyurethane. To inflate the inflatable balloon 1804 to the diameter referenced above, it may also be desirable to inflate the inflatable balloon 1804 with an inflation fluid to a pressure within the balloon inflation chamber 1904 from about 0 psi to about 3 psi. The amount of inflation fluid used to inflate the inflatable balloon 1804 to such a pressure and/or at the desired diameter is about 25 ml (cc). Furthermore, the elastomeric material may provide the inflatable balloon 1804 with the compliance characteristics shown in Table 1. That is, providing the inflatable balloon 1804 with a specific volume of inflation fluid may cause the balloon 1804 to inflate to a specific diameter as shown in Table 1.

TABLE 1

Exemplary compliance characteristics of the inflatable balloon 1804.

| Inflation Volume (ml, cc) | Balloon Diameter (mm) |
|---|---|
| 20 | 18.8 |
| 25 | 19.4 |
| 30 | 21.3 |
| 35 | 23.4 |
| 40 | 25.2 |
| 45 | 26.9 |
| 50 | 28.6 |
| 55 | 29.9 |
| 60 | 31.1 |

Distal to the working portion 1818, the working portion 1818 couples to the distal tapered portion 1820. The distal tapered portion 1820 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1804 is inflated, the distal tapered portion 1820 may be disposed at an angle of about 45 degrees (that is, 45 degrees±0.5') relative to the longitudinal axis of the inflatable balloon 1804.

Distal to the distal tapered portion 1820, the distal tapered portion 1820 couples to the distal neck 1908, which engages the catheter shaft 1806 (via one or more adhesives, a compression fit, or the like). The distal neck 1908 may have an inner diameter of about 2.5 mm (that is, 2.5 mm±0.07 mm). The distal neck 1908 may have a length 1910 of about 10 mm (that is, 10 mm±2 mm). The distal neck 1908 may have an outer diameter 1911 of about 3.0 mm (that is, 3.0 mm±0.1 mm). The distal neck 1908 may have a wall thickness of about 0.24 mm (that is, 0.24 mm±0.01 mm). Between the distal neck 1908 and the proximal neck 1814, the inflatable balloon 1804 may have a length 1916 of about 100 mm (that is, 100 mm±1 mm).

The first radiopaque marker 1812 may be offset from the intersection of the proximal neck 1814 and a proximal tapered portion 1816 by a distance 1918 of about 1 mm (that is, 1 mm±1 mm). The second radiopaque marker 1812 may be offset from the first radiopaque marker 1812 by a distance 1920 of about 10.27 mm (that is, 10.27 mm±1 mm). The third radiopaque marker 1812 may be offset from the first radiopaque marker 1812 by a distance 1922 of about 86 mm (that is, 86 mm±1 mm).

FIGS. 20A-20D are views of the catheter shaft 1806. The catheter shaft 1806 may be formed of one or more elastomeric materials, such as polyurethane. For example, the catheter shaft 1806 may be formed of Pellethane®, specifically 75D Pellethane®, which is available from The Lubrizol Corporation.

The catheter shaft 1806 may have an outer diameter 2002 of about 2.286 mm (that is, 2.286 mm±0.04 mm). The catheter shaft 1806 may have a length of about 110 cm (that is, 110 cm±0.3 cm).

The catheter shaft 1806 includes a first lumen 2004 that is adapted to receive a guidewire or an implanted cardiac lead to guide the occlusion balloon device 1802 to a position proximate the perforation 108. The first lumen 2004 is non-centrically disposed relative to the outer diameter 2002 of the catheter shaft 1806. Assuming that the first lumen 2004 is adapted to receive a guidewire having a diameter of about 0.9 mm (0.035 inches), the first lumen 2004 may have circular cross section and have a diameter of about 0.954 mm (that is, 0.954 mm±0.04 mm). If, however, the first lumen 2004 is adapted to receive an implanted cardiac lead, the first lumen 2004 may have a different cross section diameter. Also, although the first lumen 2004 is depicted as having a circular cross section, the cross-sectional shape of the first lumen 2004 may have a non-circular section, such as an oval. A minimum wall thickness between the first lumen 2004 and the outer diameter 2002 may be about 0.15 mm (that is, 0.15 mm±0.025 mm).

The catheter shaft 1806 also includes a second lumen 2006 that is adapted to receive the inflation fluid from the connection hub 1808 and deliver the inflation fluid to the balloon inflation chamber 1904. The second lumen 2006 is non-centrically disposed relative to the first lumen 2004 and the outer diameter 2002 of the catheter shaft 1806. The second lumen 2006 may have a circular cross section or a non-circular cross-sectional shape, such as a crescent-like cross-sectional shape or a semi-circular shape. Assuming that the second lumen 2006 has a crescent-like cross-sectional shape or a semi-circular shape, the second lumen 2006 may have a width of about 1.8 mm (that is, 1.8 mm±0.025 mm). The second lumen 2006 may have a height in a plane that bisects the catheter shaft 1806 of about 0.76 mm (that is, 0.76 mm±0.025 mm). It is desirable to introduce as much inflation fluid through the second lumen 2006 and into the inflation chamber of the inflatable balloon as quickly as possible, in order to inflate the inflatable balloon as quickly as possible and minimize potential blood loss through the perforation. Accordingly, it is desirable to have as large as possible a cross-sectional area for the second lumen 2006 for a given outer diameter 2002 of the catheter shaft 1806. For example, for an outer diameter 2002 of about 2.286 mm (that is, 2.286 mm±0.04 mm), the cross-sectional area for the second lumen 2006 may be between 0.65 mm$^2$ and 1.90 mm$^2$ or any increment of 0.01 mm$^2$ therebetween, such as 0.66, 0.67, 0.68, 0.69, 0.70 . . . 1.0 . . . 1.5 . . . 1.9 mm$^2$.

A minimum wall thickness between the second lumen 2006 and the first lumen 2004 may be about 0.1 mm (that is, 0.1 mm±0.025 mm). A minimum wall thickness between the second lumen 2006 and the outer diameter 2002 may be about 0.15 mm (that is, 0.15 mm±0.025 mm). Assuming a minimum thickness between the second lumen 2006 and the outer diameter 2002 is about 0.15 mm, a radius for the crescent-like cross-sectional shape or a semi-circular shape of about 1 mm correlates to a cross-sectional area of the lumen 2006 of between about 1.4 mm$^2$ and 1.7 mm$^2$, and depending upon the wall thickness between the second lumen 2006 and the first lumen 2004, the radius for the crescent-like cross-sectional shape or a semi-circular shape of about 1 mm correlates to a cross-sectional area of the lumen 2006 of between about 1.50 mm$^2$ and 1.60 mm$^2$, and about 1.55 mm$^2$. The crescent-like cross-sectional shape or a semi-circular shape may alternatively have a radius of about between 0.50 mm to 1.50 mm.

Figure 20A:
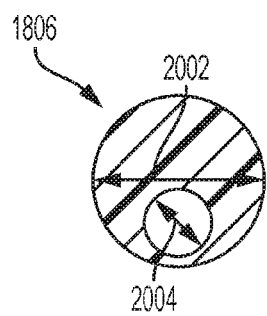
FIG. 20A is a cross-sectional view of a catheter shaft of the occlusion balloon device along line 20A-20A of FIG. 18.
Figure 20B:
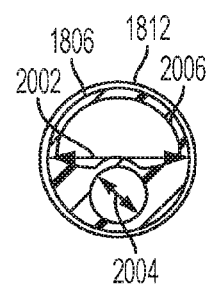
FIG. 20B is a cross-sectional view of the catheter shaft of the occlusion balloon device along line 20B-20B of FIG. 18.
Figure 20C:
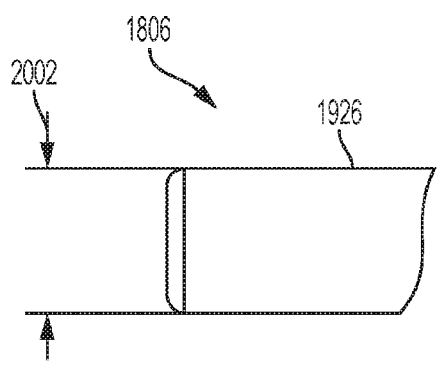
FIG. 20C is a detail view of the catheter shaft of the occlusion balloon device within line 20C-20C of FIG. 18.
Figure 20D:
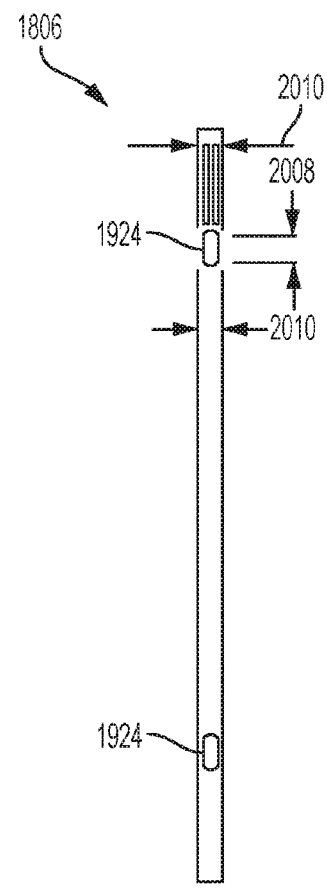
FIG. 20D is a top view of a distal portion of the catheter shaft of the occlusion balloon device of FIG. 18.

The catheter shaft 1806 also includes two apertures 1924 that couple the second lumen 2006 to the exterior of the catheter shaft 1806 and the balloon inflation chamber 1904. That is, the second lumen 2006 delivers the inflation fluid to the inflatable balloon 1804 via the apertures 1924. Referring briefly to FIG. 19, a first aperture 1924 may be axially aligned with the proximal tapered portion 1816 of the balloon 1804 and a second aperture 1924 may be axially aligned with the distal tapered portion 1820 of the balloon 1804. Referring specifically to FIG. 20D, each aperture 1924 may have an axial length 2008 of about 5 mm (that is, 5 mm±1 mm) and a transverse width 2010 of about 1.8 mm (that is, 1.8 mm±0.3 mm). The second lumen 2006 may be covered at the distal end of the catheter shaft 1806 (for example, by a separate cover 1926, the wall of the catheter shaft 1806, or the like). If the catheter shaft 1806 includes a separate cover 1926, the cover 1926 may be offset from the distal neck 1908 by a distance 1928 of about 10 mm (that is, 10 mm±2 mm). The cover 1926 may have an axial length 1930 about 5 mm (that is, 5 mm±2 mm). The catheter shaft 1806 may also include a third aperture (not shown) disposed within the connection hub 1808 to facilitate receiving the inflation fluid from a lumen of the connection hub 1808.

In some embodiments, the dimensions and material properties of the inflatable balloon 1804, the catheter shaft 1806, and the catheter shaft 1806 facilitate using the occlusion balloon device 1802 with relatively small guidewires and introducer sheaths and relatively quickly delivering the inflation fluid to the inflatable balloon 1804 (for example, in 40 seconds or less). Having two or more of the following allows the clinician to quickly inflate the inflatable balloon 1804 with the inflation fluid: a crescent-like cross-sectional shape for the second lumen 2006; a wall thickness between the first lumen 2004 and the outer diameter 2002 about 0.15 mm; a wall thickness between the second lumen 2006 and the outer diameter 2002 about 0.15 mm; wall thickness between the second lumen 2006 and the first lumen 2004 about 0.1 mm; and the apertures 1924 having an axial length 2008 of about 5 mm and a transverse width 2010 of about 1.8 mm, one aperture 1924 being axially aligned with the proximal tapered portion 1816, and the other aperture 1924 being axially aligned distal tapered portion 1820. Testing has demonstrated that occlusion balloon devices having such properties can receive 60 ml of inflation fluid (being 80 percent saline and 20 percent contrast solution) in an average time of 25.6 seconds with a standard deviation of 1.3 seconds to facilitate inflation of the occlusion balloon to a diameter of 31.1 mm. Furthermore, the occlusion balloon device 1802 has sufficient strength for entering a subject's vasculature and occluding a vascular perforation.

The radiopaque markers 1812 may be similar to the radiopaque marker bands 602 described above. The radiopaque markers 1812 may be formed of one or more radiopaque materials, such a mixture of about 90 percent platinum (that is, 90 percent±1 percent) and 10 percent iridium (that is, 10 percent±1 percent). The radiopaque markers 1812 may have an open-ended cylindrical shape that is adapted to extend around the circumference of the catheter shaft 1806. The radiopaque markers 1812 may each have an outer diameter in a range of about 2.489 mm (that is, 2.489 mm±0.1 mm). The radiopaque markers 1812 may each have an inner diameter of about 2.2 mm (that is, 2.2 mm±0.01 mm) to about 2.4 mm (that is, 2.4 mm±0.01 mm). The radiopaque markers 1812 may each have a length of about 1.2 mm (that is, 1.2 mm±0.05 mm).

Figure 21:
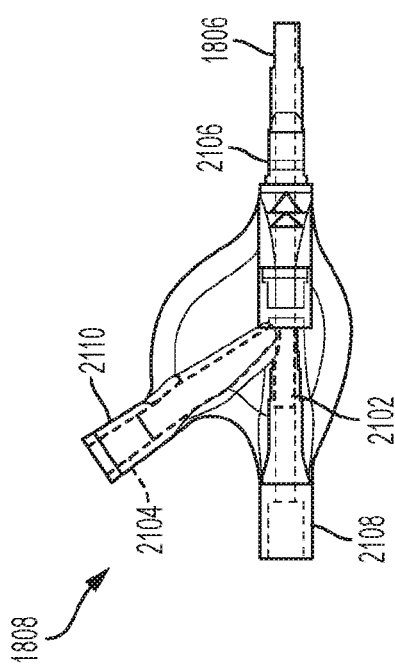
FIG. 21 is a side view of a connection hub of the of the occlusion balloon device of FIG. 18.

FIG. 21 is a view of the connection hub 1808. The connection hub 1808 may be formed of one or more polymers, such as Polycarbonate, specifically Makrolon®, which is available from Bayer MaterialScience of Darmstadt, Germany. The connection hub 1808 includes a bifurcate lumen, which in turn includes a main lumen 2102 and a branch lumen 2104. The branch lumen 2104 extends from the main lumen 2102 at an acute angle. The main lumen 2102 may have an inner diameter in a range of about 2.2 mm (that is, 2.2 mm±0.025 mm) to about 2.4 mm (that is, 2.4 mm±0.025 mm). The main lumen 2104 couples to a first port 2108 on a distal side of the connection hub 1808. The first port 2108 couples to the catheter shaft 1806 and the strain relief 1810. The main lumen 2104 couples to a second port 2108 on a proximal side of the connection hub 1808. The second port 2108, which may be, for example, ISO 594-1, 594-2-complaint Luer connector, is adapted to receive a guidewire and/or couple to an inflation fluid source, such as a syringe, specifically a 60 ml (cc) syringe. The branch lumen 2104 couples to a third port 2110 on the proximal side of the connection hub 1808. The third port 2110, which may be, for example, ISO 594-1, 594-2-complaint Luer connector, is adapted to receive a guidewire and/or couple to an inflation fluid source, such as a syringe, specifically a 60 ml (cc) syringe.

Figure 22:
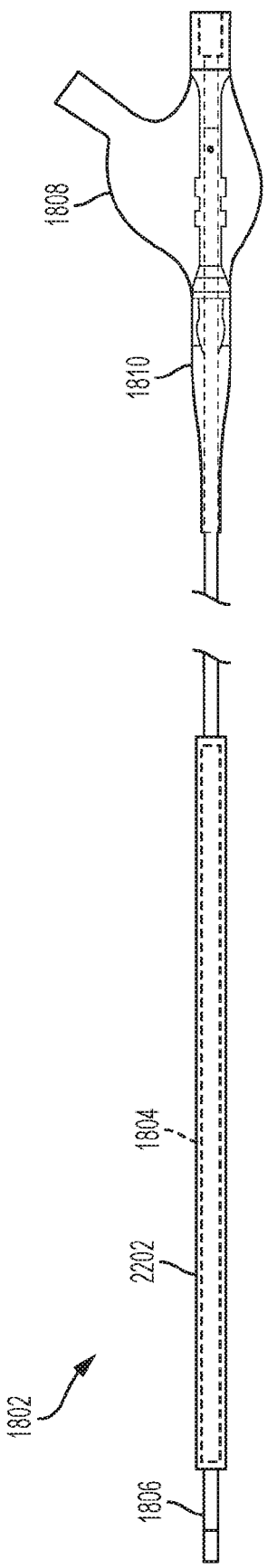
FIG. 22 is a side view of the occlusion balloon device of FIG. 18 in which a balloon of the occlusion balloon device is in a deflated state and obscured by a protective cover.

FIG. 22 is a view of the occlusion balloon device 1802 in a state in which the device 1802 may be provided to a medical practitioner. Specifically, the device 1802 may include a protective cover 2202 disposed about the inflatable balloon 1804. The protective cover 2202 may extend proximally beyond the proximal end of the balloon 1804 and distally beyond the distal end of the balloon 1804.

FIGS. 23A and 23B are views of a distal portion of another exemplary occlusion balloon device 2302 device according to embodiments of the present disclosure. The occlusion balloon device 2302 is also interchangeably referred to herein as an expandable member for occluding a perforation in a blood vessel. A perforation in a blood vessel is also interchangeably referred to herein as a target site. The occlusion balloon device 2302 generally includes an inflatable balloon 2304, which may be similar to any of the balloons described herein. The inflatable balloon 2304 is carried at a distal portion of a catheter shaft 2306, which may be similar to any of the catheter shafts described herein. The occlusion balloon device 2302 also includes a connection hub (not shown), which may be similar to the connection hubs described above. The connection hub is carried at a proximal portion of the catheter shaft 2306. The connection hub and the catheter shaft 2306 may carry a distally-tapering strain relief (not shown), which may be similar to the strain reliefs described above, at an interface therebetween. Inflatable balloon 2304 includes proximal and distal ends 2308 and 2310 respectively. Inflatable balloon 2304, having a stiffness, is generally compliant and expandable and may be made of materials similar to any of the balloons described herein.

The expandable member or occlusion balloon device 2302 further comprises rigid proximal balloon 2312 and rigid distal balloon 2314, wherein inflatable balloon 2304 is centrally disposed between proximal and distal balloons 2312 and 2314, respectively. Inflatable balloon 2304 is also refereed to interchangeably herein as central expandable balloon, or simply, as central balloon. Expandable member 2302 further includes longitudinal axis A. In some embodiments, rigid balloons 2312 and 2314 are disposed longitudinally about balloon 2304. In some embodiments, rigid balloons 2312 and 2314 and balloon 2304 are longitudinally offset relative to one another.

Balloons 2312 and 2314 have substantially the same stiffness as one another, thereby ensuring that they will burst substantially simultaneously with the same pressure applied to the balloons. Balloons 2312 and 2314 are advantageously less compliant than balloon 2304. In some embodiments, balloons 2312 and 2314 have a pressure strength at burst less than that of balloon 2304. The stiffness of balloon 2304, disposed between balloon 2312 and balloon 2314, is less than the stiffness of balloon 2312 and 2314. Balloons 2312 and 2314 are detachably carried on the outer surface of the inflatable balloon 2304 at ends 2308 and 2310. In some embodiments, inflatable balloon 2304, disposed between rigid balloons 2312 and 2314, is configured to expand.

Balloon 2312 contains a composition 2316, and balloon 2314 contains a composition 2318. As will be discussed hereinbelow with respect to FIGS. 24A to 24E, by expanding balloon 2304, this causes direct pressure on balloons 2312 and 2314 to substantially simultaneously release composition 2316 and composition 2318, thereby allowing the compositions 2316 and 2318 to combine and mix in-situ to form a biocompatible foam within the vasculature. Substantially simultaneously releasing means releasing at about or approximately the same time. As one skilled in the art would recognize, the release of composition 2316 and composition 2318 need to occur approximately concurrently so that sufficient combining or mixing of the two compositions may be achieved.

The compositions 2316 and 2318 may be any suitable to combine or mix to form in-situ a biocompatible foam. In some embodiments, compositions 2316 and 2318 represent first and second compositions that are polymeric. In other embodiments, a first composition is polymeric and a second composition is aqueous. Systems relating to in-situ forming polymer foams suitable for use in the present invention include those as disclosed in U.S. Pat. Nos. 9,044,580, 9,173,817, 9,522,215, and 9,579,449, and in U.S. Publ. Appl. Nos. 2011/0202016, 2012/0040137, 2012/0265287, 2014/0316367, 2015/0223819, 2015/0224235, 2016/0051264, 2016/0082144, and 2016/0279302, which are hereby incorporated herein by reference in their entireties for all that they teach and for all purposes.

The biocompatible polymer foams of the present disclosure are formed "in-situ." That is, the foams are formed by the reaction of polymer(s) in-situ simultaneously with, or shortly after, delivery to a vasculature perforation or other bodily cavity. It should be understood that, throughout the description of the present disclosure, the systems and methods of the present disclosure are applicable to any suitable bodily cavity notwithstanding that the invention is described with specific reference to the treatment of vasculature perforations. The polymer(s) react in the presence of an aqueous environment (e.g., blood, water, etc.,) or other trigger (e.g., pH, temperature, ion concentration, electrical current, magnetic field or other trigger) in a one-part system and/or react with each other (e.g., for embodiments in which polymer components are delivered separately and either concurrently or sequentially) in a two- or multi-part system, upon such delivery.

Compositions 2316 and 2318 may be the same or different. In some embodiments wherein compositions 2316 and 2318 are the same, this is a non-limiting example of a one-part system wherein the compositions interact with fluids present in the vessel at the target site or the vascular perforation. An example of a one-part system is isocyanate hydrolyzing upon coming in contact with water (or aqueous fluid in a vessel) to form $CO_2$ and an amine as gas evolution and crosslinking occur together to form in-situ the biocompatible foam. In other embodiments wherein compositions 2316 and 2318 are different, this is a non-limiting example of a two-part system wherein the compositions interact with each other at or proximate the target site, for example, a vascular perforation. An example of a two-part system is a polyurethane foam wherein one of compositions 2316 or 2318 is an isocyanate compound, and the other of compositions 2316 or 2318 is a hydroxyl-functionalized polymer (polyol). The one-part and two-part systems are discussed in detail below. These in-situ biocompatible foam formulations are in contrast to pre-formed foams, which are formed prior to the time that they are delivered into the body.

The foamed polymers of the present disclosure may be capable of exerting a pressure on an internal surface of a vasculature perforation and thus prevent or limit movement of a bodily fluid (e.g., blood, etc.) and/or prevent or limit endoleaks. Such in-situ forming foams preferably expand to fill the vasculature perforation, resulting in conformal contact with the vessel walls and may include penetration into blood vessels and other lumens opening into the vasculature perforation without clinically undesirable embolization. The location of such vessels is not always obvious with standard imaging technique, such that the ability to seal such vessels with the foams and methods of the present disclosure without requiring visualization is a unique advantage of the present disclosure. Also, the foams are formed by the reaction of polymers in-situ to yield gas generation and expansion, which allow for the use of minimal polymer materials to fill the space and allows the resulting foam to push through fluid, including actively flowing blood, to provide conformal contact with surrounding tissue.

In some embodiments, the foam of the present disclosure is described to be "lava like" in that it is viscous yet flowable and hardens from its exterior surface towards its interior. The external skin of the foam forms as a fast-forming, robust, balloon-like outer layer that encases the polymer formulation, promotes material cohesion, and resists deformation and movement into collateral vessels or outside the targeted area. Formation of the skin occurs in whole or in part due to contact with a trigger in the environment (e.g., water, temperature, blood, etc.), and therefore, as the foam expands and the skin deforms to expose internal formulation, it too will react and reform the skin rapidly. The outer layer may be characterized as being "robust" because it has mechanical properties (e.g., strength, toughness, etc.) that are more optimal, at least for some period of time, to the material contained by the skin. The interior of the material hardens more slowly via the same or a secondary process, as compared to the skin. In some cases where the skin forms rapidly and is likely sufficiently robust mechanically, resulting in a continuous, packable polymer, which may tend to form as a coil. Through continued extrusion of the material out of a delivery device such as a catheter or microcatheter, the user can create a long coil to partially or completely fill a vasculature perforation or other bodily cavity. The space may be filled with a coil or other medical device and an in-situ forming foam or a coil or other medical device that is coated with a material that expands to form a foam coating in-situ. The continuous, long aspect ratio of the coil and cured outer surface prevents the coil from entering the collateral vessels to a significant degree, which could lead to adverse events. In addition, some embodiments could be envisioned where the coil diameter expands to a size that is larger than any of the collateral vessel diameters, thus preventing entry into the collateral vessels in the short aspect ratio as well. These and other factors are important distinctions and advantages of in-situ forming foams over systems and methods that make use of pre-formed foams.

The biocompatible polymer foams of the present disclosure may possess attributes that make them particularly suitable for use within the body. For example, the foams of the present disclosure are biocompatible and may be either biodegradable or biostable. In some instances, the polymers may be sufficiently elastic to allow for body movement while being sufficiently stiff to support body tissues and the endovascular graft or associated or similar medical devices. In some embodiments, the composition may be adjusted so that it wets tissues effectively. Furthermore, pendant groups may be attached that allow for the targeted adhesion of polymer to tissues or injured tissues. Functionalization of the polymer used to form the foam may also lead to covalent bonding of the foam to a surface inside the vasculature perforation, which may aid, for example, in preventing dislocation of the foam within the cavity. In addition, the polymers may comprise entities that allow for the degradation of the polymer foam via an external stimulus such as UV radiation, heat, etc. The polymers and/or foams formed therefrom may also be capable of interacting with contrast agents, allowing for the visualization of the foam and/or a vasculature perforation. This interaction may be permanent or temporary. These and other aspects of the foams used in the present disclosure are more fully described herein.

As used herein, a "foam" refers to an article comprising a plurality fluid-filled (i.e., with gas or liquid) of cells (i.e., volumes) that are at least partially surrounded by a material comprising a polymer, and is preferably biocompatible and nonabsorbable. The cells within the foam may be open or closed. The cells within the foam may be any suitable size, such as one or more nanometers, microns, millimeters, or centimeters. The cell size may be substantially uniform throughout the foam, such as where at least 90% of the cells are the same order of magnitude in size, or may have a wide size distribution spanning two or more orders of magnitude. In some embodiments, the polymer foam may comprise at least 10 cells, at least 100 cells, at least 1000 ceils, at least 10,000 cells, or more. The foam is formed in-situ substantially commensurately with the delivery of a foam-forming formulation into the vasculature perforation, whereupon it reacts with blood present within the perforation, or with saline, water or other suitable fluid delivered together with the polymer, or with another aqueous environment. Such fluid may pre-exist at the delivery site (as in the case of blood) in a so-called "one-part system," or it may be delivered to the site concurrently with the formulation or it may be pre-mixed with the formulation shortly before delivery in so-called "two-part systems." In such two-part systems, the fluid delivered with (or pre-mixed with) the formulation is preferably saline, water or buffered aqueous solution.

The formulation material can comprise a plurality of polymers or prepolymers that can be, for example, cross-linked to each other in the process of forming a polymer foam. In some embodiments, the formulation comprises fluid polymers (including for example, amorphous polymers with glass transition temperatures below room temperature, or crystalline polymers with melting and glass transition temperatures below room temperature) in the substantial absence of a carrier fluid. In other instances, the plurality of polymers in the formulation are suspended in a carrier fluid (e.g., a liquid suspension medium, emulsion, dispersion, etc.) or dissolved in a carrier fluid to create a homogeneous phase. The term "polymer" is given its ordinary meaning in the art, and is used to refer to a molecule that includes a plurality of monomers. Included within the definition of "polymer" are "pre-polymers," which are a subclass of polymers that are characterized by reactive groups in the polymer chain. Such pre-polymers are of particular use in the present invention because the reactive groups in such polymers help drive the in-situ forming foam reaction. In some embodiments, a polymer may comprise fewer than about 100, fewer than about 50, fewer than about 25, or fewer than about 10 monomer units, In some embodiments, a polymer may comprise between about 2 and about 100, between about 2 and about 50, between about 2 and about 25, between about 5 and about 50, or between about 5 and about 25 monomer units. The polymers within the formulation can comprise a variety of functional groups that allow the polymers to, for example, cross-link to each other, attach to tissue or other material within the vasculature perforation, interact with agents in the bloodstream of the subject (e.g., imaging agents, cross-linking agents, etc.), among other functionalities.

In some embodiments, the polymers within the formulation may cross-link within the vasculature perforation. The term "cross-linking" is used to refer to the process whereby a pendant group on a first polymer chain may react with a second polymer chain (e.g., a pendant group on the second polymer) or other molecule or molecules to form a covalent or ionic bond joining the two polymers. Polymers that can undergo cross-linking can comprise straight chains, branched chains having one or more arms (i.e., multi-arm chains), or mixtures of these. In some cases, the polymer (branched and/or non-branched) may contain reactive side chains and/or reactive terminal groups (i.e., groups at the end of a polymer chain), and cross-linking may involve reactions between the side chains, between terminal groups, and/or between a side chain and a terminal group. In some instances, the formulation may be substantially free of polymers that comprise reactive groups on terminal monomers. In other cases, the formulation may comprise a substantial amount of polymers with reactive groups on terminal monomers. In some embodiments (e.g., in some cases in which branched polymers are employed) a relatively large percentage of the cross-linking reactions (e.g., at least about 70%, at least about 80%, at least about 90%, at least about 95%, at least about 99%, or substantially all of the cross-linking reactions) can occur between terminal reactive groups.

Cross-linking may commence via a variety of mechanisms. In some embodiments, polymer may cross-link once the polymer contact moisture (e.g., water, blood, aqueous solutions, etc.), for example, within a vasculature perforation. Cross-linking may be achieved via acrylate, methacrylate, vinyl, cinnamic acid, or acrylamide groups in some embodiments. Such groups may be cross-linked via the application of ultraviolet radiation and can be used in conjunction with an external foaming agent. In some instances, a cross-linking initiator may be introduced into the subject in which the vasculature perforation is located (e.g., via the bloodstream, via a separate container in the delivery system such that the initiator and the polymer do not mix before delivery, etc.) to initiate cross-linking of the polymer. For example, a free radical initiator, such as eosin or 2,2-dimethoxy-2-phenylacetophenone, can be used to initiate cross-linking of polymers bearing acrylate, methacrylate, or vinyl groups. Other examples of reactive groups on polymer chains that can be paired to produce cross-linking include, but are not limited to, hydroxyls and isocynates, amines and NHS-esters, thiols and maleimides, azides and alkynes (i.e., "click chemistry"), acid chlorides and alcohols, and in a preferred embodiment, isocyanates any polyols. It may be desirable, in some embodiments, to keep these paired chemicals separate until they are introduced into the vasculature perforation from a container separate from the container used to introduce vasculature perforation. For example, the polymer may include azide functional groups, and alkynes can be introduced to the vasculature perforation from a container separate from the container used to introduce the polymer. In some embodiments, these chemistries are also employed in conjunction with an external foaming agent. As the formulation cross-links, its viscosity may be increased. In some cases, the cross-linking proceeds until a cellular solid material (e.g., a solid elastomeric foam) is formed.

In some embodiments, a gas is formed from the reaction of the polymer supplied to the vasculature perforation. For example, in some embodiments, the foaming step comprises reacting one or more pendant groups on the polymer or cross-linked product to form a gaseous product. The gas-producing pendant groups may react upon contact with another material in the vasculature perforation. For example, in some cases, the gas producing groups may react upon contact with moisture in the vasculature perforation. In some cases, the gas-producing pendant groups may react with a chemical supplied to the vasculature perforation separately from the formulation (e.g., via the bloodstream, via an external source separate from the polymer material source, etc.). In some embodiments, the gas-producing pendant groups on the polymer chain may react with another component that is supplied to the vasculature perforation. In some embodiments, the polymer or cross-linked product may comprise $CO_2$-producing groups. $CO_2$ producing groups are preferred due to the biocompatibility of $CO_2$ and high solubility of $CO_2$ in blood. Examples of $CO_2$-producing groups include, but are not limited to, isocyanate groups, carbonates, bicarbonates, and carbamates. Such groups may produce $CO_2$ when reacted with an acid, for example. In some cases, the $CO_2$-producing group may include an N-hydrosuccinimide carbonate, illustrated below:

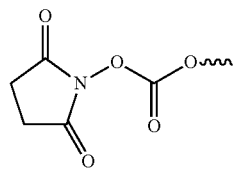

$CO_2$-producing groups may include, in some cases, imidazole carbamates, as illustrated below:

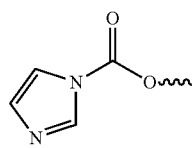

As noted above, in some embodiments, the foaming and cross-linking steps occur substantially simultaneously. In some cases, the foaming and cross-linking steps may occur substantially simultaneously, but remain independent of each other. For example, the formulation may cross-link by reacting with water in the vasculature perforation, and, at substantially the same time, gas may be introduced to the formulation from an external container. In another embodiment, a first material containing gas generating groups may produce gas by contact with a second agent (e.g., water in the body, water supplied separately, or chemical additive), while contact or interaction with a third material leads to cross-linking. For example, at the time of delivery, polymer A with isocyanate groups can be mixed with water and polymer B, in which the former causes the generation carbon dioxide to foam the material and polymer B can contain hydroxyl groups that react with isocyanates on polymer A to form a crosslinked network between polymers A and B.

The foaming and cross-linking steps may be, in some cases, part of the same reaction process. In embodiments of a one-part system, isocyanate hydrolyzes when it contacts water, forming $CO_2$ and an amine. This newly formed amine can react with any remaining unhydrolyzed isocyanate groups, thereby crosslinking the material. In this case, gas evolution and crosslinking occur together, where the latter is dependent upon the former for it to occur. In other examples, one or more reactions may produce a gaseous by-product which serves as the supply of gas to form the polymer foam, but concurrently leads to the generation of new functional groups that enable crosslinking. The gaseous by-product can be trapped within the formulation and coalesce to form bubbles. As the reaction progresses, the formation, growth and expansion of the gas bubbles can expand the polymer volume and force it into interstitial areas of the vasculature perforation. As the polymer cross-links, a three-dimensional foam can be formed within the vasculature perforation the volume expansion and cross-linking can serve to coat and form a seal with surfaces of the vasculature perforation, and optionally provide internal compression, which may be useful, for example, in controlling movement of blood and stabilizing the stent graft. In addition, such a reaction scheme can be combined with an external supply of gas (e.g., $CO_2$ in an external container) to increase the amount of gas contained in the formulation or a cross-linked product of the polymer.

All of the foaming mechanisms described herein may occur before any substantial cross-linking has occurred or during cross-linking of the formulation or a cross-linked product of the formulation. For example, in some cases, an external gas may be introduced into and dispersed within a formulation that has not substantially cross-linked. The formulation may then cross-link around the bubbles to form the foam. In such cases, the viscosity and surface tension of the formulation can be chosen such that the material is able to retain bubbles within the volume without the need for cross-linking. In another embodiment, a surfactant can be added to the formulation to create a formulation that retains gas bubbles without the need for crosslinking. In some embodiments, at least some cross-linking may occur before the gas is introduced to the formulation, and the gas is dispersed within a partially cross-linked formulation that has not completely solidified to form a foam.

The solidification of interior portions of foams that form with an exterior skin can be controlled, for example, by altering the permeability of the material to a solidification trigger. In the case that the trigger is water, permeability can be controlled by adjusting material hydrophobicity. Additional ingredients can be added to adjust material radiopacity, density, and/or contact angle with blood, tissue, or other biological matrices.

Cross-linking and/or foaming may be achieved, in some instances, using isocyanate chemistry. Isocyanate groups are relatively unstable when exposed to water and moisture. Exposure of isocyanate groups to water or moisture (or other compounds) can lead to the decomposition of the groups, cross-linking of polymers to which they are attached, and release of carbon dioxide, as shown below for a model lysine isocyanate:

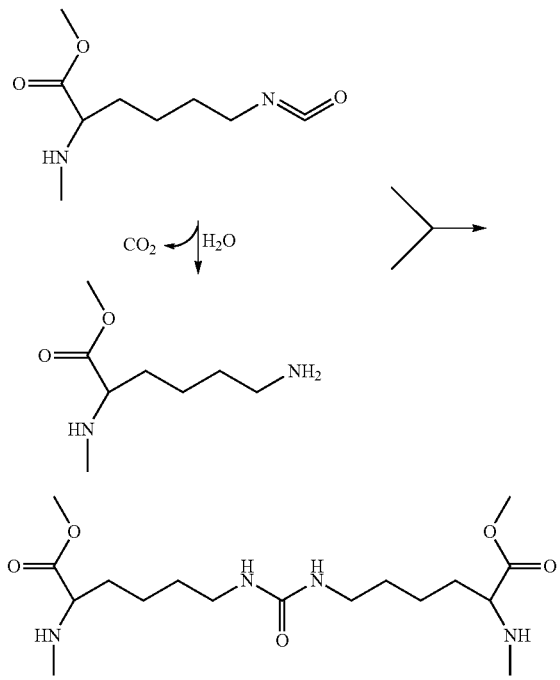

In the mechanism above, the isocyanate is partially hydrolyzed to produce amines, which can react with native, non-hydrolyzed isocyanates, as shown above. Not wishing to be bound by any theory, a cross-linked structure can be produced because the rate of the amine-isocyanate reaction may be on the order of or faster than the rate of isocyanate hydrolysis, and inter-chain reactions occur between these functional groups to ultimately form a cross-linked structure. The isocyanates on the polymer can also react with amine groups of the tissue (e.g. lysines in proteins), which can form a covalent bond with the tissue to further strengthen the seal at sites in which fluid is being lost (e.g., at bleeding sites). In addition, the isocyanate hydrolysis reaction produces $CO_2$, enabling simultaneous cross-linking and gas production in a single-reaction scheme.

In certain embodiments, polyurethane foams may be generated by cross-linking polyols with multifunctional isocyanates. Polyols suitable for use in such embodiments include polyether- and polybutadiene-based polyols. Polyols of particular interest include polypropylene glycol (PPG) and polyethylene glycol (PEG), as well as random and block copolymers thereof. Also suitable for use are polycarbonates, polybutadienes, and polyesters. Diols, triols, and tetrols are most preferred, but multifunctional polyols with any suitable number of arms may be used. Molecular weights between 100 and 10,000 Da are preferable, with molecular weights up to 6,000 Da being most preferred, and blends of polymers with different molecular weights, degrees of branching, and composition are often used. Commercial polymers of particular interest include polypropylene glycols (425, 1200 Da), polyethylene glycols (200, 400, 600, 1000, 2000, 3000 Da), Pluracol products (355, 1135 i, 726, 816), Arch Poly-G 30-240, Poly-G 76-120, Poly-G 85-29, trimethylolpropane ethoxylate (450, 1014 Da), pentaerythritol ethoxylate (797 Da), UCON 75-H-1400, UCON 75-H-9500, dipropylene glycol, diethylene glycol, tripropylene glycol, triethylene glycol, tetrapropylene glycol, and tetraethylene glycol. In preferred embodiments, polyols used in the present invention have a polyethylene oxide content of 0-50 wt %, more preferably 0-40 wt %, more preferably 0-30 wt %, more preferably 0-25 wt %, and most preferably 0-16.5 wt %. Also preferred is that polyols used in the present invention comprise an amine catalyst in an amount up to 10 pphp, a water content of up to 20 pphp, a surfactant in an amount up to 10 pphp, and a diluent up to 300 pphp (preferably up to 250 pphp and most preferably up to 15 pphp). Examples polyurethane foams generated by cross-linking polyols with multifunctional isocyanates, in accordance with the present invention, are listed in Table 7.

Isocyanates suitable for use in such embodiments include any polymeric isocyanate with a degree of functionality greater than 2.0, with the most useful range being 2.0-2.7. Preferred polymeric isocyanates are based on methylene diphenyl isocuanate (MDI). Isocyanate true-prepolymers and quasi-prepolymers may also be used. In this case, a "quasi-" prepolymer, or semi-prepolymer, is a polymer formed by the reaction between a multifunctional isocyanate and polyol, where the isocyanate-to-alcohol ratio is greater than the stoichiometric two-to-one ratio. A "true-" prepolymer, or strict-prepolymer, is a polymer formed by the reaction between a multifunctional isocyanate and polyol, where the isocyanate-to-alcohol ratio is equal to the stoichiometric two-to-one ratio.

In some instances, it may be advantageous to position isocyanate groups in the polymer so that it is accessible for hydrolysis and cross-linking, without inhibiting binding to the tissue (e.g., damaged blood vessels). In one set of embodiments, a lysine group in the targeting peptide can be converted to an isocyanate by reaction with diphosgene. In some instances, the isocyanate and peptide chemistries can be completely decoupled by modifying a fraction of the side chains with peptide while the balance are modified with isocyanate.

The polymer that is foamed to form the polymer foams described herein may be formed using a variety of chemistries. In some embodiments, the polymer comprises a synthetic polymer. As used herein, a "synthetic polymer" refers to a polymer that is a product of a reaction directed by human interaction. For example, synthetic polymers can include polymers synthesized by reactions of natural or synthetic monomers or combinations thereof that are directed by human interaction. The formation of synthetic polymers can also include chain elongation of natural or synthetic polymers. In some embodiments, the synthetic polymer is not found in nature. In other cases, the synthetic polymer can be found in nature, but the polymer is synthesized via human interaction (e.g., in a laboratory setting). In some embodiments, the polymer may comprise a poly alpha-hydroxy acid. In some cases, the polymer may comprise a polyester. In some cases, the polymer may comprise a polyether-polyester block copolymer. In some cases, the polymer may comprise a poly(trimethlyene carbonate). In some embodiments, the backbone of the polymer can exclude at least one of polynucleotides, proteins, and polysaccharides.

In some embodiments, the polymer foam is formed by cross-linking a condensation polymer of a polyol and a polyacid. The terms "polyol" and "polyacid" are given their standard meanings in the art, and are used to refer to compounds comprising at least two alcohol groups and at least two acidic groups, respectively. Examples of polyols suitable for use in forming the condensation polymer used to form the polymer foams described herein include, but are not limited to, glycerol, polyethylene glycol, polypropylene glycol, polycaprolactone, vitamin B6, erythritol, threitol, ribitol, arabinitol, xylitol, allitol, altritol, galactritol, sorbitol, mannitol, iditol, lactitol, isomalt, and maltitol, wherein the functional groups present on the polyol are optionally substituted. Examples of polyacids suitable for use in forming the condensation polymer used to form the polymer foams described herein include, but are not limited to, succinic acid, fumaric acid, a-ketoglutaric acid, oxaloacetic acid, malic acid, oxalosuccinic acid, isocitric acid, cis-aconitic acid, citric acid, 2-hydroxy-malonic acid, tartaric acid, ribaric acid, arabanaric acid, xylaric acid, allaric acid, altraric acid, galacteric acid, glucaric acid, mannaric acid, dimercaptosuccinic acid, oxalic acid, malonic acid, succinic acid, glutaric acid, adipic acid, pimelic acid, suberic acid, azelaic acid, sebacic acid, malic acid, or vitamin B5, wherein the functional groups present on the polyacid are optionally substituted.

In some embodiments, the condensation polymer may comprise poly(glycerol-sebacate) (PGS). An exemplary synthesis pathway in which glycerol and sebacic acid are used to form PGS is shown below:

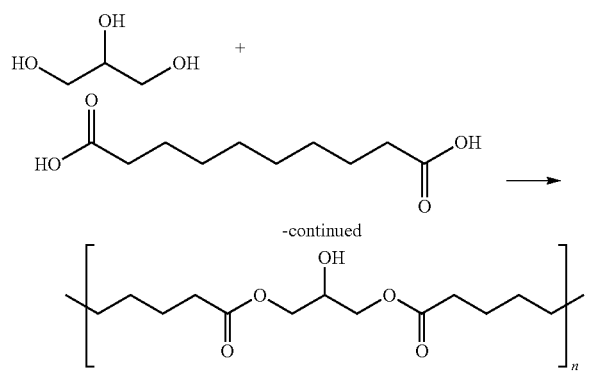

In some embodiments, the polymer foam is formed by cross-linking a polymer comprising the following formula (I):

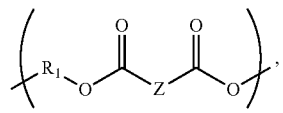

wherein R1 and Z can be the same or different and each is an alkyl, heteroalkyl, alkenyl, heteroalkenyl, alkynyl, heteroalkynyl, aryl, heteroaryl, heterocycle, acyl or carbonyl group, any of which may be optionally substituted, and wherein n is an integer greater than 1. In some embodiments, R1 and/or Z are substituted with a gas producing group. For example, R1 and/or Z may be substituted with a $CO_2$-producing group (e.g., isocyanate).

In some embodiments, the polymer can comprise cross-linking a polymer comprising the formula (II):

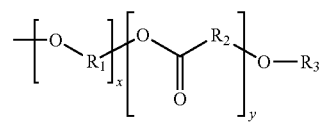

wherein R1 and R2 can be the same or different and each is an alkyl, heteroalkyl, alkenyl, heteroalkenyl, alkynyl, heteroalkynyl, aryl, heteroaryl, heterocycle, acyl or carbonyl group, any of which may be optionally substituted; wherein x and y are non-negative integers; wherein R3 may be a hydrogen, gas generating functional group, or tissue binding domain.

In some embodiments, the polymer may comprise the poly(lactic acid) (PLA), poly(glycolic acid) (PGA), and polycaprolactone (PCL) class of polymers and their copolymers, such as poly (lactate-co-caprolactone) or poly (glycolate-caprolactone). Copolymerization of the lactide, glycolide and caprolactone monomers in various ratios can yield materials with a wide range of mechanical properties, thermal characteristics and degradation times. The structure of the PLA/PGA/PCL copolymers (and associated properties such as molecular weight, etc.) can be tailored, in some cases, by adjusting the type of initiator used and its molar ratio with the monomer(s).

In some embodiments, the polymer comprises poly(glycolate caprolactone). In some cases, the PGCL composition includes a ratio of glycolide to caprolactone of about 50:50. An exemplary synthesis pathway for PGCL is shown below, in which pentaerythritol is used as an initiator to form 4-armed, branched structures.

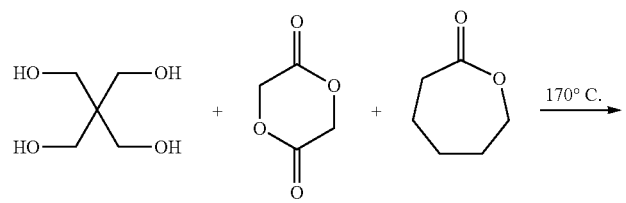

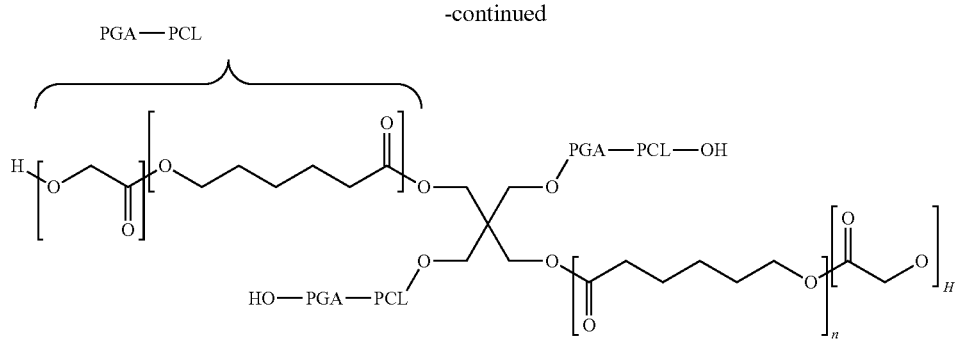

15

The properties of the polymer used to form the polymer foam may be tailored to achieve a desired result. For example, is some embodiments, the viscosity of the polymer is tailored such that the polymer formulation is better able to permeate the vasculature perforation and create conformal contact with the perforation and/or the medical device placed within the vasculature. An overly viscous polymer formulation may require excessive pressure to deploy within the vasculature perforation. In addition, an overly viscous polymer formulation may inhibit the polymer from accessing interstitial spaces. An overly low-viscosity polymer formulation might be difficult to contain the material to the injured site or may be displaced by the flow of a bodily fluid. One of ordinary skill in the art will be able to produce the desired viscosity for a given polymer type by, for example, adjusting the molecular weighty of the polymer. In some embodiments, the viscosity and the molecular weight are related through a power law. The molecular weight of a polymer may be adjusted by, for example, controlling the time of the polymerization reaction used to generate the polymer. In some embodiments, the molecular weight of the polymer is between about 1000 and about 10,000 g/mol or between about 1200 and 6000 g/mol. The viscosity of the formulation may be adjusted by, for example, adding diluents such as any suitable low molecular weight, low viscosity compound, examples of which include triacetin, propylene carbonate, tetraethylene glycol dimethyl ether, dimethyl esters of diacids (e.g., diethyl malonate, dimethyl adipate), dimethyl sulfoxide, and oils (vegetable, olive, castor, etc.). In some embodiments, the polymer is amorphous or semi-crystalline with a glass transition temperature (Tg) below room temperature. Such properties yield, is some cases, polymers with sufficiently low viscosities that they can be dispensed from an external container via pressure-driven flow.

In some embodiments, properties or composition of the polymer may be chosen to achieve a desired hydrophilicity or hydrophobicity. The hydrophilicity of the polymer may be selected, in some instances, such that the surface (e.g., tissue surfaces) within a vasculature perforation are appropriately wetted. Generally, a material with increased hydrophilicity will have a greater tendency to wet soft tissues surfaces and to react more quickly because of better mixing with blood. However, the polymer and resulting polymer foam may be, in some cases, somewhat hydrophobic such that they do not dissolve into biological fluids. Appropriately hydrophilic polymers are capable of conformably wetting interior surfaces of a vasculature perforation while remaining contained within the cavity. In some embodiments, the composition of the polymer may be selected to achieve a desired hydrophilicity. For example, in some embodiments, the chain length of a monomer used to synthesize the polymer can be varied to change hydrophilicity. As a specific example, the carbon chain length between carbonyl groups of a diacid monomer can be varied from between two and eight aliphatic carbons, producing a range of hydrophilicity in the resulting polymer. A more common example for modulating hydrophilicity may be to generate a co-polymer composed of some hydrophilic and some hydrophobic monomers.

In some embodiments, the polymer foams described herein may have favorable mechanical properties. In some embodiments, the polymer foams are elastomeric. The term "elastomer" as used herein, refers to a polymer that can return to the approximate shape from which it has been substantially distorted by an applied stress. In some cases, the elastomeric polymer foams described herein may comprise a polymer having a bulk modulus of between about 0.05 MPa and about 10 MPa; 0.05 MPa and about 100 MPa; and 0.05 MPa and about 500 MPa. Elastomeric polymers may be particularly suitable for use in making polymer foams because they are capable sustaining stress without permanently deforming, while providing adequate support for body organs and tissues.

Additionally, the density of the formulation or polymer foam may be purposely manipulated. In some embodiments, the formulation and/or polymer foam will have a density less than that of blood, such that it will rise to the top of the sac during filling. Alternatively, the formulation and/or polymer foam might have a density greater than that of blood such that it will fall to the bottom of the sac. The density of the formulation may ho manipulated by incorporating gas or addition of fillers or additives (e.g., tantalum) or other techniques known to those in the art.

The time required to form the polymer foam after exposure of the formulation to the vasculature perforation and the final mechanical and physicochemical properties of the polymer foam can depend on such factors as the composition of the polymer and its hydrophobicity, the density of pendant groups (e.g., cross-linking groups), relative positions of the pendant groups (e.g., cross-linking groups), and other factors.

In some embodiments, the polymer or polymer foam may be biodegradable. As used herein, "biodegradable" describes materials that are capable of degrading down to oligomeric or monomeric species under physiological or endosomal conditions. The phrase "physiological conditions," as used herein, relates to the range of chemical (e.g., pH, ionic strength) and biochemical (e.g., enzyme concentrations) conditions likely to be encountered in the intracellular and extracellular fluids of tissues. In some embodiments, the physiological pH ranges from about 7.0 to 7.4. In some embodiments, biodegradable materials are not hydrolytically degradable but can be fully degraded via enzymatic action to fully degrade. In some cases, biodegradable materials are hydrolytically or enzymatically degradable, or combinations thereof. In some embodiments, the polymer or polymer foam is biodegradable, but it does not biodegrade over the time scale in which it is located within a vasculature perforation. In such cases, the polymer foam can remain structurally stable while being inserted into the vasculature perforation, while ensuring that any remnants of the polymer foam that remain within the vasculature perforation after removal can be biodegraded. For example, in some embodiments, the biodegradable polymer foam does not significantly biodegrade within the body cavity prior to removing the foam via surgical intervention.

The polymer or polymer foam may be biocompatible, in some instances. One of ordinary skill in the art can determine biocompatibility based upon the ISO-10993 standard. For example, PGS is known to satisfy the ISO-10993 standard for biocompatibility. In some embodiments, chemical modifications (e.g., attachment of a pendant group, etc.) to the PGS backbone do not alter its biocompatibility. In some embodiments, a polymer that produces known, but acceptable levels of inflammation may be used. Examples of such polymers include poly-alpha-hydroxyacids (e.g., polylactide, polyglycolide, and polycaprolactone) and poly(trimethylene carbonate).

The polymeric foams described herein may be used, in some embodiments, to prevent or limit the movement of a bodily fluid within the vasculature perforation or other bodily cavity, relative to an amount of movement of bodily fluid that would occur under essentially identical conditions in the absence of the polymer foam. "Essentially identical conditions," in this context, means conditions that are similar or identical other than the presence of the polymer foam. For example, otherwise identical conditions may mean that the vasculature perforation or other bodily cavity is similar or identical, the conditions within the cavity are similar or identical, but where no polymer foam is located within the vasculature perforation or bodily cavity. In some embodiments, the polymer foam may be used to reduce the movement of blood or other bodily fluid within a vasculature perforation or bodily cavity. The polymer foams may also be used to prevent or limit the movement of interstitial fluid, or any other suitable fluid. In some embodiments, preventing or limiting the movement of bodily fluid comprises immobilizing and/or stabilizing blood clots.

Preventing or limiting the movement of a bodily fluid may comprise, in some instances, the movement of bodily fluids into the cells of the polymer foam. Such movement of fluid into the cells may aid in the formation of, for example, blood clots or other stabilizing structures within the foam.

The movement of bodily fluids may be prevented or limited over a relatively long period of time. For example, in some embodiments, the polymer foam can prevent or limit movement of a bodily fluid within the vasculature perforation or body cavity for at least about 3 hours, at least about 6 hours, at least about 12 hours, at least about 24 hours, at least about 3 days, or at least about 1 week.

In some embodiments, the movement of bodily fluids may be prevented or limited via the application of pressure. For example, the formation of the polymer foam may involve volumetric expansion of the polymer. In some embodiments, the expansion of the polymer may result in the application of a pressure to a surface within the vasculature perforation or bodily cavity, potentially forming and improving the seal.

In some cases, the movement of bodily fluids may be prevented or limited due to a physical seal created between the arterial wall or collateral vessel walls and the surface of the foam. This seal may be due to pressure and/or chemical bonding between the tissue surface and foam and/or the highly conformal contact of the foam with the tissue surfaces combined with the foam's tendency to induce coagulation of blood. In addition, the foam may penetrate collateral vessels within the vasculature perforation to further limit blood flow into the sac. Preferably in-situ expansion of the foam in combination with formation of the skin or coil leads to penetration of these collateral vessels by less than about 2 cm. In some cases, the polymer may be designed to cross-link quickly, for example, by tailoring the polymer to have functional groups that crosslink quickly, by adding catalysts, or by other known means. Suitable catalysts for use in embodiments of the present invention include amine based compounds, preferably tertiary amines, triethylenediamine (TEDA, DABCO, DABCO 33-LV), bis(2-dimethylaminoethyl)ether (Niax A1), trimethylaminoethyl-ethanolamine, 1,2-dimethylimidazole. In addition, the pores of the foam can trap blood and allow it to coagulate in stagnant areas. In some cases, the movement of the stent or another medical implant (stent migration) may be minimized due to the encapsulation of such a device by the foam. The foam may be used to surround and reinforce the device, increasing mechanical robustness (allowing for thinner, intrinsically weaker stent design). In addition, the rate at which the amount of bleeding is reduced can be controlled by adjusting the amount of reactive pendant groups.

In addition to gas-forming pendant groups, other active agents may also be included as pendant groups on the polymer. For example, the polymer foam can include groups used to stimulate desirable cellular responses such as fibroplasia, angiogenesis and epithelialization. Similarly, the mechanical structure and mechanical properties of the foam itself may elicit these properties. In some embodiments, the polymer or polymer foam may be covalently bonded to a surface within the vasculature perforation, for example, through a pendant group.

In some embodiments, the polymer or cross-linked product may comprise at least one pendant group that can bind to tissue or injured tissue (e.g., inflamed tissue, bleeding tissue, a wound site, etc.) within the vasculature perforation. The binding of the pendant groups to the tissue or injured tissue can be covalent or non-covalent. The tissue or injured tissue may comprise one or more molecules that would not be present in or near uninjured tissue as is the case, for example, when subendothelial surfaces are exposed. By including such pendant groups, a polymer or cross-linked product could be made that selectively binds to tissue or injured tissue, in comparison to uninjured tissue. Such binding may limit or prevent the movement of bodily fluid within the vasculature perforation, in some embodiments. Examples of chemicals that may be targeted by pendant groups on the polymer or polymer foam include, for example, von Willebrand Factor, collagen (e.g., collagen I and IV), a fibroblast growth factor, laminin, elastin, localized coagulation factors in their activated form (e.g., fibrin, thrombin, factor Xa, etc.), among others. Example of types of pendant groups that may be bound to the polymer or polymer foam for such uses include, for example, peptides, carbohydrates (e.g., oligosaccharide sequences), aptamers.

One of ordinary skill in the art will be able to identify other compounds in tissue or injured tissues and perform screening tests to determine suitable pendant groups that could be used to bind with those compounds. For example, in vivo screening, for example by phage display technology, of a large library of possible pendant groups (e.g., permutations of peptide sequences fused to a phage surface protein, a collection of carbohydrate molecules, etc.) could be performed (e.g., in rodents) to identify pendant groups that bind specifically to wounded organs. The pendant group could then be identified (e.g., via sequencing for peptides) from each organ. For example, a sequence that appears in all organs or injured organs could be identified.

Subsequent testing (e.g., in vivo testing in uninjured animals) could be performed to verify that the pendant group does not bind to tissue in the absence of injury.

In some cases, human protein targets can be used to find pendant groups that bind selectively to the injured site. For example, human fibrin, which is generally present where injuries to blood vessels have occurred, can be used for screening, potentially mitigating the risk present in the in vivo approach where there could be sequence and conformational differences between animal and human targets. Binding levels to fibrin can be assessed using, for example, fluorescently tagged molecules, and compared against, for example, fibrinogen, a precursor of fibrin that is ubiquitous in blood plasma. The pendant groups showing highest selectivity to fibrin over fibrinogen could be selected for use in the polymer composition.

In addition to targeting tissues or injured tissues, pendant groups may be used to stabilize tissue or injured tissue. For example, pendant groups (e.g., $CO_2$-forming groups) may covalently bond to tissue, in some cases, which may lead to be sealing of one or more openings within a vasculature perforation. Such binding can aid in limiting or preventing the movement of bodily fluid within the vasculature, in some cases. In some embodiments, the concentration of isocyanate in the polymer or a cross-linked product can affect the extent to which binding between the polymer and tissue occurs. Specifically, increasing the isocyanate levels can serve to increase and reinforce the polymer-tissue contact area, potentially producing a stronger and longer-lasting seal. Increasing the level of isocyanate in the polymer can also increase the crosslink density, potentially resulting in a more rigid material that may break more easily at the polymer-tissue interface (e.g., when the body is moved). Therefore, the concentration of isocyanate may be selected, in some cases, to balance between these two effects.

In another embodiment, the polymer properties are selected such that minimal covalent binding of the foam to tissue is observed. The foam, however, can be bound to tissue by different non-covalent forces, such as electrostatic, Van der Waals, or capillary. Minimal covalent binding of foam to tissue can facilitate easy foam removal and prevent adhesions, such as abdominal adhesions, during the healing process.

In some cases, non-isocyanate pendant groups may be used to stabilize the polymer-tissue interface. For example, the polymer may comprise aldehyde reactive groups, which can be used, for example to bind tissue proteins. Aldehyde groups may be attached by, for example, attaching ethanolamine to the polymer, followed by oxidizing the pendant hydroxyl group to form an aldehyde group. In some instances, pendant groups that selectively bind to fibrin may be used to stabilize the clot-polymer interface. In addition, pendant groups may be selected that compete with plasminogen and its activators for fibrin binding sites, blocking the activation of fibrynolytic cascade.

In some embodiments, the polymer (or the compounds used to make the polymer) are chosen such that they comprise one or more pendant hydroxyl groups. The hydroxyl groups may serve, for example, as sites at which pendant groups are attached to the polymer. For example, glycerol and sebacic acid both contain hydroxyl groups that may be used to impart functionality to PGS. As a specific example, pendant peptides can be introduced onto polymers using a two-step reaction scheme in which the polymer hydroxyl groups are first activated with carbonyldiimidazole (CDI) and then coupled to the amine-terminus of the peptide, as shown below. This chemistry can result in high coupling efficiencies.

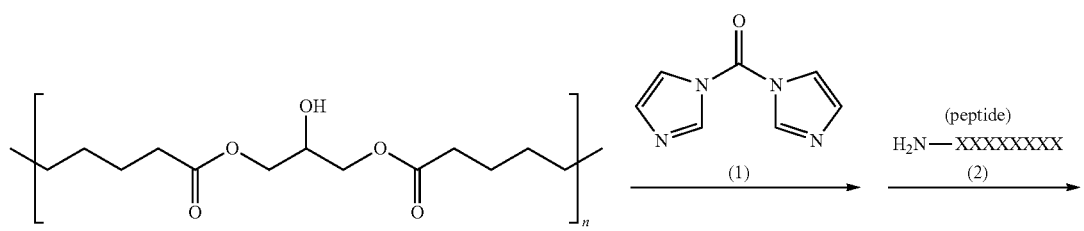

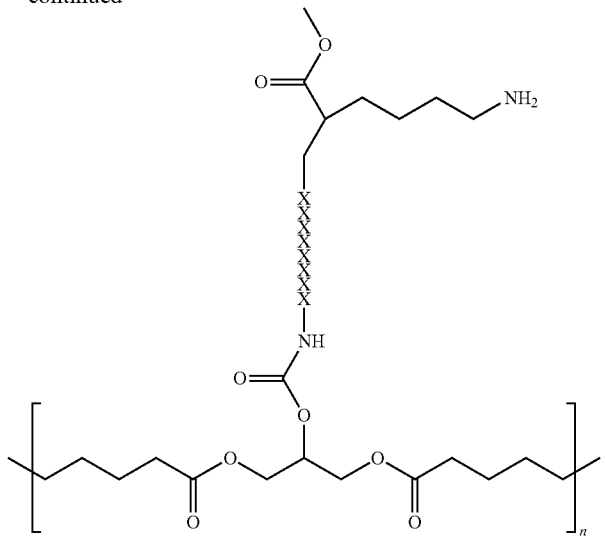

-continued

In some instances, a drug may be delivered to the vasculature perforation with the formation. In some embodiments, the formulation may comprise a drug. For example, a drug (or a plurality of particles containing one or more drugs) may be dispersed within the formulation. Example of such drugs include, but are not limited to, antifibrinolytic compounds (e.g., aminocaproic acid, tranexamic acid, etc.), anti-fibrotic compounds, antimicrobial compounds (e.g., antibiotics), anti-inflammatory compounds, analgesics, procoagulant compounds, statins, growth factors, and vasoconstrictors. Drugs that comprise amine groups may, in some cases, be isolated from isocyanates within the formulation, for example, to prevent unwanted reaction during the cross-linking step. Isolation can be achieved by encapsulating drugs into secondary particles and loading them into the formulation at the time of delivery to the vasculature perforation. In addition, encapsulation may be used to release the drugs at a controlled rate. In some embodiments, a drug may be incorporated into a fiber, which may be included in the formulation. The drug release rate from the fiber can be controlled by varying composition and structure (e.g., thickness or other dimension, presence of sheath) of fiber. For example, the fiber can be designed to deliver an initial burst release shortly after the deployment of the formulation, followed by sustained delivery (e.g., over the time period in which the formulation foam will be left in the vasculature).

The formulation may be combined with a second agent (and, optionally, a third agent, fourth agent, etc.), in some cases, before or after the formulation is transported to the vasculature perforation. The second agent may comprise, for example, a compound that accelerates at least one of cross-linking and foaming, relative to a rate of at least one of cross-linking and foaming that would have occurred in the absence of the second agent. For example, in some embodiments, the second agent may comprise an amine (e.g., a polyamine). The amine compound may serve to increase the rate at which the formulation cross-links, which may also reduce the amount of time required to reduce or eliminate the movement of a fluid (e.g., blood) within the vasculature perforation. The second agent may comprise, in some cases, at least one of lysine, spermine, spermidine, hexamethylenediamine, polylysine, polyallylamine, polyethylenimine, and chitosan. In some cases, the second reagent may comprise a carbonate or a bicarbonate which may be used, for example, to produce $CO_2$ gas in-situ, as described above. In some embodiments, the second reagent can comprise an acid which may be used, for example, as a reactant in the $CO_2$-producing reaction. The acid functionality may comprise, for example, a carboxylic acid pendant group attached to a polymer chain or blended with a polymer to form a mixture. In some cases, the second reagent can be native in the body (e.g., bicarbonate in the blood). In other cases, the second agent may originate from outside the vasculature perforation. For example, the second agent may be, for example, supplied to the vasculature perforation along with the formulation.

In some embodiments, the combination of the second agent with the formulation produces a polymer foam with significantly different mechanical properties (e.g., elastic modulus, yield strength, breaking strength, etc.) than would have been produced in the absence of the second agent. For example, addition of the second agent may lead to increased cross-linking among polymer molecules, potentially producing a stiffer foam. In another embodiment, the second agent may have a high molecular weight, such that the distance between crosslinks is high, and the resulting foam is softer.

The combination of the second agent with the formulation may, in some embodiments, prevent or limit the flow of blood into the vasculature perforation, relative to an amount of blood flow that would occur under essentially identical conditions in the absence of the second agent. In some embodiments, blood flow may be reduced due to the increased rate of cross-linking or foaming mentioned above. In some cases, the second agent may comprise a pro-coagulant coagulant compound (e.g., thrombin, fibrinogen, factor X, factor VII, kaolin, glass, chitosan, or other hemostatic agent).

In some embodiments, the expandable member includes the second agent may be stored in a container separate from the formulation, for example a separate balloon, to prevent unwanted reaction between the formulation and the second agent outside the vasculature perforation. In some embodiments, a container can be used that keeps the formulation and the second agent separated while stored or transported, but allow for mixing at the distal end of the expandable member or within the vasculature perforation when the contents are expelled. The container may also be designed to mix the components immediately prior to dispensing by breaking the barrier between each of the components and allowing them to mix.

In another embodiment, additives can be added to the formulations that absorb heat if generated during the crosslinking reaction. For example, materials in the form of micro or nanoparticles, spheres or fibers can absorb the heat by undergoing a phase change (e.g. melting) or glass transition and thereby reduce the heat absorbed by biological tissues. For example, biodegradable fibers made of poly caprolactone can melt at ~60° C., absorbing the generated heat and reducing tissue damage.

In some embodiments, the vasculature perforation can be imaged. The ability to image the vasculature perforation can allow for proper dosing, efficient localization and repair of an injury, stabilization of a wound, etc. In some embodiments, contrast agents can be incorporated into the formulation. In other embodiments, pendant groups on the polymer or polymer foam can be utilized to aid in imaging the vasculature perforation, for example, a contrast, agent can be introduced into the blood stream, of a subject in which the vasculature perforation is located, and the contrast agent may be capable of selectively binding to pendant groups of the polymer. Examples of contrast agents include, for example, colored, fluorescent, or radio-opaque imaging entities. Examples of radio-opaque imaging entities include, for example, barium-based substances, iodine-based substances, tantalum powder, tantalum oxide powder, tantalum-based substances, and zirconium dioxide. In another embodiment the foam itself provides sufficient radio contrast to surrounding tissues to facilitate visualization. For example, gas bubbles or gas-filled pores may provide contrast upon imaging with ultrasound. In some embodiments, the contrast agents emit electromagnetic radiation in the near-infrared image (e.g., about 700 to about 1000 nm) upon interacting with the polymer foam. As a specific example, quantum dots (QD) may be used as contrast agents. In some cases, fluorescent organic tags (e.g., fluoroscein isocyanate) or radio-opaque chelating groups (e.g., Gd3+) can be used with appropriate imaging equipment. In another example, the contrast agents listed above may be attached as pendant groups to the polymer or dispersed in the polymer to aid in visualization. In another example, tantalum, titanium or barium sulfate powder may be physically mixed with the polymer for visualization. To provide a time-dependent contrast, the foam may include bio-erodible particles or fibers which include the contrast agent. Following exposure to a physiological environment, the particles or fibers will erode and release the contrast agent which can then be eliminated from the implant site. This can provide implants which become less radio-opaque, for example, over time post-delivery. This may be advantageous to users who want to evaluate location of the foam for some time after implantations but then do not desire to have a radio-opaque foam providing imaging artifacts which limit assessment of surrounding tissues. Preferably the radio-opacity will decrease substantially within three months of implantation.

A variety of mechanisms can be employed to remove polymer or polymer foam from the body cavity or from placement on tissue. In some embodiments, at least part of the polymer foam is removed via surgical intervention. For example, the polymer foam may be cut out of the body cavity, in some instances. In some cases, surgical intervention may be sufficient to remove the bulk of the polymer foam material (e.g., at least about 80%, at least about 90%, etc.) from the body cavity. The polymer or the pendant groups bonded to the polymer may be selected, in some cases, such that the resulting polymer foam can be removed from a body cavity. In some embodiments that employ a biodegradable polymer or polymer foam, the foam or the remainder of the foam after surgical removal may biodegrade over time.

In some embodiments, the foam may be degraded by applying an external stimulus to the foam. Such methods may be useful, for example, when some polymer or polymer foam material remains physically inaccessible after surgical removal due to, for example, deep tissue penetration. Examples of external stimuli that may be applied to degrade the polymer foam include, but are not limited to, UV radiation, heat, or a chemical (e.g., a chemical introduced into the blood stream of a subject in which the body cavity is formed).

Degradation of the polymer foam may be achieved, in some cases, via reversible crosslinks in the polymer or polymer foam. In some cases, the type of cross-link or external stimulus type can be selected such that the polymer foam is selectively and controllably depolymerized. Upon reversion to the uncrosslinked state, the polymer or polymer foam can, in some cases, be removed from the cavity using, for example, saline.

Reversible cross-linking can be accomplished by, for example, modifying a pendant group of the polymer to include bis(2-isocyanatoethyl)disulfide. Such chemistry may be particularly useful, for example, when isocyanate chemistry, which may not be reversible using the external stimulus of choice, is used to foam the polymer. The disulfide group can be readily cleaved with, for example, glutathione. In this example, the sulfur-sulfur bond can be broken through a disulfide exchange reaction, enabling selective cleaving at the disulfide bonds by application of, for example, a glutathione solution. As another example, cinnamic acid groups can be attached to the polymer such that reversing the cross-links can be accomplished by application of UV light.

All polymer formulations described are contemplated for use in preventing tissue adhesions. A preferred embodiment utilizes PGS as a component of the foam. A more preferred embodiment includes isocyanate-functionalized PGS that cures in the presence of body water. In this embodiment, interchain hydrogen bonding results in an increase in modulus. In another embodiment water may be mixed with the isocyanate-functionalized PGS during administration to facilitate curing. In another embodiment, the isocyanate-functionalized PGS is mixed at the time of administration with a polyamine (e.g. lysine, PEG-amine). This polyamine acts as a curing or crosslinking agent. Variation in the amount of polyamine and/or type of polyamine used enables control of mechanical properties of the cured polymer.

In another embodiment, PGS acts as a polyol and can be mixed with an isocyanate containing compound to form a crosslinked foam. In these cases, foam formation is obtained and enhanced by mixing gas into the formulation to create pore nucleation sites, or by adjusting the levels of surfactants that stabilize the foam pores during their formation and expansion.

In other embodiments, the polymer does not foam or foams minimally allowing for flow over the tissue surfaces. This allows for curing into a gel coating. In these cases, PGS is crosslinked under conditions that minimize foam formation by limiting or preventing gas into the formulation and/or reducing the levels of surfactants resulting pore stabilization. In addition, PGS can be gelled or crosslinked by mixing with a component that does not generate a gaseous by-products upon reaction with PGS.

In yet other embodiments two or more different PGS polymers can be combined during administration. These polymers then react and crosslink into a gel or foam. The type and ratio of PGS polymers used impact the foaming, gelling, curing and mechanical properties.

In another embodiment drug-loaded objects are incorporated in the foam or gel at or before administration. Incorporation of drug-loaded objects into a polymer during administration is accomplished by those methods known to those skilled in the medical and pharmaceutical formulation arts. Examples of drug-loaded objects include: microspheres, microfibers, core-sheath microfibers, core-sheath nanofibers, nanoparticles, nanospheres, nanofibers or pure particles of drug. Preferably drug is released from these objects over a period of 7 days. More preferably the drug is released up to 14 days. Drug may be released for up to 30 days or longer. Preferably the kinetic release profile for the drug provides approximately the same dose of drug throughout a given period of time.

In certain embodiments, the invention relates to liquid formulations that are delivered to a body cavity and form foam implants in situ. The liquid formulation or formulations optionally include an entrained gas or a dissolved gas. In preferred embodiments, the resulting foam implant provides hemostasis when applied near one or more sites of hemorrhage. Foam implants of the invention are preferably biocompatible, bioabsorbable, can be removed from the body with standard surgical procedures, and do not induce adhesions.

In certain embodiments, the invention is a polyurethane foam that is formed in situ from a two-part formulation as previously described. The first part of the formulation includes an isocyanate compound such as hexamethylene diisocyanate (HDI), toluene diisocyanate (TDI), methylene diphenyl diisocyanate (MDI) or a mixture of MDI isomers, polymeric MDI, isocyanate-functionalized prepolymer, or a polymeric isocyanate having a functionality of preferably between 2.0 and 3.0. The second part of the formulation includes a hydroxyl-functionalized polymer (polyol). The preferred viscosity of the first and second parts of the formulation is 1 to 3,000 cP, and preferably about 2,400 to about 2,600 cP. The polyol phase optionally has multiple polyol species, catalysts, surfactants, chain extenders, crosslinkers, pore openers, fillers, plasticizers and water. Air, carbon dioxide or other auxiliary blowing agents are optionally entrained into either the isocyanate or polyol phases prior to delivery to the patient or, alternatively, are introduced during delivery as a component of the formulation.

In some embodiments, the foam is formed by a fast cross-linking reaction that can be surface triggered by in-situ water. Multi-functional moisture sensitive silanes are one example of materials susceptible to such reactions especially when formulated with tin, titans or other metal-organic catalysts. One-part cross-linking systems can be created by a two-step process. In the first step, hydroxyl containing siloxanes (either silanols or carbinols) are reacted with an excess of multifunctional silane containing acetoxy, oxime, alkoxy (e.g., methoxy, ethoxy), isopropenoxy, amide amine, aminoxy, or other functional groups containing silane with the hydrolytically susceptible Si—O—C bond. The resulting prepolymers have multiple groups that are susceptible to hydrolysis. In the second step, such prepolymers are exposed to in-situ water to result in a rapidly cross-linking elastic solid. The reaction proceeds from the outside-in, resulting in a quickly formed outer skin and, in some cases, the formation of the foam into a coil-like configuration. The slower permeation of water or alternative reaction trigger can be used to slowly cure the material inside of the skin. The proteins and pH of the blood can be used to support coil formation by modifying the rate of the skin-forming reaction as well as in coating the formed coil and preventing coil sticking and agglomeration upon self-contact.

Additionally, hydride functional (Si—H) siloxanes or isocyanate functionalized carbinols can be introduced into silanol elastomer formulations to generate gas and produce expanding foamed structures. Expansion of the material can be used to increase the size of the formed coil effectively decreasing coil embolization potential. Expansion of the material can also be critical to increase material size without delivery of more material, in adding porosity and in generating sealing or pressure. Additional formulation ingredients such as surfactants can be used to the impact of generated gas on porosity and expansion.

In an alternative embodiment of this invention, acetic acid and sodium bicarbonate are mixed and caused to reach together in-situ to produce carbon dioxide as a blowing agent. An additional by-product of the reaction is water, which can accelerate an independent isocyanate gelling reaction.

Alternatively, isocyanate-containing prepolymers are a second example of materials that may be used to generate in-situ forming coils or lava-like foams. Isocyanate groups are relatively unstable when exposed to water and moisture. One-part isocyanate based cross-linking systems can be created by a two-step process. In the first step, polyols, diols, diamines, polyamines, diepoxides or polyepoxides are capped with aliphatic or aromatic diisocyanates such as isophorone diisocyanate (IPDI), dexamethylene diisocyanate (HDI) and methylene diphenyl diisocyanate (MDI). Additionally, multifunctional isocyanates such as HDI biuret, HDI trimer, and polymeric MDI can be combined with diols or diamines. The resulting prepolymers have multiple distant isocyanate groups that are able to react with water and amines found in blood. In the second step, such prepolymers are exposed to in-situ blood resulting in rapid cross-linking and foam formation. The reaction is water-triggered and proceeds from the outside-in, forming a porous outer skin, lava-like shell core structure that assists in coil formation. The expansion of such materials can be important in generating coils of a large diameter while maintaining a small cross-sectional area of the delivery device. Such materials can be used to form stand-alone foaming or gelling coils or combined with each other such that one material is coaxially formed on top of the other. For example, a coaxial delivery device can deploy a coil forming formation surrounded by a highly expandable coating formulation. The two formulations may be from different chemistry classes. Alternatively, the two formulations may be selected to be immiscible such that upon mixing together that the formulations phase separate (e.g., oil miscible and water miscible formulations) to naturally form a coaxial structure. Additionally, the interaction with the catheter wall and/or the density differential of the two fluids can be used to further drive the phase separation. Additionally, two-part formulations may be designed such that the two parts are not fully miscible. A surfactant system may be used to formulate the two part formulation into a single stable emulsion. Such an emulsion could be delivered via single chamber delivery device and does not require mixing. The emulsion can be destabilized by shear during delivery or in-situ factors (pH, temperature, ionic strength). Upon such destabilization, the internal phase of the emulsion would spill out and trigger the reaction with the external phase resulting in in-situ foam formation.

In other embodiments, particles or fibers are included in the foam formulation to result in a composite structure which provides desirable mechanical properties. For example, biocompatible polymer fibers may be included in the unreacted components. These fibers will distribute throughout the foam during in-situ expansion and become part of the structure upon crosslinking. These fibers can provide a more durable, stronger or higher modulus implant. Addition of space filling, highly-compliant particles or fibers may alternately provide a lower modulus, but also more durable implant. Inclusion of fibers which constrain the expansion of the foam may also prevent or limit foam expansion info collateral vessels in the vasculature perforation.

In another embodiment drug-loaded objects are incorporated in the formulation at or before administration. Incorporation of drug-loaded objects into a formulation during administration is accomplished by those methods known to those skilled in the medical and pharmaceutical formulation arts. Examples of drug-loaded objects include: microspheres, microfibers, core-sheath microfibers, core-sheath nanofibers, nanoparticles, nanospheres, nanofibers or pure particles of drug. Preferably drug is released from these objects over a period of 7 days. More preferably the drug is released up to 14 days. Drug may be released for up to 30 days or longer. Preferably the kinetic release profile for the drug provides approximately the same dose of drug throughout a given period of time.

Referring to FIGS. 23A and 23B, the in-situ forming foams of the present invention are delivered to a vasculature perforation or target site using any suitable delivery means. In certain embodiments, wherein balloons 2312 and 2314 each have a pressure strength at burst less than that of balloon 2304, expanding balloon 2304 causes the balloons 2312 and 2314 to break and release substantially simultaneously compositions 2316 and 2318 from balloons 2312 and 2314, respectively.

In other embodiments, expandable member 2302a, as shown in FIG. 23C, balloon 2312a may comprise a first plurality of micropores, and the balloon 2314a may comprise a second plurality of micropores. Upon expansion of balloon 2304, balloon 2304 contacts and applies pressure to balloons 2312a and 2314a, thereby causing the micropores in balloons 2312a and 2314a to expand and release substantially simultaneously composition 2316 and 2318 and composition 2318 through the micropores balloons 2312a and 2314a, respectively. In other words, balloons 2312a and 2314a may be semipermeable or include micropores. When balloon 2304 is in the unexpanded state, the micropores of balloons 2312a and 2314a are closed or small enough to effectively contain compositions 2316 and 2318. When balloon 2304 is in the expanded state, the micropores of balloons 2312a and 2314a open and/or increase to a sufficient size to release compositions 2316 and 2318.

Balloons 2312 and 2314 (or 2312a and 2314a) are pre-filled with first and second compositions 2316 and 2318, respectively, that may be the same or different. In other words, pre-filled balloon compositions 2316 and 2318 may be the same as in embodiments using a one-part foam formulation system wherein the compositions 2316 and 2318 combine with fluid present in the vessel at a vascular perforation site, for example. In other embodiments, pre-filled balloon compositions 2316 and 2318 are different to react with one another as when employing a two-part foam formulation system. Compositions suitable to be contained within balloons 2312 and 2314 include polymeric compositions, pre-polymer compositions combinable or reactable with aqueous solutions, or combinations thereof, examples of which have been previously described. In other embodiments, balloon 2304 includes an outer surface, wherein the outer surface is coated with a compositions that may be the same or different than compositions 2316 and 2318. In a certain embodiment, as shown in FIG. 23D, the outer surface of balloon 2304a is coated with a composition 2324 wherein composition 2324 is combinable with one of composition 2316, composition 2318, or both to form in-situ the biocompatible foam. Advantageously, occlusion balloon device 2302 is positioned at the site of or adjacent to a vascular perforation, and the perforation is occluded by being filled with a foam material formed in-situ at the perforation site by combining, interacting, reacting, or mixing compositions 2316 and 2318. In some embodiments, the foam generated in-situ fills the perforation to occlude the perforation in the superior vena cava, for example, thereby preventing or restricting blood loss, which could otherwise be life threatening.

In some embodiments, adhesive may be used to secure or otherwise attach the detachable, rigid balloons 2312 and 2314 to ends 2308 and 2310, respectively, of balloon 2304. The adhesive may comprise adhesives currently used in clinical settings, including, but not limited to, cyanoacrylates, bovine serum albumin (BSA)-glutaraldehyde, fibrin sealants, gelatin matrix thrombin, gelatin sponge, oxidized cellulose, collagen sponge, collagen fleece, recombinant factor VIIa, and the like. In some embodiments, the adhesive may comprise hydrophobic functional groups, such as hexanoyl (Hx; C6), palmitoyl (Pam; C16), stearoyl (Ste; C18), and oleoyl (Ole; C18 unsaturated) groups, so as to resist being washed out or disengaged from their substrate in predominately aqueous environments (e.g., vascular tissue). Such adhesives include, but are not limited to, 10Ole-disuccinimidyl tartrate, 10Ste-disuccinimidyl, and variations and combinations thereof.

FIGS. 23A and 23B are shown with inflatable balloon 2304 in at least a partially inflated state to show balloon 2304 impinging upon balloons 2312 and 2314 prior to balloons 2312 and 2314 releasing compositions 2316 and 2318. Expandable member 2302 further includes a catheter shaft 2306 wherein balloon 2304, balloon 2312 and balloon 2314 are carried by shaft 2306. FIG. 23B is a distal end view of expandable member 2302 along line B-B. FIG. 23B include a balloon device 2302, which is introduced to the perforation site via an optional introducer sheath 2320. Expandable member 2302, including optional sheath 2320 having an inner lumen 2322, wherein at least one of balloon 2304, balloon 2312, and balloon 2314 is moveable longitudinally within inner lumen 2322.

Figure 24C:
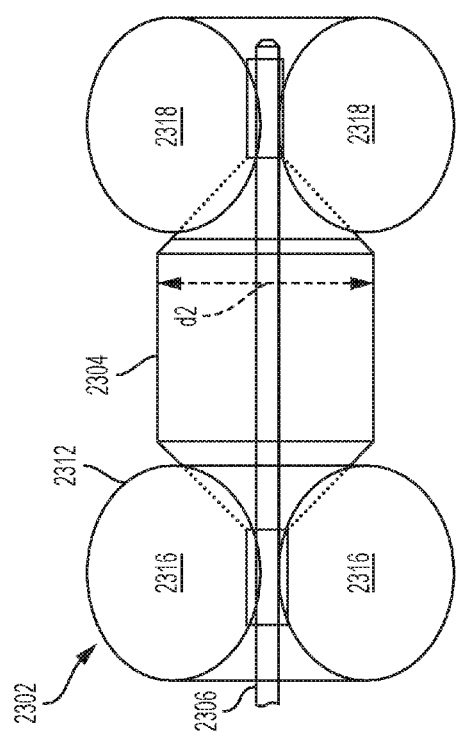
FIG. 24C is a side view of a distal portion of the expandable member of FIG. 23A in a second state wherein the inflatable balloon is in an inflated or expanded state.

FIGS. 24A-24E illustrate side views of the exemplary occlusion balloon device 2302 of FIGS. 23A-23B according to embodiments of the present disclosure. FIG. 24A is a side view of a distal portion of the expandable member of FIG. 23A in a deflated state wherein the inflatable balloon is an uninflated or unexpanded state. The deflated state may also be referred to as a resting or delivery state interchangeable herein. FIG. 24B is a side view of a distal portion of the occlusion balloon device 2302, wherein the expandable member 2302 is depicted in a first state wherein balloon 2304 is in a partially inflated or expanded state. The inflatable balloon 2304 includes a wall 2402 and an inflation chamber 2404, and diameter d1. The wall 2402 of the inflatable balloon 2304 defines the inflation chamber 2404.

Figure 24E:
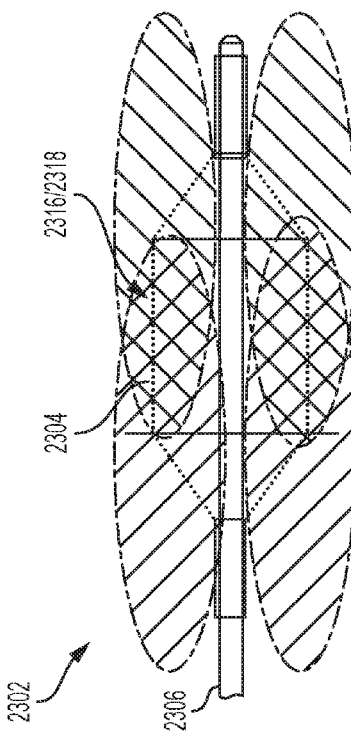
FIG. 24E is a side view of a distal portion of the expandable member of FIG. 23A in a fourth state or a combining state wherein the first and second compositions released from the rigid balloons are combined to form in-situ a biocompatible foam.
Figure 24D:
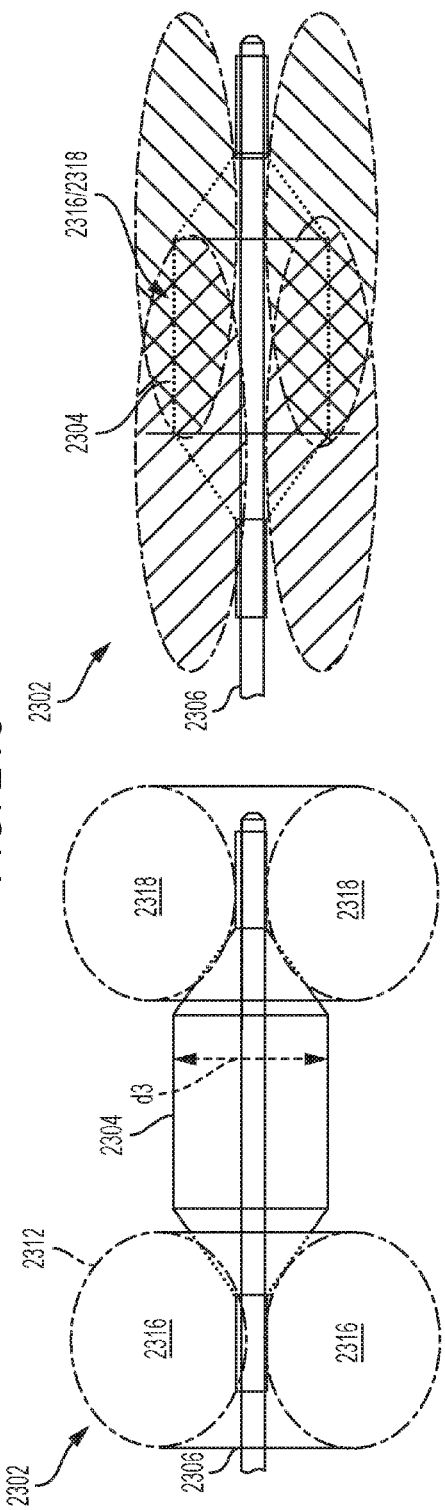
FIG. 24D is a side view of a distal portion of the expandable member of FIG. 23A in a third state wherein the rigid balloons containing first and second compositions are in a release state.

The inflation chamber 2404 is adapted to receive an inflation medium or inflation fluid that inflates the balloon. One non-limiting example of an inflation medium is about 80 percent saline (that is, 80 percent±5 percent) and about 20 percent contrast solution (that is, 20 percent±5 percent). The device 2302 is advanced, deployed, or otherwise positioned adjacent to the perforation or target site while in the resting or first state. Alternatively, device 2302 is may be advanced, deployed, or otherwise positioned adjacent to the perforation or target site while in a second or inflated state as depicted in FIG. 24C. FIG. 24C illustrates the device 2302 in an expanded state having diameter d2 (d2 is greater than d1) wherein wall 2402 impinges upon balloons 2312 and 2314 as a result of an inflation medium expanding balloon 2304. In some embodiments, the pressure or force exerted by balloon 2304 externally onto balloons 2312 and 2314 causes balloons 2312 and 2314 to break, burst, permeate, leak, or otherwise release compositions 2316 and 2318 as shown in a third or release state as in FIG. 24D. Balloon 2304 has diameter d3 in the release state where d3 is less than d2. FIG. 24E illustrates the fourth or combining state wherein compositions 2316 and 2318 combine together to form in-situ a foam that expands to fill the perforation or target site.

Figure 25A:
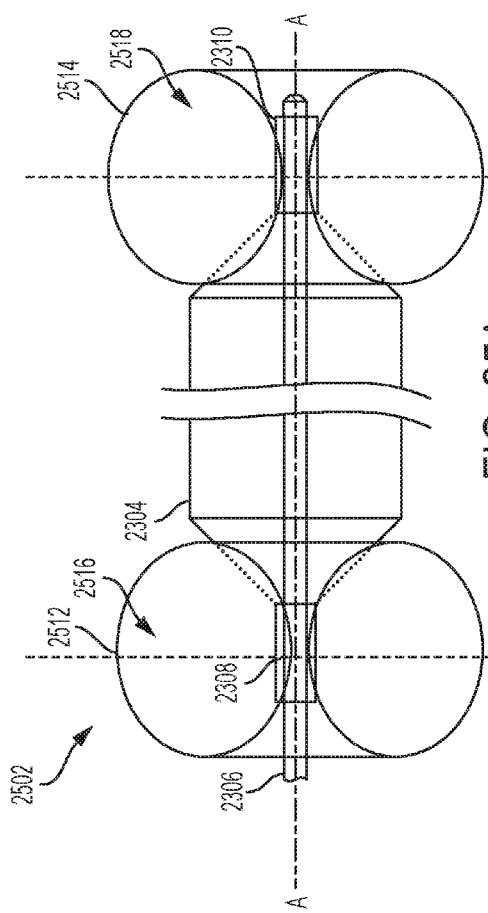
FIG. 25A is a side view of a distal portion of an expandable member wherein the rigid balloons include sub-balloons according other embodiments of the present disclosure.
Figure 25C:
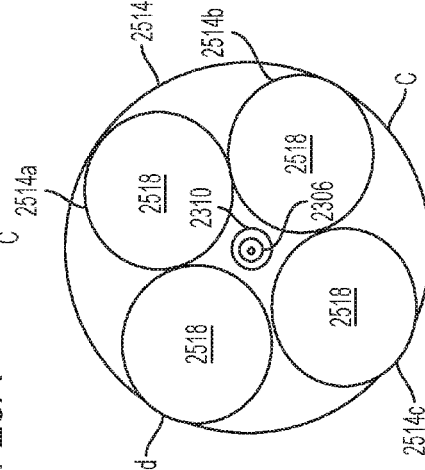
FIG. 25C is a cross-sectional view at line C of FIG. 25A.
Figure 25B:
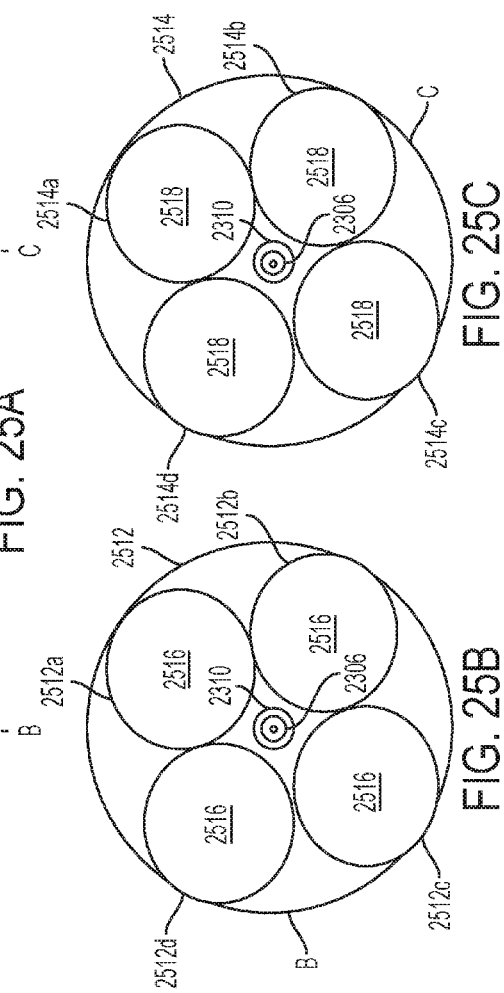
FIG. 25B is a cross-sectional view at line B of FIG. 25A.
Figure 26:
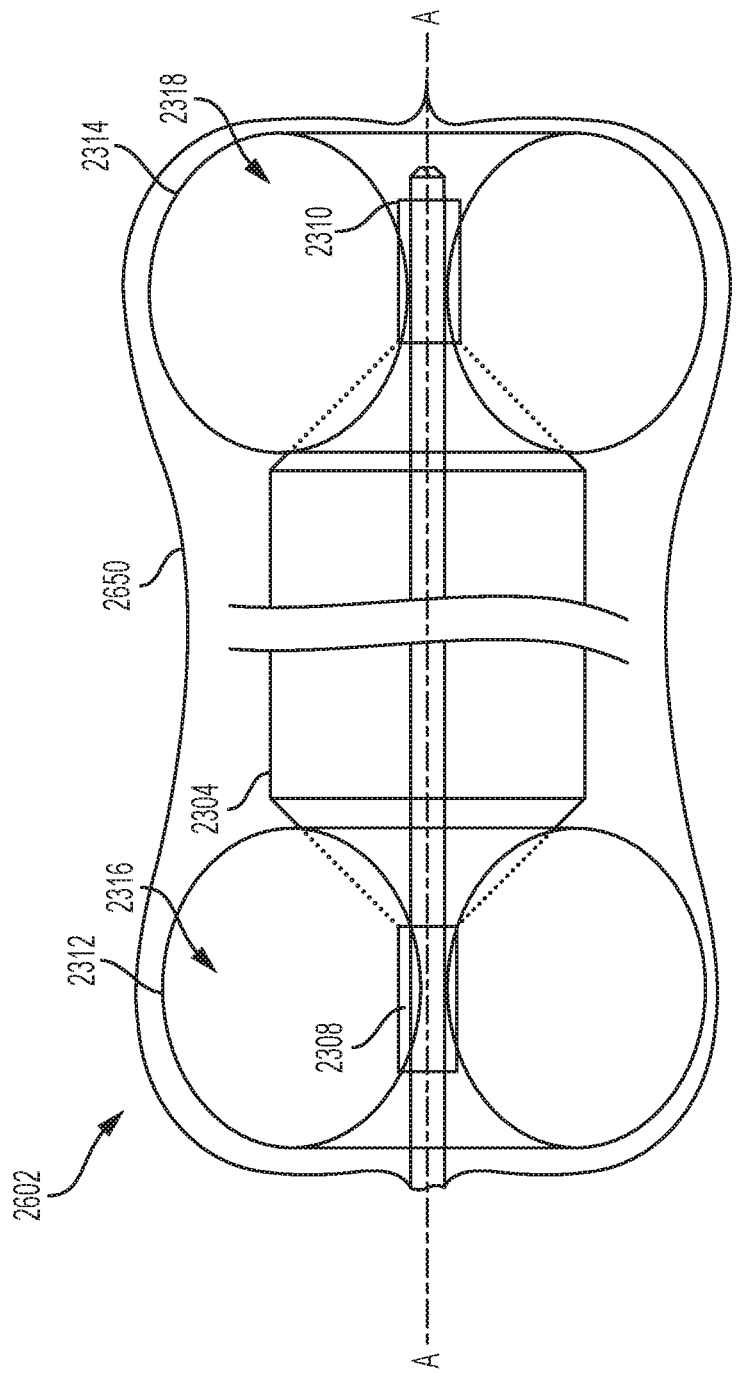
FIG. 26 is a side view of a distal portion of an expandable member including a fourth balloon enveloping the expandable member according to another embodiment of the present disclosure.

A number of variations and modifications to the occlusion balloon devices 2302 may be used. For example, FIG. 25A illustrates an expandable member 2502, wherein balloon 2512 comprises a plurality of sub-balloons 2512a containing composition 2516 and balloon 2514 comprises a plurality of sub-balloons 2514a containing composition 2518, where FIG. 25B illustrates a cross-sectional view of balloon 2512 at line B of FIG. 25A; and, FIG. 25C illustrates a cross-sectional view of balloon 2514 at line C of FIG. 25A. Upon expanding balloon 2304, sub-balloons 2512a and 2514a are configured to release substantially simultaneously compositions 2516 and 2518 to allow combining of compositions 2516 and 2518 to form in-situ biocompatible foam. As another example, FIG. 26 illustrates an expandable member 2602 further comprising a balloon 2650 enveloping balloon 2304 and balloons 2312 and 2314 (containing compositions 2316 and 2318, respectively), wherein balloon 2650 is configured to break prior to balloon 2312 releasing composition 2316 and balloon 2314 releasing composition 2318. The compositions combine to form in-situ biocompatible foam. The biocompatible form forms an occlusion patch at a perforation in a vessel or a target site to be occluded.

In some embodiments, the inflatable balloon 2304 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 2304 may be formed of one or more elastomeric materials, such as polyurethane. For example, the inflatable balloon 2304 may be formed of Pellethane®, specifically 80AE Pellethane®, which is available from The Lubrizol Corporation of Wickliffe, Ohio. The inflatable balloon 2304 may have a Shore A durometer of about 85 A (that is, 85A±4 A). To inflate the inflatable balloon 2304 to a diameter that causes balloons 2312 and 2314 to release compositions 2316 and 2318, for example, it may also be desirable to inflate the inflatable balloon 2304 with an inflation fluid to a pressure within the balloon inflation chamber 2404 from about 0 psi to about 3 psi. The amount of inflation fluid used to inflate the inflatable balloon 2304 to such a pressure and/or at the desired diameter is about 25 ml (cc).

Figure 27:
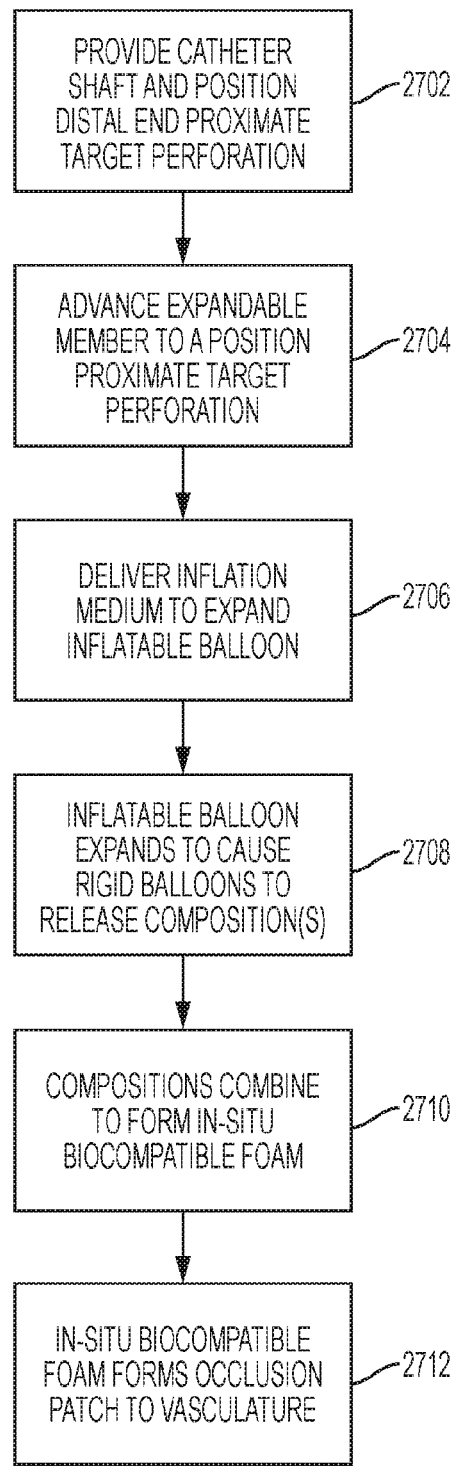
FIG. 27 is a flow chart illustrating a method for occluding a perforation in a blood vessel using an expandable member as in FIG. 23A.

FIG. 27 is a flow chart illustrating a method for occluding a perforation in a blood vessel according to embodiments of the present disclosure. The method comprises providing a catheter shaft, the catheter shaft having a proximal end and a distal end, and at least one lumen configured to receive an inflation medium. The catheter shaft is extended into a patient's blood vessel. Step 2702 includes providing the catheter shaft, extending the shaft, and positioning the distal end of the catheter shaft proximate the target perforation in a blood vessel. An expandable member is advanced distally to at least the distal end of the catheter shaft and proximate the target perforation as in step 2704. The expandable member comprises a first balloon having a first stiffness and containing a first composition; a second balloon having a second stiffness and containing a second composition; and, a third balloon having a third stiffness, the third balloon being disposed between the first balloon and the second balloon, wherein the third stiffness is less than the first stiffness and the second stiffness. The expandable member is similar to device 2302 described herein. Step 2706 includes delivering the inflation medium through the at least one lumen to the third balloon via one or more apertures to expand the third balloon. Step 2708 includes expanding the third balloon sufficiently to cause the first balloon and the second balloon to release substantially simultaneously the first composition and the second composition. For example, and referring again to FIG. 23, wherein balloons 2312 and 2314 are rigid and non-compliant, balloons 2312 and 2314 have a pressure strength at burst less than that of balloon 2304, expanding balloon 2304 causes the balloons 2312 and 2314 to break and release substantially simultaneously compositions 2316 and 2318. Alternatively, balloons 2312a and 2314a include micropores, 2312a comprises a first plurality of micropores and the balloon 2314a comprises a second plurality of micropores. Expanding balloon 2304 thus causes balloons 2312a and 2314a to expand and release substantially simultaneously composition 2316 through the first plurality of micropores and composition 2318 through the second plurality of micropores. Step 2710 includes combining the first composition and the second composition to form in-situ biocompatible foam. The in-situ biocompatible foam forms an occlusion patch for restricting the flow of blood in the vasculature of a patient as in step 2712. Optionally the method further includes a step of deflating the third balloon after the first balloon releases the first composition and the second balloon releases second composition. In some embodiments of the method, the expandable member is carried by the catheter shaft. In some embodiments of the method, the expandable member is disposed about an outer surface of the catheter shaft. In other embodiments of the method, the expandable member is disposed within a sheath. In some embodiments of the method, the first composition and the second composition are polymeric. In other embodiments of the method, the first composition is polymeric and the second composition is aqueous. In yet other embodiments of the method, the third balloon further includes an outer surface that is coated with a third composition, for example a pre-polymer, and the third composition is combinable with one of the first composition, the second composition, or both to form in-situ the biocompatible foam.

A number of variations and modifications of the disclosure can be used. It would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, for example, for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An expandable member for occluding a perforation in a blood vessel, the expandable member comprising:
   a first balloon having a first stiffness and containing a first composition;
   a second balloon having a second stiffness and containing a second composition; and
   a third balloon having a third stiffness, the third balloon being disposed between the first balloon and the second balloon, wherein the third stiffness is less than the first stiffness and the second stiffness, and whereupon expanding the third balloon causes the first balloon and the second balloon to release substantially simultaneously the first composition and the second composition to allow combining of the first composition and the second composition to form in-situ a biocompatible foam.

2. The expandable member of claim 1, the first balloon and the second balloon each having a pressure strength at burst less than that of the third balloon, whereupon expanding the third balloon causes the first balloon and the second balloon to break and release substantially simultaneously the first composition and the second composition.

3. The expandable member of claim 1, the first balloon further comprising a first plurality of micropores and the second balloon further comprising a second plurality of micropores whereupon expanding the third balloon causes the first balloon and the second balloon to expand and release substantially simultaneously the first composition through the first plurality of micropores and the second composition through the second plurality of micropores.

4. The expandable member of claim 1, the expandable member further comprising a longitudinal axis, wherein the first balloon, the second balloon, and the third balloon are longitudinally offset relative to one another.

5. The expandable member of claim 1, wherein the first composition and the second composition are polymeric.

6. The expandable member of claim 1, wherein the first composition is polymeric and the second composition is aqueous.

7. The expandable member of claim 1, the third balloon further having an outer surface, wherein the outer surface is coated with a third composition, and wherein the third composition is combinable with one of the first composition, the second composition, or both to form in-situ the biocompatible foam.

8. The expandable member of claim 5, further comprising a catheter shaft wherein the first balloon, the second balloon, and the third balloon are carried by the catheter shaft.

9. The expandable member of claim 5, further comprising a sheath having an inner lumen, wherein at least one of the first balloon, the second balloon, and the third balloon is moveable longitudinally within the inner lumen.

10. The expandable member of claim 1, wherein the first balloon comprises a plurality of first sub-balloons containing the first composition and the second balloon comprises a plurality of second sub-balloons containing the second composition.

11. The expandable member of claim 1 further comprising a fourth balloon enveloping the first balloon, the second balloon, and the third balloon, wherein the fourth balloon is configured to break prior to the first balloon releasing the first composition and the second balloon releasing the second composition.

12. The expandable member of claim 1, wherein the biocompatible foam forms an occlusion patch.

* * * * *